US011711972B1

United States Patent

(12) United States Patent
Lee et al.
(10) Patent No.: US 11,711,972 B1
(45) Date of Patent: Jul. 25, 2023

(54) ORGANIC ELECTRONIC ELEMENT COMPRISING COMPOUND FOR ORGANIC ELECTRONIC ELEMENT AND AN ELECTRONIC DEVICE THEREOF

(71) Applicant: DUK SAN NEOLUX CO., LTD., Cheonan-si (KR)

(72) Inventors: Sun Hee Lee, Cheonan-si (KR); Jung Geun Lee, Cheonan-si (KR); Hyoung Keun Park, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 18/172,551

(22) Filed: Feb. 22, 2023

(30) Foreign Application Priority Data

Jan. 9, 2023 (KR) ........................ 10-2023-0002969

(51) Int. Cl.

| | |
|---|---|
| ***C07C 211/54*** | (2006.01) |
| ***C07C 211/61*** | (2006.01) |
| ***C07D 487/04*** | (2006.01) |
| ***H01L 51/00*** | (2006.01) |
| ***H01L 51/50*** | (2006.01) |
| ***H10K 85/60*** | (2023.01) |
| ***H10K 50/15*** | (2023.01) |
| *H10K 102/00* | (2023.01) |

(52) U.S. Cl.

CPC .......... *H10K 85/633* (2023.02); *C07C 211/54* (2013.01); *H10K 50/15* (2023.02); *H10K 85/615* (2023.02); *H10K 85/622* (2023.02); *H10K 85/652* (2023.02); *H10K 85/654* (2023.02); *H10K 85/6572* (2023.02); *H10K 85/6576* (2023.02); *H10K 2102/3023* (2023.02)

(58) Field of Classification Search

CPC ... C07C 211/54; C07C 211/61; C07D 487/04; H10K 85/633; H10K 85/654; H10K 85/6572; H10K 85/6574; H10K 85/6576; H10K 50/19

See application file for complete search history.

(56) References Cited

FOREIGN PATENT DOCUMENTS

| | | | | |
|---|---|---|---|---|
| KR | 20220082949 A * | 6/2022 | ........... | C07D 333/76 |
| WO | WO-2020138877 A1 * | 7/2020 | ............. | C07C 15/28 |

* cited by examiner

*Primary Examiner* — Vu A Nguyen

(74) *Attorney, Agent, or Firm* — Vorys, Sater, Seymour and Pease LLP; Mih Suhn Koh

(57) ABSTRACT

Provided are an organic electronic element comprising an anode, a cathode, and an organic material layer between the anode and the cathode, and an electronic device comprising the organic electronic element, wherein the organic material layer includes a compound of P-1 to P-16 and Formula 2, therefore the driving voltage of the organic electronic element can be lowered and the luminous efficiency and lifespan can be improved.

14 Claims, 2 Drawing Sheets

ORGANIC ELECTRONIC ELEMENT COMPRISING COMPOUND FOR ORGANIC ELECTRONIC ELEMENT AND AN ELECTRONIC DEVICE THEREOF

BACKGROUND

[Technical Field]

The present invention relates to an organic electronic element using a compound for an organic electronic element and an electronic device thereof.

[Background Art]

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, the organic material layer may have a multi-layer structure composed of different materials in order to increase the efficiency and stability of the organic electronic element.

Currently, the portable display market tends to increase in size with large-area displays. Since the portable display has a battery that is a limited power supply, more efficient power consumption is required than the power consumption required in the existing portable display. Moreover, in addition to efficient power consumption, luminous efficiency and lifespan issues must also be resolved.

In order to solve problems of power consumption, luminous efficiency, and lifespan, research on a tandem OLED comprising 2 or more stacks (or light emitting units) in which each organic material layer includes an emitting layer is being conducted. In particular, research is being conducted to improve the power consumption, luminous efficiency, and lifespan of organic electronic elements by improving organic materials included in the stack.

Efficiency, lifespan and driving voltage are related to each other, and when the efficiency is increased, the driving voltage is relatively decreased, and as the driving voltage is decreased, crystallization of organic materials due to Joule heating generated during driving decreases, and consequently, the lifespan tends to increase. However, the efficiency cannot be maximized simply by improving the organic material. This is because, when the energy level and T1 value between each organic material, and the intrinsic properties (mobility, interfacial properties, etc.) of materials are optimally combined, long lifespan and high efficiency can be achieved at the same time. Therefore, it is necessary to develop a material that has high thermal stability and can efficiently balance charge in the emitting layer.

Also, a charge generation layer is required to increase the efficiency of current generated in the emitting layer and facilitate charge distribution between 2 or more stacks (or light emitting units) in Tandem OLED. Depending on how smooth the charge distribution in the charge generation layer is, it affects the driving voltage of the entire device, and depending on the energy level difference between the n-type charge generation layer and the p-type charge generation layer, the concentration of the doping material doped in the charge generation layer, and the like, the charge injection characteristics and lifespan of the device are also affected.

That is, the efficiency, lifespan, and driving voltage of the organic electronic element may vary depending on which organic material is used in combination with which layer in Tandem OLED, but until now, development of stable and efficient organic material layer materials for organic electronic elements have not been sufficiently developed.

DETAILED DESCRIPTION OF THE INVENTION

[Summary]

An object of the present invention is to provide an organic electronic element and an electronic device comprising a compound capable of lowering the driving voltage of the device and improving the luminous efficiency, color purity, stability and lifespan of the device.

Technical Solution

In one aspect, the present invention comprises an organic electronic element comprising a first electrode; a second electrode; and an organic layer disposed between the first electrode and the second electrode; wherein the organic layer comprises a first stack and a second stack, and a charge generation region between the first stack and the second stack, wherein the charge generation region comprises an n-type charge generation layer and a p-type charge generation layer, wherein the n-type charge generation layer faces the first electrode, and the p-type charge generation layer faces the second electrode, wherein the p-type charge generation layer is any one selected from the group consisting of Formulas P-1 to P-16.

P-1

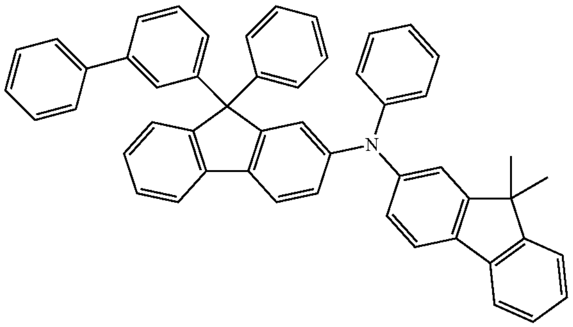

P-2

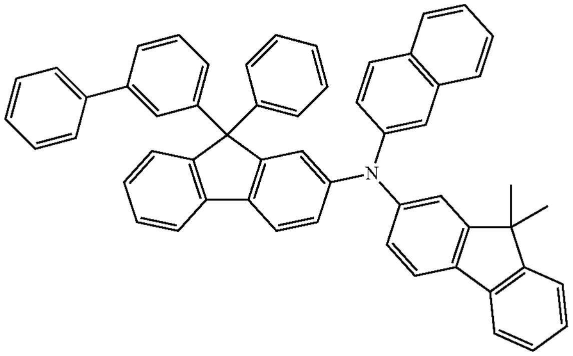

-continued
P-3
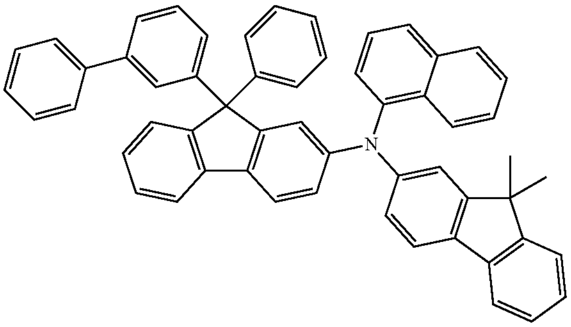
P-4
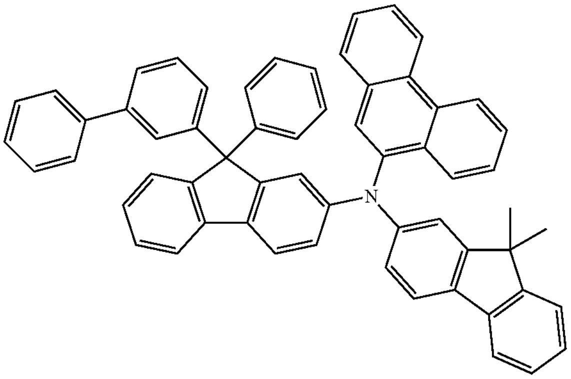
P-5
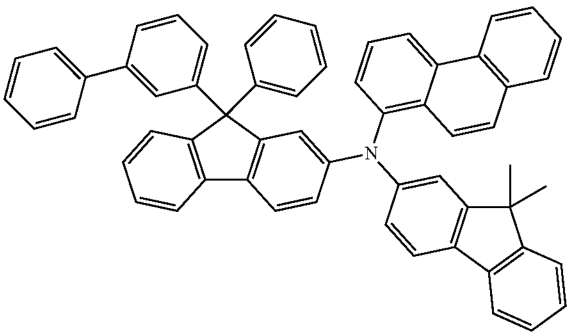
P-6
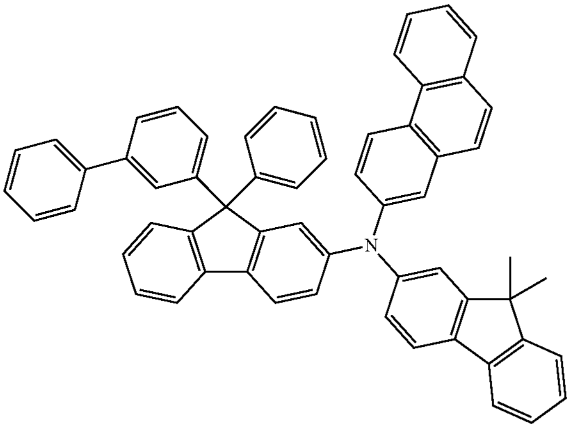
-continued
P-7
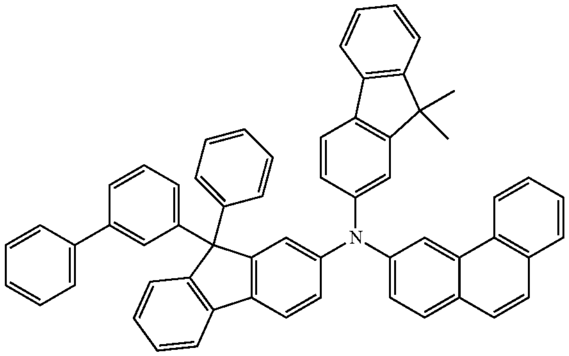
P-8
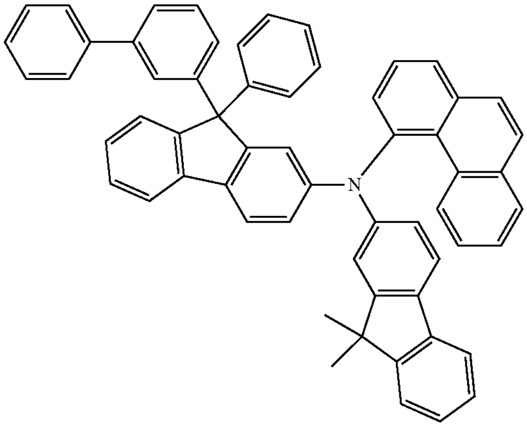
P-9
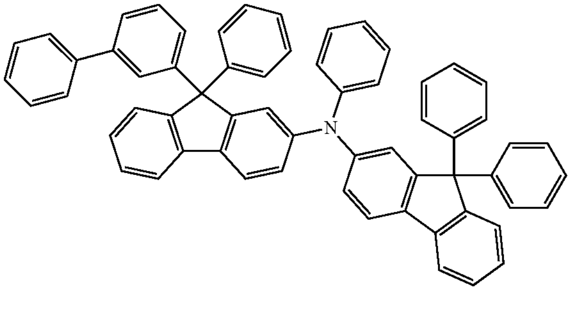

-continued
P-10
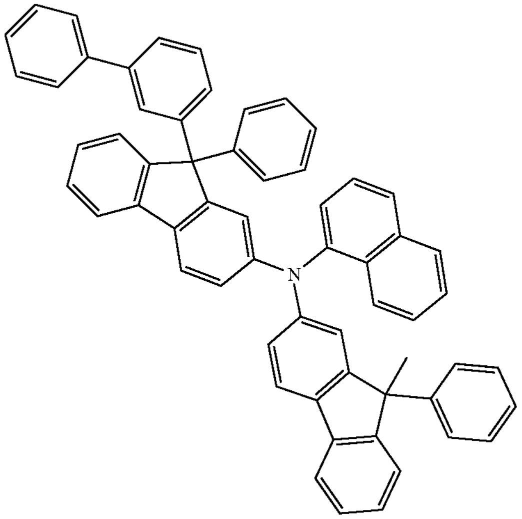
P-11
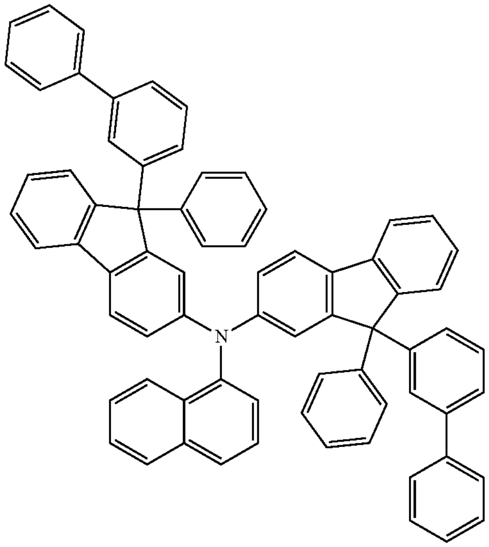
P-12
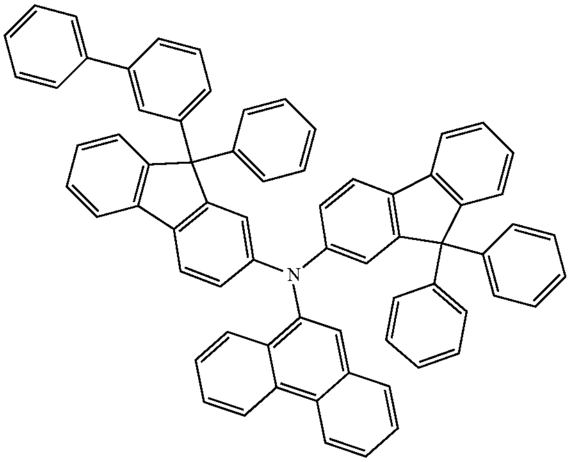
-continued
P-13
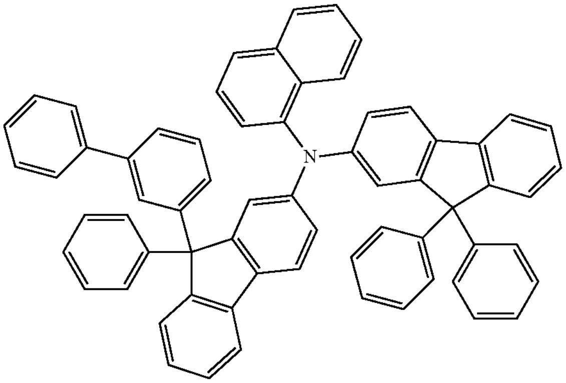
P-14
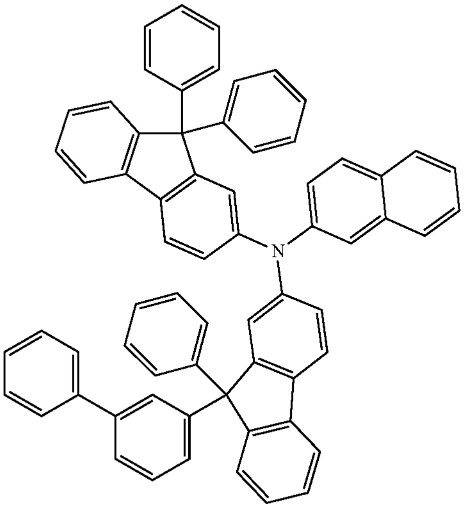
P-15
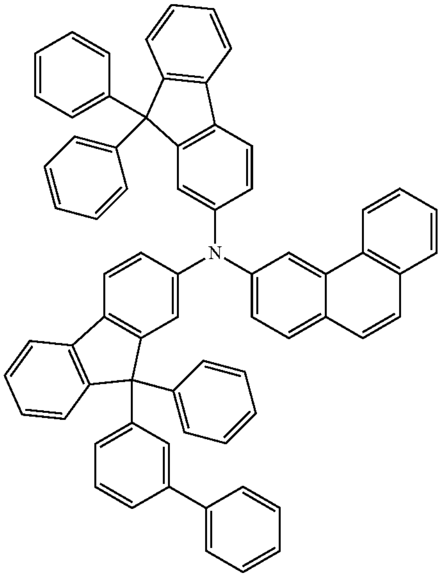

-continued

P-16

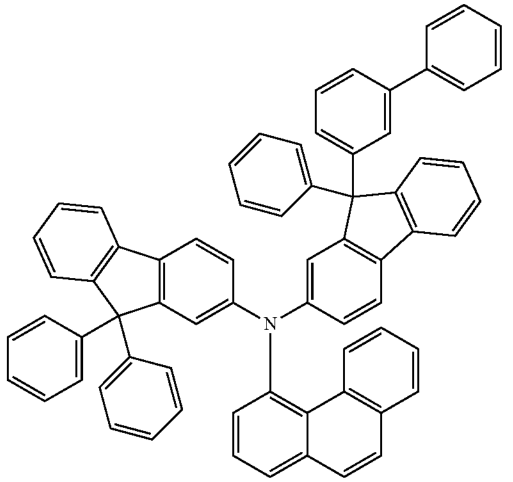

In another aspect, the present invention provides an electronic device including the organic electronic element.

[Effects of the Invention]

By using the compound according to the present invention, high luminous efficiency, low driving voltage and high heat resistance of the element can be achieved, and color purity and lifespan of the element can be greatly improved.

Figure 1:
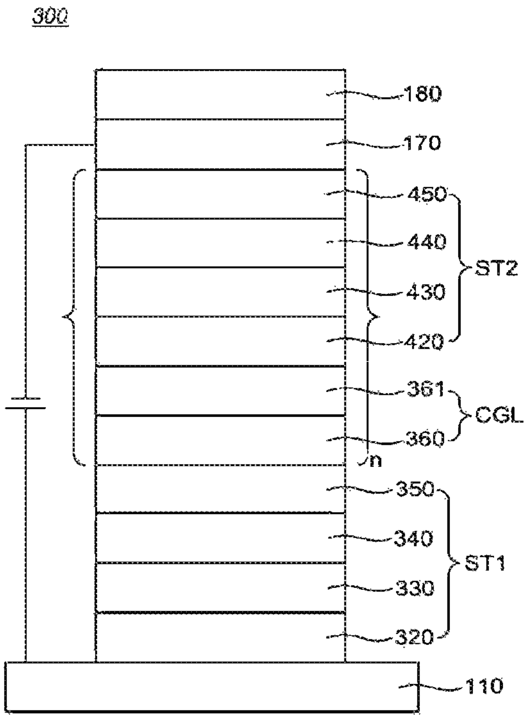
FIG. 1 to FIG. 3 are exemplary views of an organic electroluminescent device according to the present invention.

| [Explanation of code] | |
|---|---|
| 100, 200, 300: organic electronic element | 110: the first electrode |
| 120: hole injection layer | 130: hole transport layer |
| 140: emitting layer | 150: electron transport layer |
| 160: electron injection layer | 170: second electrode |
| 180: light efficiency enhancing Layer | 210: buffer layer |
| 220: emitting auxiliary layer | 320: first hole injection layer |
| 330: first hole transport layer | 340: first emitting layer |
| 350: first electron transport layer | 360: first charge generation layer |
| 361: second charge generation layer | 420: second hole injection layer |
| 430: second hole transport layer | 440: second emitting layer |
| 450: second electron transport layer | CGL: charge generation layer |
| ST1: first stack | ST2: second stack |

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

The terms "aryl group" and "arylene group" used in the present invention have 6 to 60 carbon atoms, respectively, unless otherwise specified, but are not limited thereto. In the present invention, an aryl group or an arylene group means a single ring or multiple ring aromatic, and includes an aromatic ring formed by an adjacent substituent joining or participating in a reaction.

For example, the aryl group may be a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of a single ring or multiple ring, and may include heteroaliphadic ring and heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including $SO_2$ instead of carbon consisting of cycle. For example, "heterocyclic group" includes the following compound.

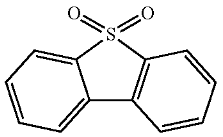 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group" means that at least one of the substituents R, R', R" is a substituent other than hydrogen, and include those in which R and R' are bonded to each other to form a spiro compound together with the carbon to which they are bonded.

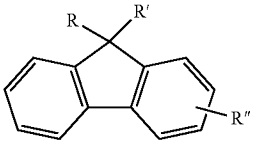

The term "spiro compound", as used herein, has a 'spiro union', and a spiro union means a connection in which two rings share only one atom. At this time, atoms shared in the two rings are called 'spiro atoms', and these compounds are called 'monospiro-', 'di-spiro-' and 'tri-spiro-', respectively, depending on the number of spiro atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Also, unless expressly stated, as used herein, "substituted" in the term "substituted or unsubstituted" means substituted with one or more substituents selected from the group consisting of deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group, but is not limited to these substituents.

Also, unless there is an explicit explanation, the formula used in the present invention is the same as the definition of the substituent by the exponent definition of the following formula.

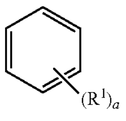

Here, when a is an integer of 0, the substituent $R^1$ is absent, when a is an integer of 1, the sole substituent $R^1$ is linked to any one of the carbon constituting the benzene ring, when a is an integer of 2 or 3, each is combined as follows, where $R^1$ may be the same or different from each other, when a is an integer of 4 to 6, it is bonded to the carbon of the benzene ring in a similar manner, while the indication of the hydrogen bonded to the carbon forming the benzene ring is omitted.

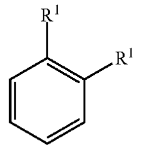

(a = 2)

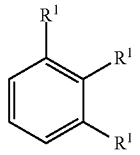

(a = 3)

Hereinafter, a layered structure of an organic electronic element including the compound of the present invention will be described with reference to FIG. 1.

In adding reference numerals to the components of each drawing, it should be noted that the same components have the same numerals as much as possible even if they are displayed on different drawings. Also, in describing the present invention, if it is determined that a detailed description of a related known configuration or function may obscure the gist of the present invention, the detailed description will be omitted.

FIG. 1 is an exemplary view of an organic electronic element according to an embodiment of the present invention.

Referring to FIG. 1, an organic electronic element (300) according to an embodiment of the present invention comprises 2 or more sets of multi-layer stacks (ST1, ST2) between a first electrode (110) and a second electrode (170), and a charge generation layer (CGL) may be formed between the stacks of organic material layers.

Specifically, the organic electronic element according to an embodiment of the present invention comprises a first electrode (110), a first stack (ST1), a charge generation layer (CGL), a second stack (ST2), and a second electrode. (170) and a light efficiency enhancing layer (180).

The first stack (ST1) is an organic material layer formed on the first electrode (110), which comprises the first hole injection layer (320), the first hole transport layer (330), the first emitting layer (340), and the first electron transport layer (350), and the second stack (ST2) may comprise a second hole injection layer (420), a second hole transport layer (430), a second emitting layer (440), and a second electron transport layer (450) and if necessary, the second hole injection layer (420) of the second stack (ST2) may be omitted. In this way, the first stack and the second stack may be organic material layers having the same stacked structure or organic material layers having different stacked structures.

A charge generation layer (CGL) may be formed between the first stack (ST1) and the second stack (ST2). The charge generation layer (CGL) may comprise a n-type charge generation layer (360) adjacent to the first electron transport layer (350) of the first stack (ST1) and a p-type charge generation layer (361) adjacent to the second hole injection layer (420) of the second stack (ST2). The charge generation layer (CGL) is formed between the first emitting layer (340) and the second emitting layer (440) to increase the efficiency of current generated in each emitting layer and to smoothly distribute charges. In the case of a top emission organic light emitting device, optical energy loss due to SPPs (surface plasmon polaritons) in the second electrode (170) can be reduced by forming the light efficiency enhancing layer (180), and in the case of a bottom emission organic light emitting device, the light efficiency enhancing layer (180) may serve as a buffer for the second electrode (170).

When a plurality of emitting layers are formed by a multi-layer stack structure method as shown in FIG. 1, an organic light emitting device emitting white light by a mixing effect of light emitted from each emitting layer may be manufactured, as well as an organic light emitting device emitting light of various colors. Although not shown in FIG. 1, a buffer layer and an emitting auxiliary layer may be further formed between the hole transport layer and the emitting layer of each stack, and an electron transport auxiliary layer may be further formed between the emitting layer and the electron transport layer.

Although FIG. 1 has described a tandem OLED with 2 stacks, the organic electronic element according to the present invention can be a tandem OLED with 2 or more stacks. (e.g., a tandem OLED with 3 stacks, a tandem OLED with 4 stacks)

Preferably, the compounds represented by Formulas P-1 to P-16 and Formula 2 of the present invention may be used as a charge generation layer (CGL), more preferably, the compound represented by Formulas P-1 to P-16 may be used as a p-type charge generation layer, and the compound represented by Formula 2 may be used as an n-type charge generation layer.

Since the band gap, electrical properties, interface properties, etc. may vary depending on which substituent is attached to which position even in the same or similar core, selection of the core and research on the combination of sub-substituents bound thereto is required, and in particular, long life and high efficiency can be achieved at the same time when the optimal combination of the energy level and T1 value between each organic material layer and the intrinsic properties of the material (mobility, interfacial property, etc.) is achieved.

An organic light emitting device according to an embodiment of the present invention may be manufactured using various deposition methods. It can be manufactured using a deposition method such as PVD or CVD, for example, after the anode (110) is formed by depositing a metal or a conductive metal oxide or an alloy thereof on a substrate, and forming a first stack (ST1) sequentially comprising the first hole injection layer thereon (320), the first hole transport layer (330), the first emitting layer (340) and the first electron transport layer (350) thereon, and forming a charge generation layer (CGL) sequentially comprising an n-type charge generation layer (360) and a p-type charge generation layer (361) for connecting the 2 stacks thereon, and after forming a second stack (ST2) sequentially comprising the second hole injection layer (420), the second hole transport layer (430), the second emitting layer (440), and the second electron transport layer (450) thereon, and forming an electron injection layer thereon, and by depositing a material that can be used as the cathode (170) thereon. Also, a buffer layer (not shown) and an emitting auxiliary layer (not shown) may be further formed between the hole transport layer and the emitting layer of each stack, and an electron transport auxiliary layer (not shown) may be further formed between the emitting layer and the electron transport layer, and as described above, 2 or more stacked structures may be formed.

Moreover, the organic material layer can be manufactured with a smaller number of layers by a method such as a solution process or a solvent process rather than a deposition method using various polymer materials, for example a spin coating process, a nozzle printing process, an inkjet printing process, a slot coating process, a dip coating process, a roll-to-roll process, a doctor blading process, screen printing process, or a thermal transfer method, etc. Since the organic material layer according to the present invention can be formed in various ways, the scope of the present invention is not limited by the forming method.

In addition, the organic electronic element according to an embodiment of the present invention may be selected from the group consisting of organic light emitting devices, organic solar cells, organic photoreceptors, organic transistors, devices for monochromatic lighting, and devices for quantum dot displays.

Another embodiment of the present invention may comprise an electronic device comprising a display device including the above-described organic electronic element of the present invention and a control unit driving the display device. At this time, the electronic device may be a current or future wired/wireless communication terminal, and covers all kinds of electronic devices including mobile communication terminals such as mobile phones, a personal digital assistant(PDA), an electronic dictionary, a point-to-multipoint(PMP), a remote controller, a navigation unit, a game player, various kinds of TVs, and various kinds of computers.

Hereinafter, an organic electronic element according to an aspect of the present invention will be described.

An organic electronic element according to an embodiment of the present invention comprises a first electrode; a second electrode; and an organic layer disposed between the first electrode and the second electrode; wherein the organic layer includes a first stack and a second stack, wherein a charge generation region is further comprised between the first stack and the second stack, wherein the charge generation region comprises an n-type charge generation layer and a p-type charge generation layer, wherein the n-type charge generation layer faces the first electrode, wherein the p-type charge generation layer faces the second electrode, wherein the p-type charge generation layer is any one selected from the group consisting of Formulas P-1 to P-16.

P-1

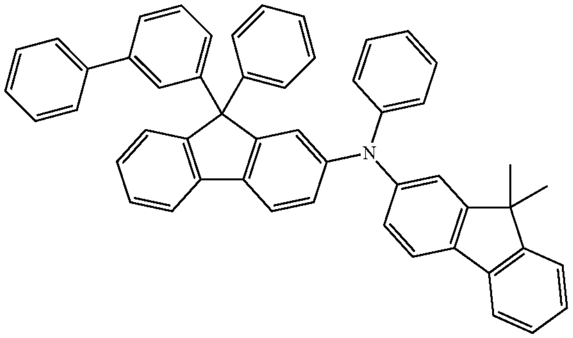

-continued
P-2
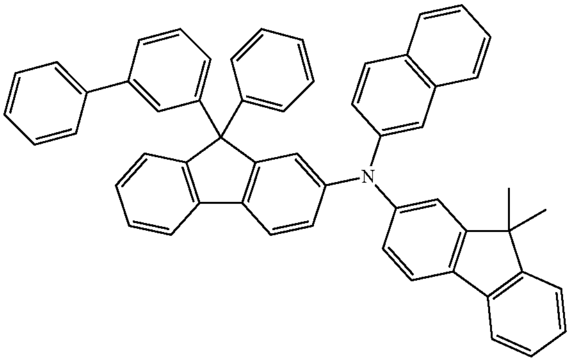
P-3
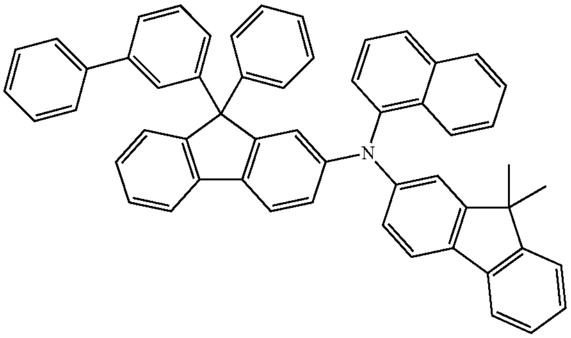
P-4
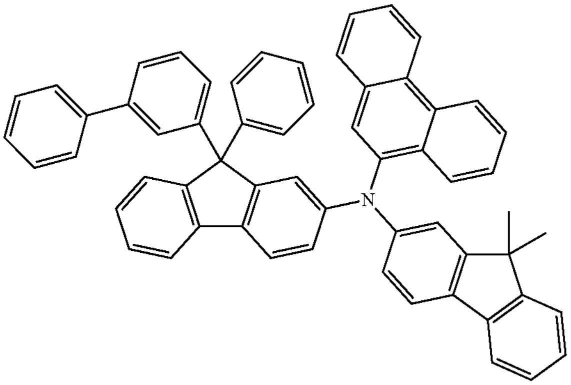
P-5
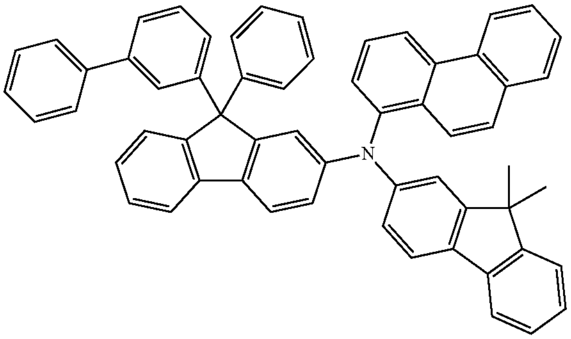
-continued
P-6
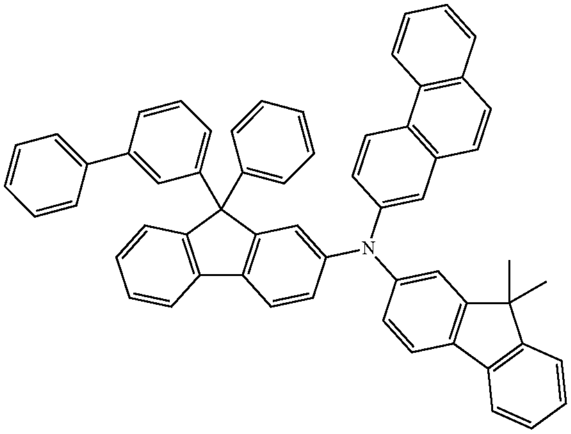
P-7
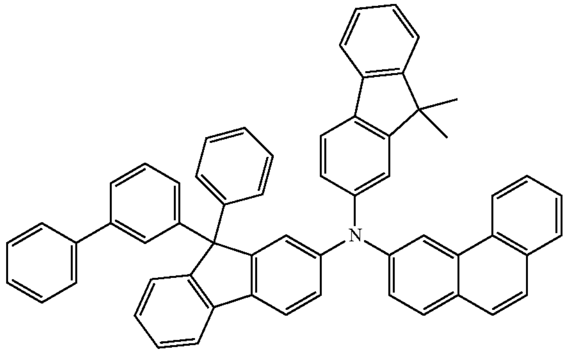
P-8
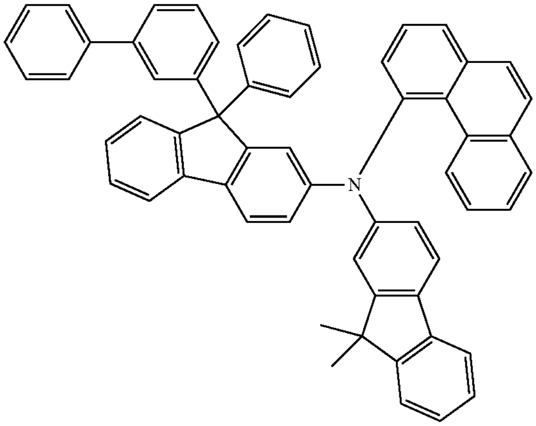
P-9
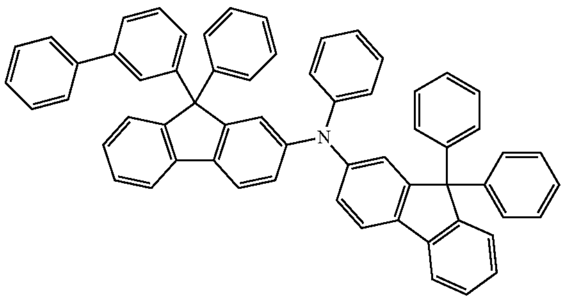

-continued
P-10
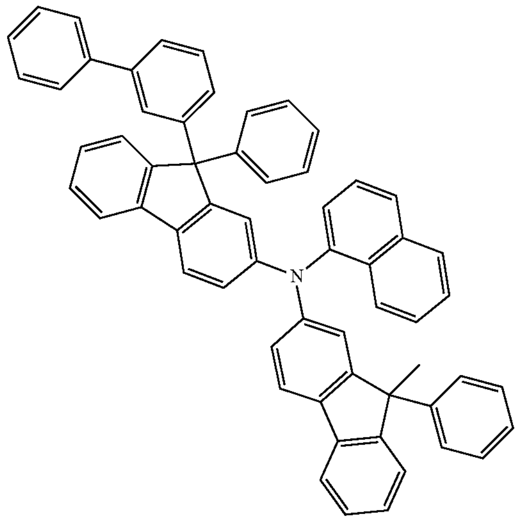
P-11
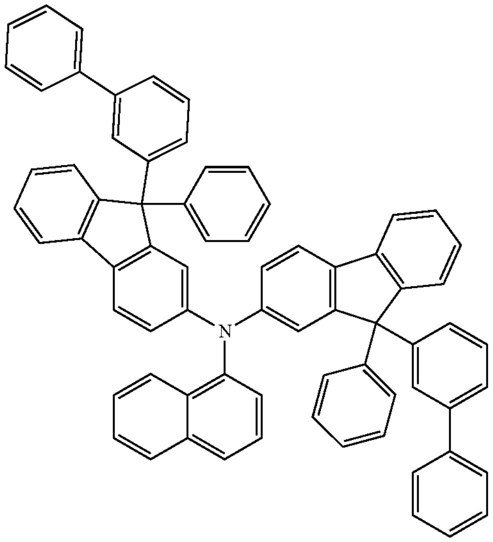
P-12
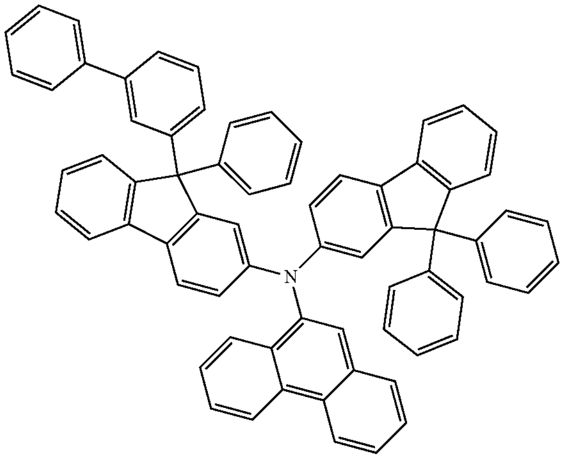
-continued
P-13
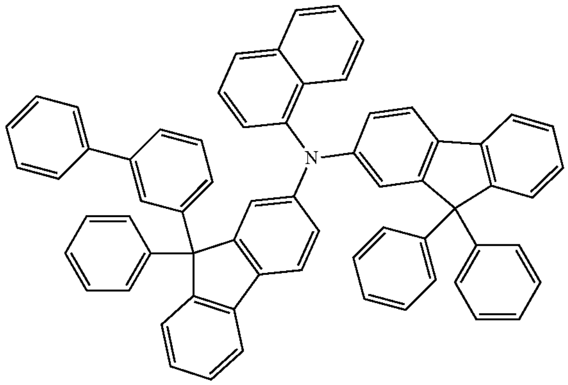
P-14
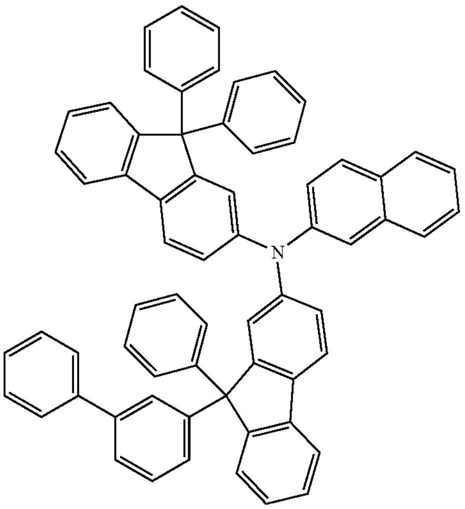
P-15
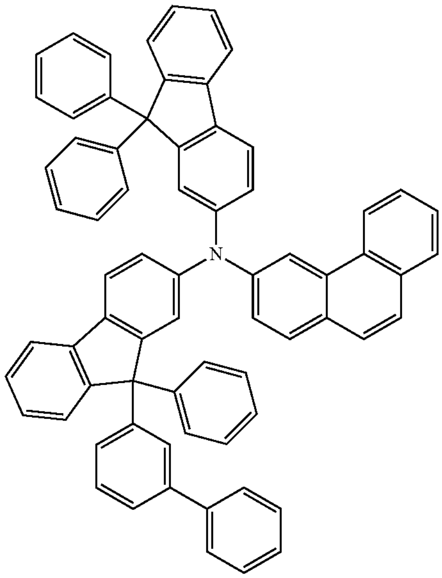

-continued

P-16

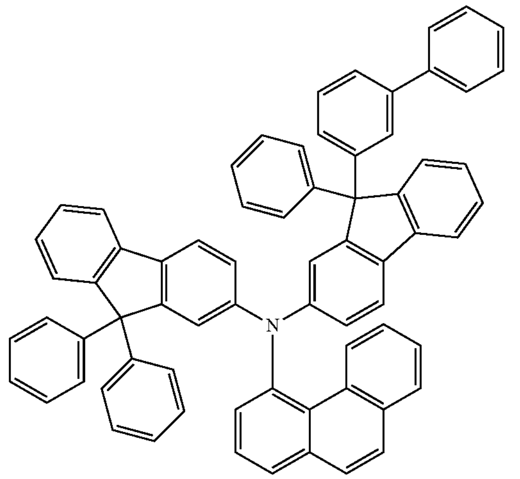

Also, the present invention provides an organic electronic element comprising that the second stack sequentially comprises a hole transport region, an emitting layer, and an electron transport region, wherein the hole transport region comprises at least one hole transport layer, wherein the hole transport layer comprises a compound selected from the group consisting of Formulas P-1 to P-16.

Also, the present invention provides an organic electronic element comprising an emitting auxiliary layer on the hole transport layer.

The p-type charge generation layer may be doped with Formula 3.

Formula 3

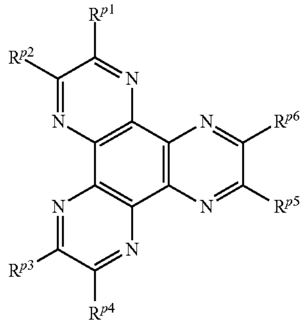

In Formula 3, each symbol may be defined as follows.

1) $R^{p1}$, $R^{p2}$, $R^{p3}$, $R^{p4}$, $R^{p5}$ and $R^{p6}$ are each independently selected from the group consisting of hydrogen; halogen; nitrile group; nitro group; $-SO_2R$; $-SOR$; $-SO_2NR_2$; $-SO_3R$; trifluoromethyl group; $-COOR$; $-CONHR$; $-CONRR'$; $-NRR'$; a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group;

when $R^{p1}$, $R^{p2}$, $R^{p3}$, $R^{p4}$, $R^{p5}$ and $R^{p6}$ are an aryl group, it may be preferably a $C_6$-$C_{30}$ aryl group, and more preferably a $C_6$-$C_{25}$ aryl group, for example, it may be phenyl, biphenyl, terphenyl, naphthalene, etc., when $R^{p1}$, $R^{p2}$, $R^{p3}$, $R^{p4}$, $R^{p5}$ and $R^{p6}$ are a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrim idine, benzofuropyrimidine, phenothiazine, phenylphenothiazine, etc., when $R^{p1}$, $R^{p2}$, $R^{p3}$, $R^{p4}$, $R^{p5}$ and $R^{p6}$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

when $R^{p1}$, $R^{p2}$, $R^{p3}$, $R^{p4}$, $R^{p5}$ and $R^{p6}$ are an alkyl group, it may be preferably a $C_1$-$C_{30}$ alkyl group, and more preferably a $C_1$-$C_{24}$ alkyl group, when $R^{p1}$, $R^{p2}$, $R^{p3}$, $R^{p4}$, $R^{p5}$ and $R^{p6}$ are an alkoxyl group, it may be preferably an $C_1$~$C_{24}$ alkoxyl group, when $R^{p1}$, $R^{p2}$, $R^{p3}$, $R^{p4}$, $R^{p5}$ and $R^{p6}$ are an aryloxy group, it may be preferably an $C_6$~$C_{24}$ aryloxy group, 2) R and R' are each independently selected from the group consisting of a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; and a $C_2$-$C_{20}$ alkynyl group;

when R and R' are an aryl group, it may be preferably a $C_6$-$C_{30}$ aryl group, and more preferably a $C_6$-$C_{25}$ aryl group, for example, it may be phenyl, biphenyl, terphenyl, naphthalene, etc., when R and R' are a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc., when R and R' are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

when R and R' are an alkyl group, it may be preferably a $C_1$-$C_{30}$ alkyl group, and more preferably a $C_1$-$C_{24}$ alkyl group, Formula 3 may preferably be any one of the following compounds E-1 to E-5.

E-1

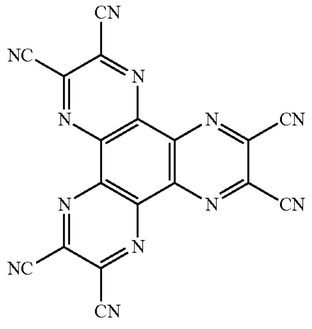

-continued
E-2
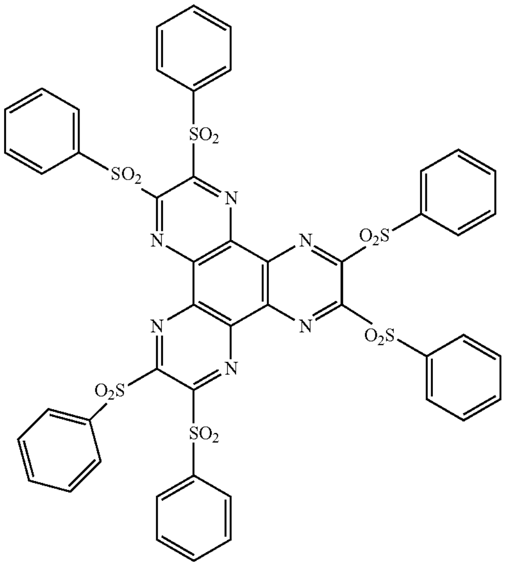
E-3
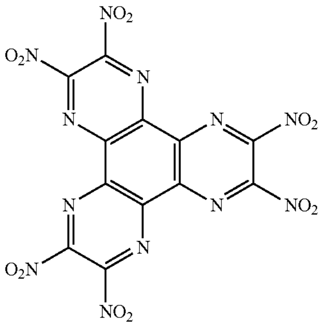
E-4
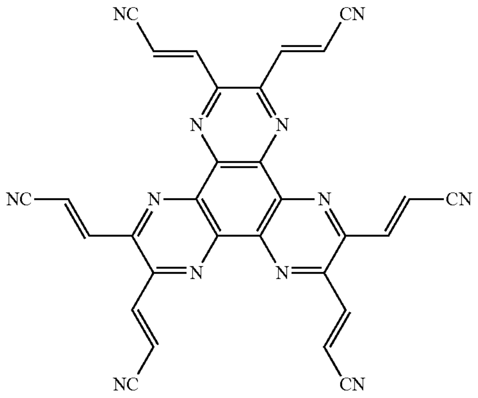
E-5
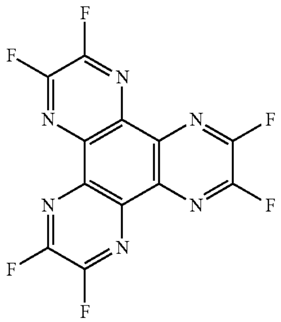
In another example, the p-type charge generation layer may be doped with any one of the following compounds E-6 to E-26.
E-6
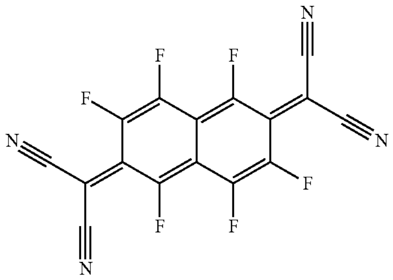
E-7
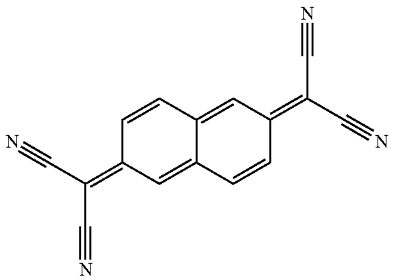
E-8
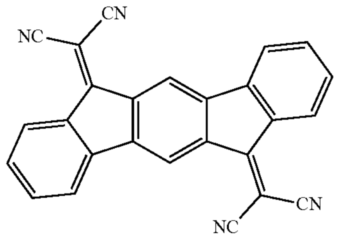
E-9
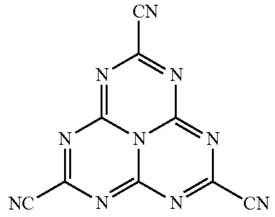
E-10
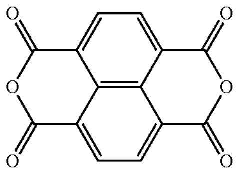
E-11
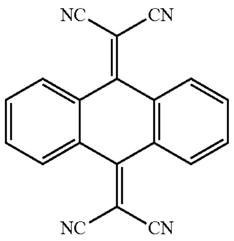

-continued
E-12
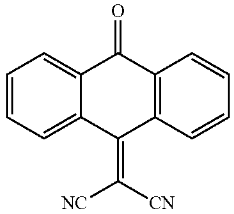
E-13
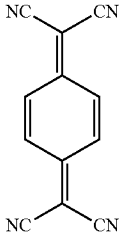
E-14
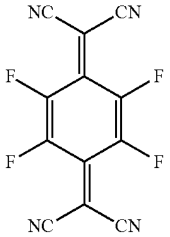
E-15
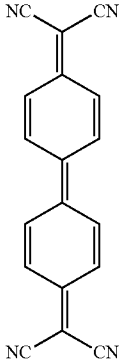
E-16
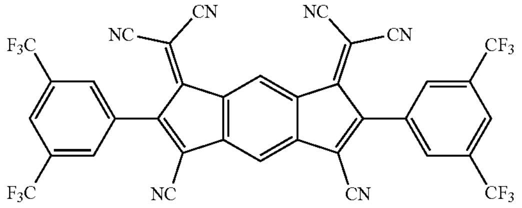
E-17
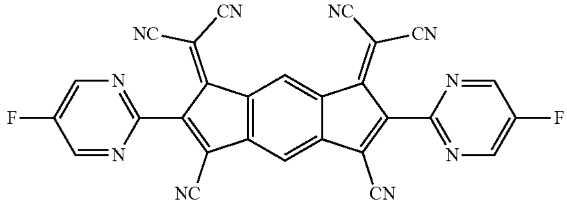
-continued
E-18
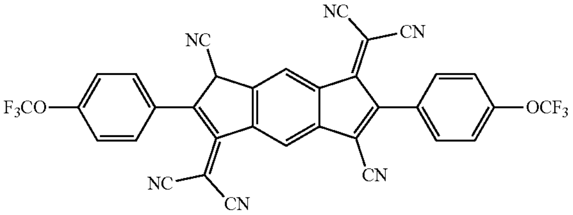
E-19
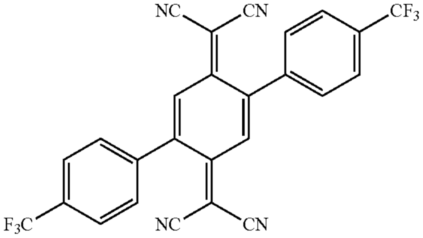
E-20
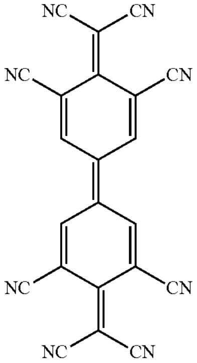
E-21
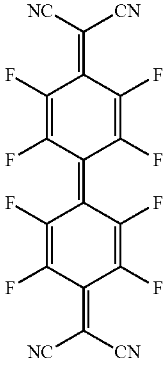
E-22
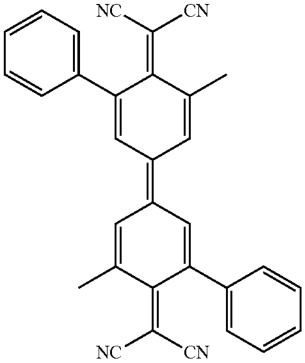

-continued

E-23

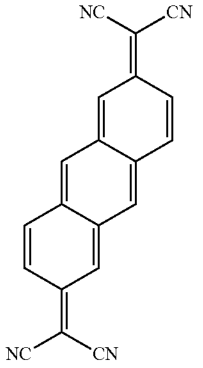

E-24

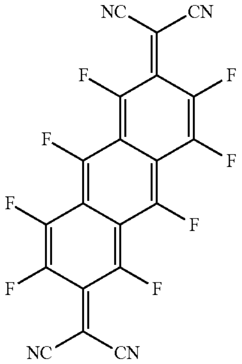

E-25

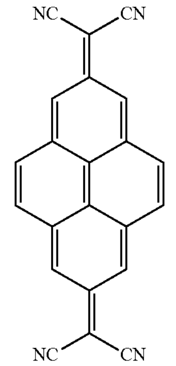

E-26

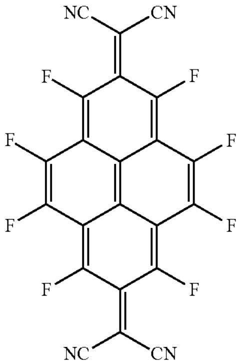

The p-type charge generation layer may be doped with any one of the compounds E-1 to E-18 at 0.1 w% to 50 w%, preferably at 3 w% to 15 w%, and more preferably at 5 w% to 10 w%.

Also, the present invention provides an organic electronic element in which the n-type charge generation layer comprises a compound represented by Formula 2.

Formula 2

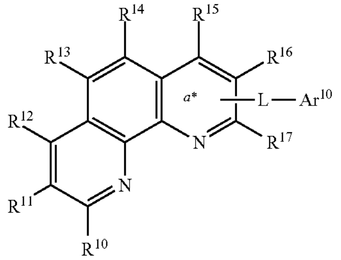

In Formula 2, each symbol may be defined as follows.

1) $R^{10}$, $R^{11}$, $R^{12}$, $R^{13}$, $R^{14}$, $R^{15}$, $R^{16}$ and $R^{17}$ are each independently selected from a group consisting of hydrogen; deuterium; halogen; cyano group; nitro group;

a $C_6$-$C_{60}$ aryl group; fluorenyl group; a $C_2$-$C_{60}$ heterocyclic group including at least one heteroatom of O, N, S, Si or P; a $C_3$-$C_{60}$ aliphatic ring; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group;

However, at least one of $R^{15}$, $R^{16}$ and $R^{17}$ is bonded to a* to form a single bond, when $R^{10}$, $R^{11}$, $R^{12}$, $R^{13}$, $R^{14}$, $R^{15}$, $R^{16}$ and $R^{17}$ are an aryl group, it may be preferably a $C_6$-$C_{30}$ aryl group, and more preferably a $C_6$-$C_{25}$ aryl group, for example, it may be phenyl, biphenyl, terphenyl, naphthalene, etc., when $R^{10}$, $R^{11}$, $R^{12}$, $R^{13}$, $R^{14}$, $R^{15}$, $R^{16}$ and $R^{17}$ are a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc., when $R^{10}$, $R^{11}$, $R^{12}$, $R^{13}$, $R^{14}$, $R^{15}$, $R^{16}$ and $R^{17}$ are an aliphatic ring group, it may be preferably a $C_3$-$C_{30}$ aliphatic group, more preferably a $C_3$-$C_{24}$ aliphatic ring group.

when $R^{10}$, $R^{11}$, $R^{12}$, $R^{13}$, $R^{14}$, $R^{15}$, $R^{16}$ and $R^{17}$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

when $R^{10}$, $R^{11}$, $R^{12}$, $R^{13}$, $R^{14}$, $R^{15}$, $R^{16}$ and $R^{17}$ are an alkyl group, it may be preferably a $C_1$-$C_{30}$ alkyl group, and more preferably a $C_1$-$C_{24}$ alkyl group, when $R^{10}$, $R^{11}$, $R^{12}$, $R^{13}$, $R^{14}$, $R^{15}$, $R^{16}$ and $R^{17}$ are an alkoxyl group, it may be preferably an $C_1$~$C_{24}$ alkoxyl group, when $R^{10}$, $R^{11}$, $R^{12}$, $R^{13}$, $R^{14}$, $R^{15}$, $R^{16}$ and $R^{17}$ are an aryloxy group, it may be preferably an $C_6$~$C_{24}$ aryloxy group, 2) L is an $C_6$-$C_{60}$ arylene group; or a $C_2$-$C_{60}$ heterocyclic group including at least one heteroatom of O, N, S, Si or P;

when L is an arylene group, it may be preferably a $C_6$-$C_{30}$ arylene group, more preferably a $C_6$-$C_{20}$ arylene group, for example, phenylene, biphenylene, naphthylene, terphenylene, anthracenylene, etc., when L is a heterocyclic group, it may be preferably a $C_2$~$C_{30}$ heterocyclic group, and more preferably a $C_2$~$C_{20}$ heterocyclic group, for example, pyridine, pyrimidine, quinoline, quinazoline, quinoxaline, dibenzofuran, dibenzothiophene, naphthobenzothiophene, naphthobenzofuran, benzofuran, benzothiophene etc., 3) $Ar^{10}$ is an $C_6$-$C_{60}$ aryl group; or a $C_2$-$C_{60}$ heterocyclic group including at least one heteroatom of O, N, S, Si or P;

When $Ar^{10}$ is an aryl group, it may be preferably a $C_6$-$C_{30}$ aryl group, and more preferably a $C_6$-$C_{25}$ aryl group, for example, it may be phenyl, biphenyl, terphenyl, naphthalene, etc., When $Ar^{10}$ is a heterocyclic group, it may be preferably a $C_2$~$C_{30}$ heterocyclic group, and more preferably a $C_2$~$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc., wherein the aryl group, arylene group, heterocyclic group, fluorenyl group, aliphatic ring, fused ring group, alkyl group, alkenyl group, alkynyl group, alkoxy group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_1$-$C_{20}$ alkyl group substituted with deuterium; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_3$-$C_{20}$ aliphatic ring group; $C_3$-$C_{20}$ aliphatic ring group substituted with deuterium; $C_2$~$C_{20}$ heterocyclic group; $C_2$~$C_{20}$ heterocyclic group substituted with deuterium; $C_3$~$C_{20}$ cycloalkyl group; $C_7$-$C_{20}$ arylalkyl group; and $C_8$-$C_{20}$ arylalkenyl group; and also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Also, L is represented by any one of Formulas L-1 to L-16.

[Formula L-1]

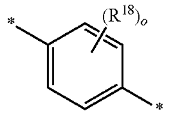

[Formula L-2]

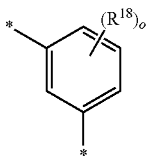

[Formula L-3]

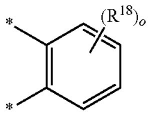

[Formula L-4]

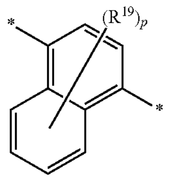

-continued

[Formula L-5]

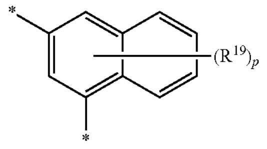

[Formula L-6]

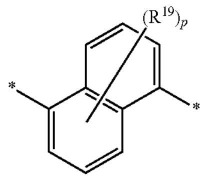

[Formula L-7]

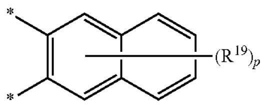

[Formula L-8]

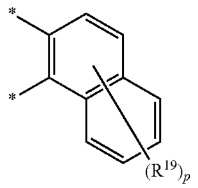

[Formula L-9]

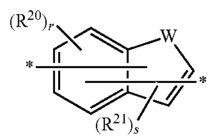

[Formula L-10]

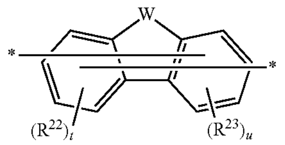

[Formula L-11]

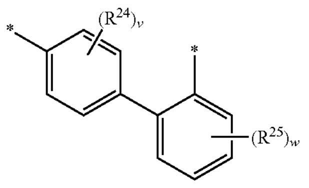

[Formula L-12]

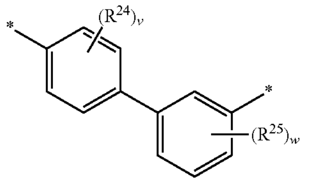

[Formula L-13]

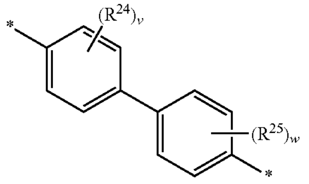

-continued

[Formula L-14]

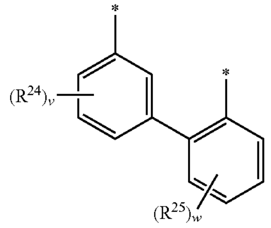

[Formula L-15]

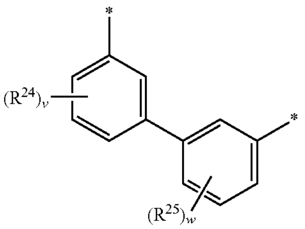

[Formula L-16]

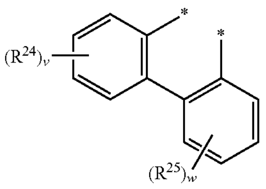

wherein, each symbol may be defined as follows.

1) W is O, S, $C(R^{26})(R^{27})$ or $N(Ar^{12})$,

2) $R^{18}$, $R^{19}$, $R^{20}$, $R^{21}$, $R^{22}$, $R^{23}$, $R^{24}$, $R^{25}$, $R^{26}$ and $R^{27}$ are the same as the definition of $R^{10}$, or adjacent groups may be bonded to each other to form a ring, 3) $Ar^{12}$ is an $C_6$-$C_{60}$ aryl group; or a $C_2$-$C_{60}$ heterocyclic group including at least one heteroatom of O, N, S, Si or P;

When $Ar^{12}$ is an aryl group, it may be preferably a $C_6$-$C_{30}$ aryl group, and more preferably a $C_6$-$C_{25}$ aryl group, for example, it may be phenyl, biphenyl, terphenyl, naphthalene, etc., When $Ar^{12}$ is a heterocyclic group, it may be preferably a $C_2$~$C_{30}$ heterocyclic group, and more preferably a $C_2$~$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc., 4) o, r, t, u, v and w are each independently an integer of 0 to 4, p is an integer of 0 to 6, s is an integer of 0 to 2, 5) * indicates a bonding position.

The L may be represented by any one of Formulas L-17 to Formulas L-21.

[Formula L-17]

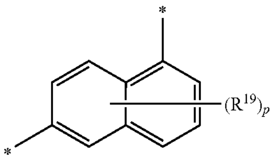

-continued

[Formula L-18]

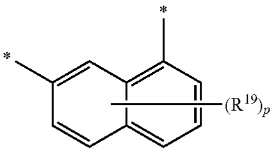

[Formula L-19]

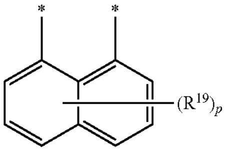

[Formula L-20]

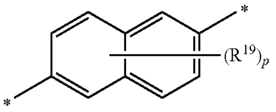

[Formula L-21]

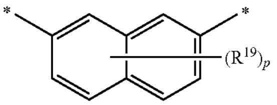

In Formula L-17 to Formula L-21, $R^{19}$, p and *are the same as defined above.

Also, $Ar^{10}$ is represented by any of Formulas Ar-1 to Ar-15.

[Formula Ar-1]

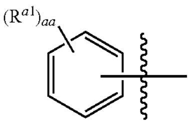

[Formula Ar-2]

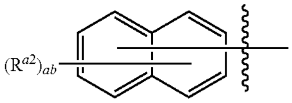

[Formula Ar-3]

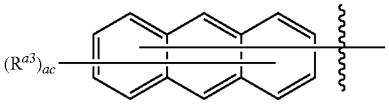

[Formula Ar-4]

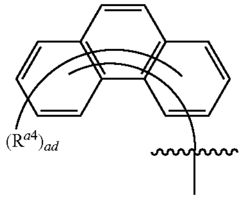

[Formula Ar-5]

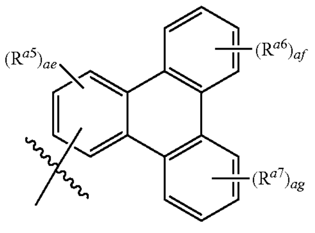

-continued

[Formula Ar-6]

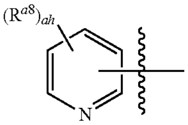

[Formula Ar-7]

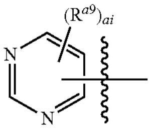

[Formula Ar-8]

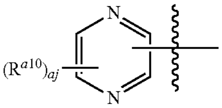

[Formula Ar-9]

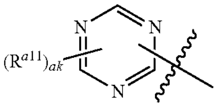

[Formula Ar-10]

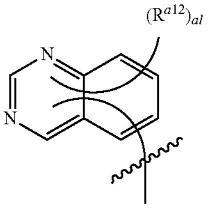

[Formula Ar-11]

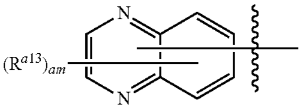

[Formula Ar-12]

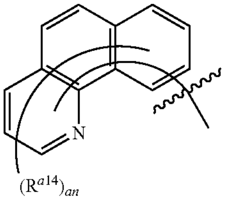

[Formula Ar-13]

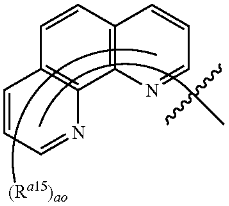

[Formula Ar-14]

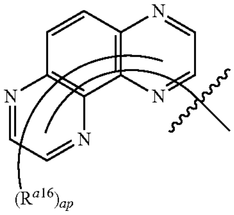

-continued

[Formula Ar-15]

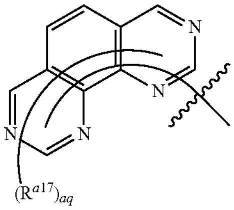

Wherein,

1) $R^{a1}$, $R^{a2}$, $R^{a3}$, $R^{a4}$, $R^{a5}$, $R^{a6}$, $R^{a7}$, $R^{a8}$, $R^{a9}$, $R^{a10}$, $R^{a11}$, $R^{a12}$, $R^{a13}$, $R^{a14}$, $R^{a15}$, $R^{a16}$ and $R^{a17}$ are the same as the definition of $R^{10}$, or adjacent groups may be bonded to each other to form a ring, 2) aa, al, am, ap and aq are each independently an integer of 0 to 5, ab and ao are each independently an integer of 0 to 7, ac and ad are each independently an integer of 0 to 9, ae, ai, and aj are each independently an integer of 0 to 3, af, ag and ah are each independently an integer of 0 to 4, ak is an integer of 0 to 2, an is an integer of 0 to 8, 3)  indicates a bonding position.

Specifically, the compound of Formula 2 may be any one of the following compounds N-1 to N-92, but is not limited thereto.

N-1

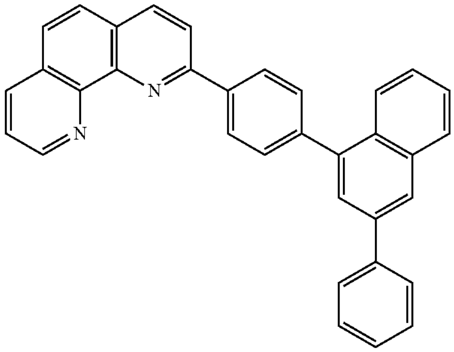

N-2

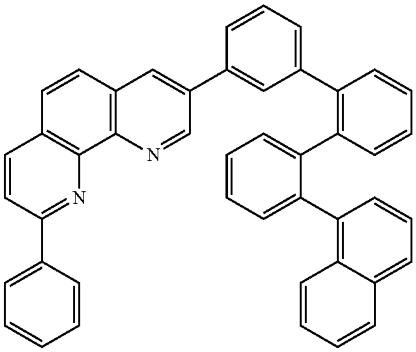

-continued
N-3
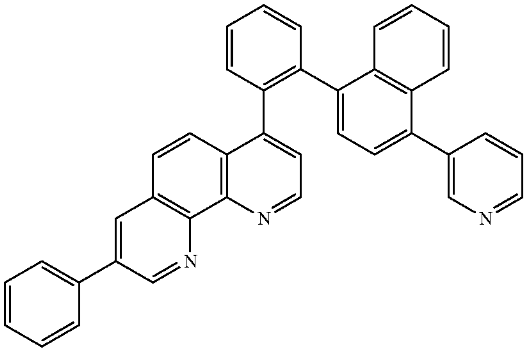
N-4
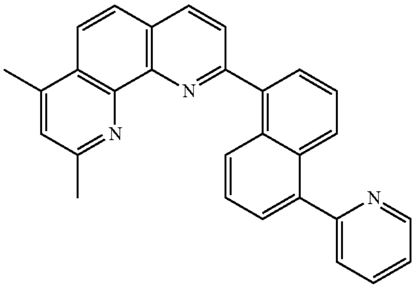
N-5
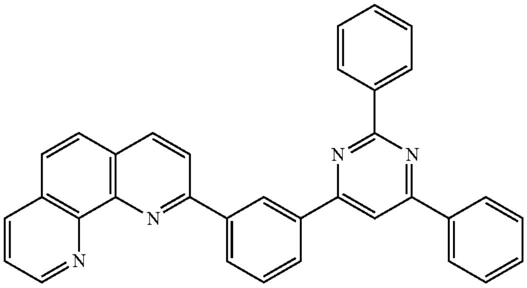
N-6
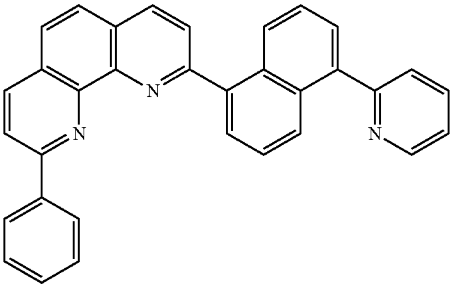
N-7
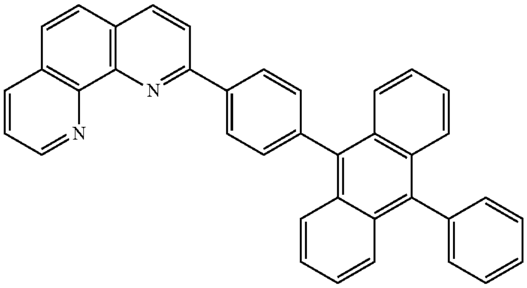
-continued
N-8
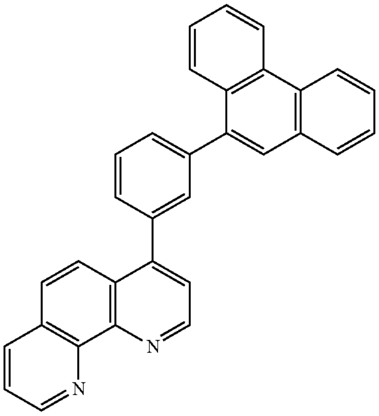
N-9
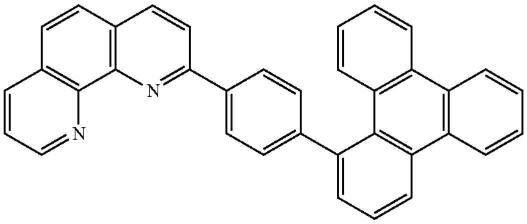
N-10
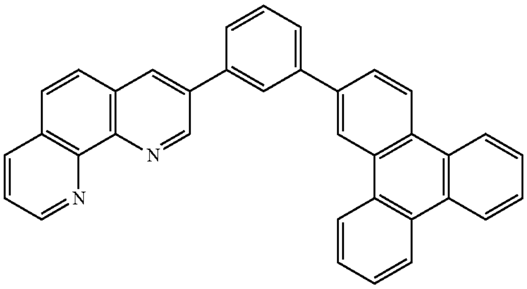
N-11
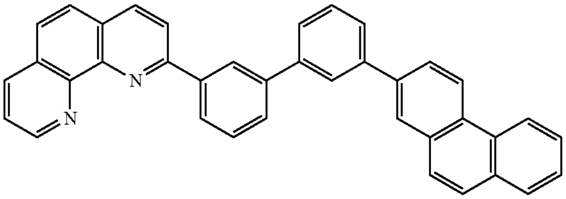
N-12
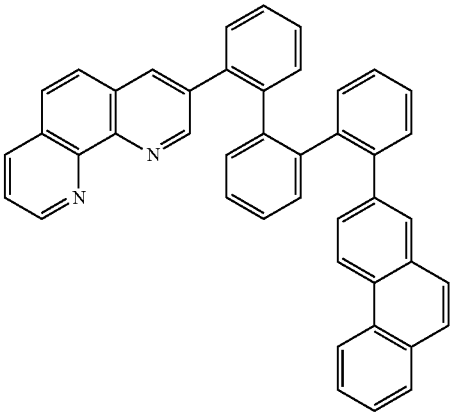

-continued
N-13
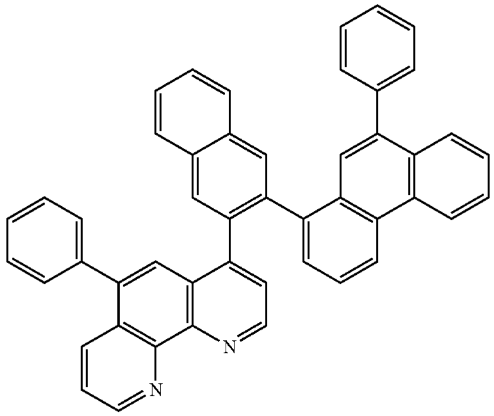
N-14
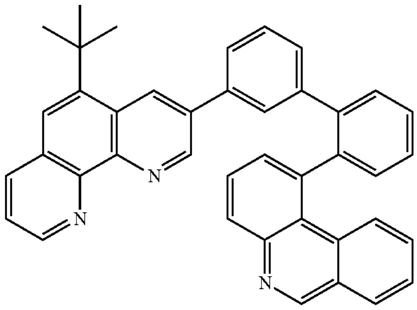
N-15
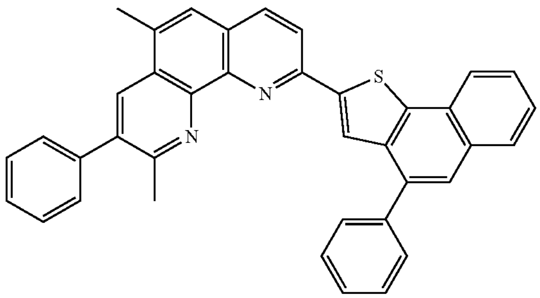
N-16
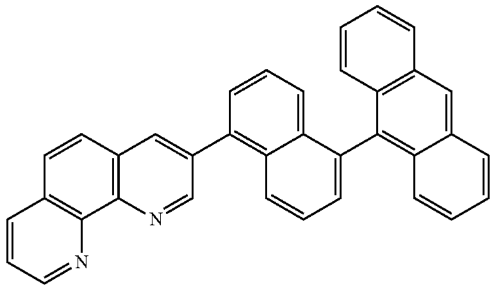
-continued
N-17
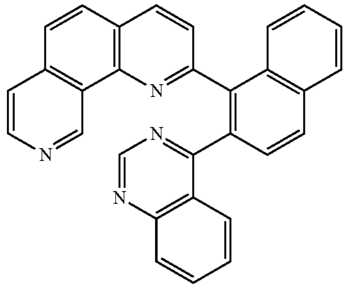
N-18
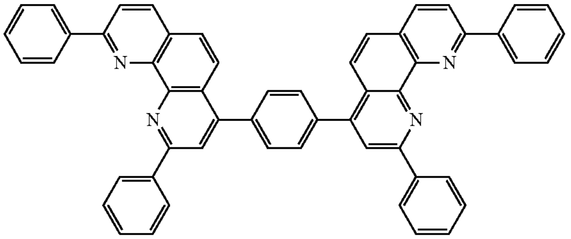
N-19
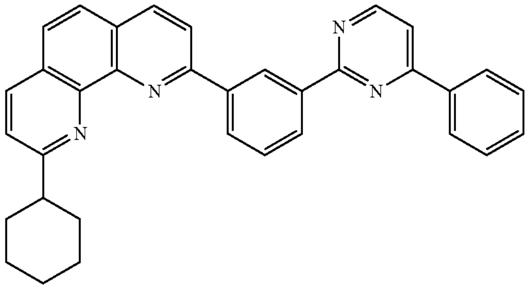
N-20
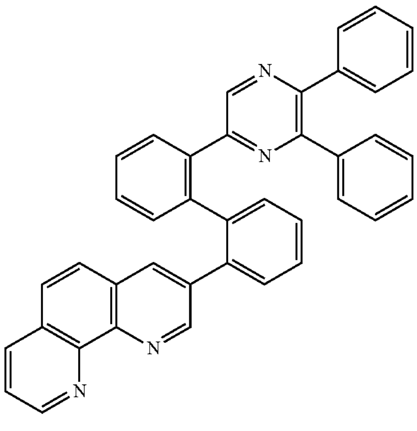

-continued
N-21
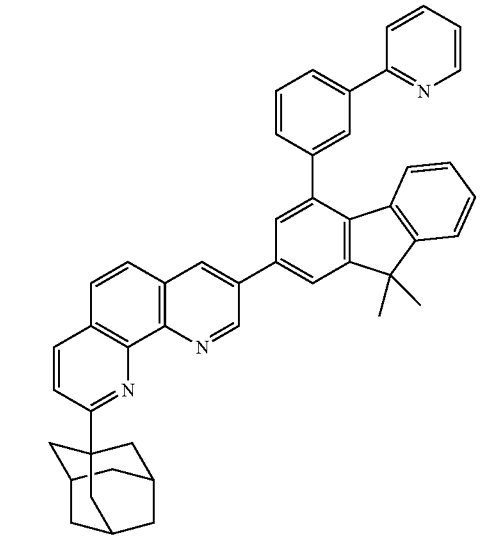
N-22
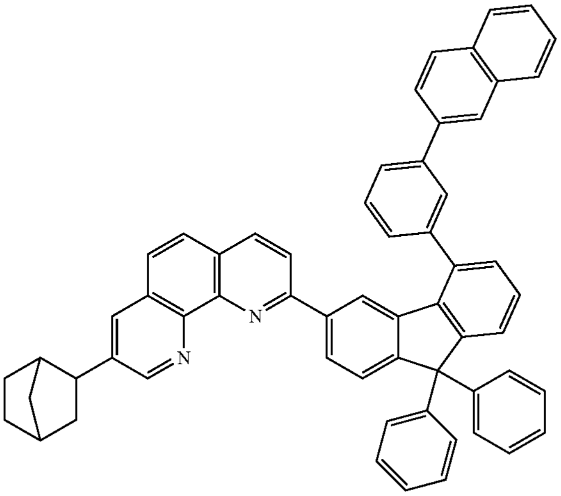
N-23
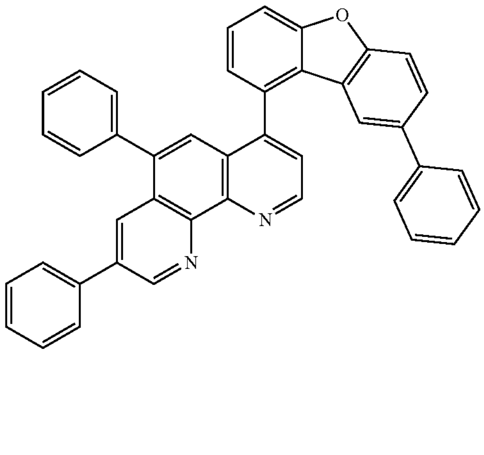
-continued
N-24
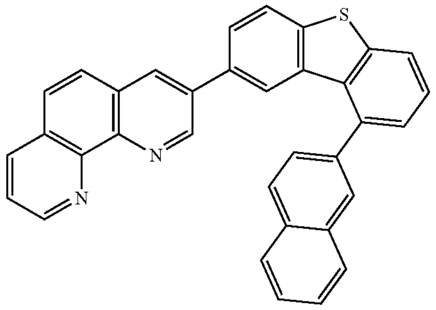
N-25
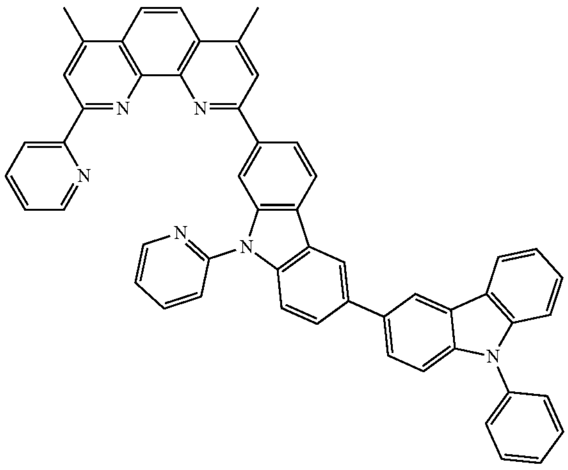
N-26
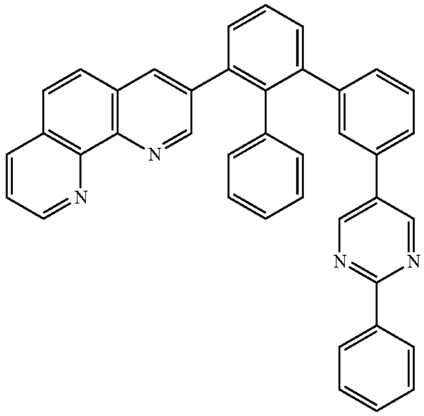

-continued
N-27
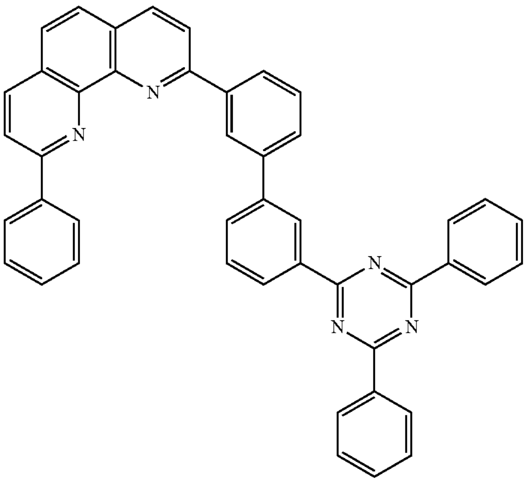
N-28
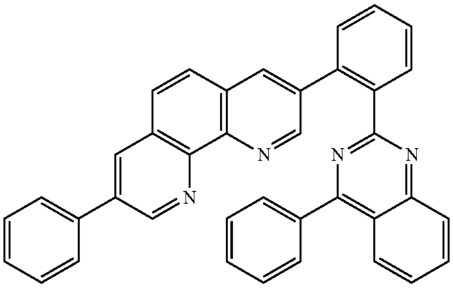
N-29
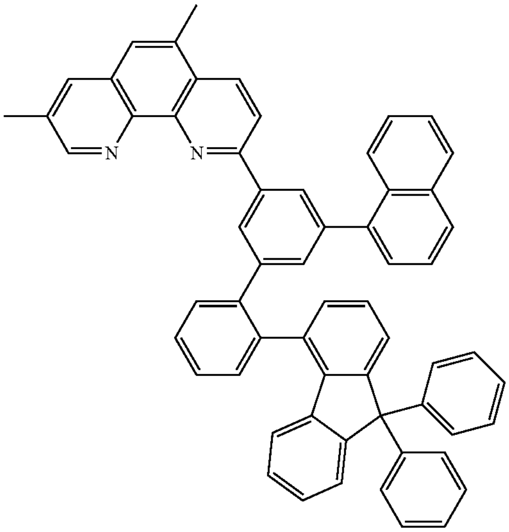
-continued
N-30
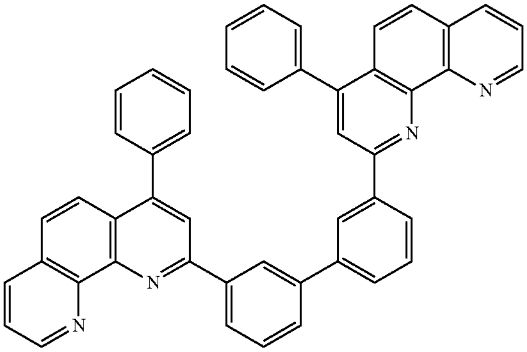
N-31
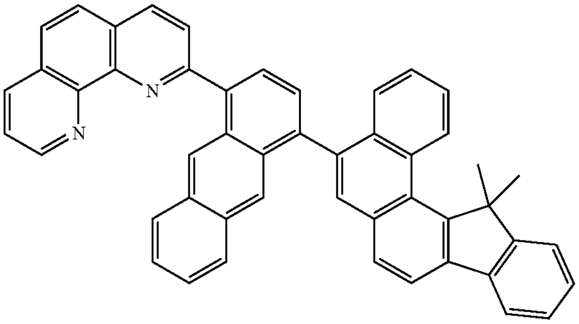
N-32
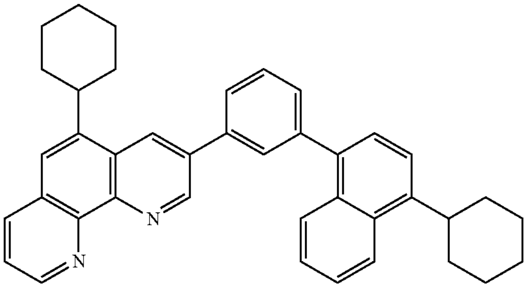
N-33
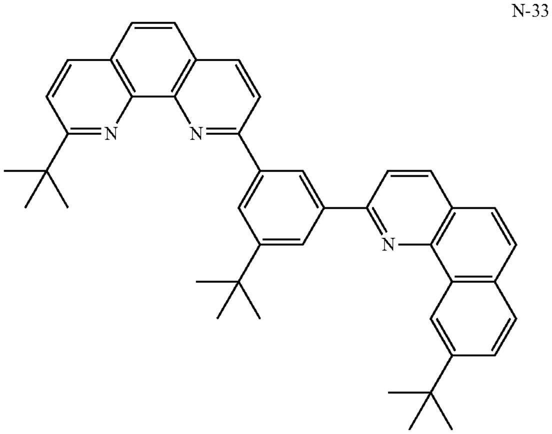

N-34
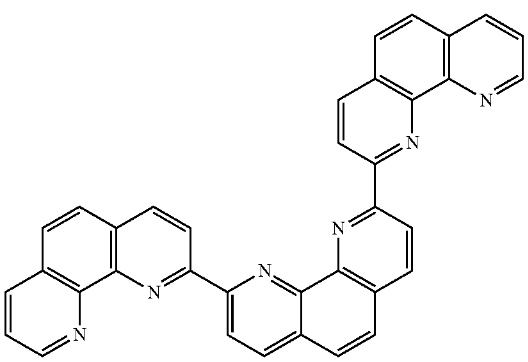
N-35
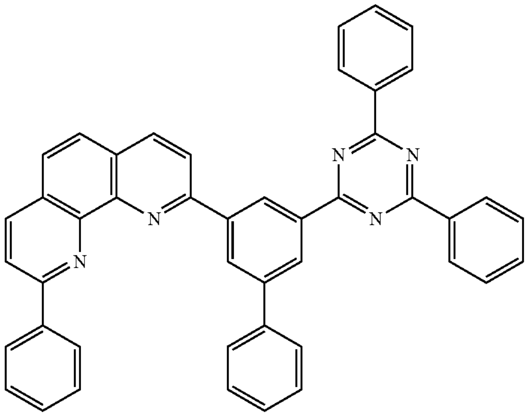
N-36
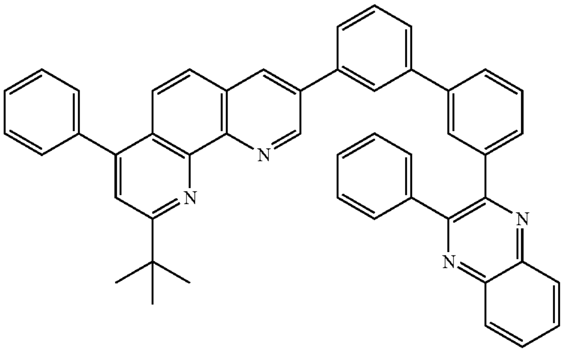
N-37
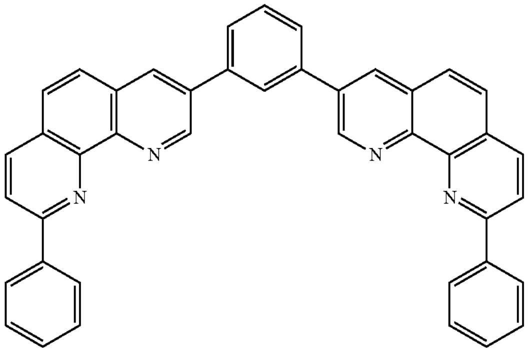
N-38
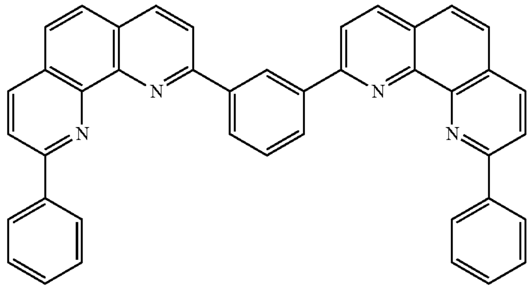
N-39
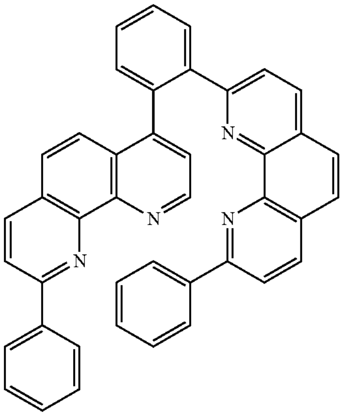
N-40
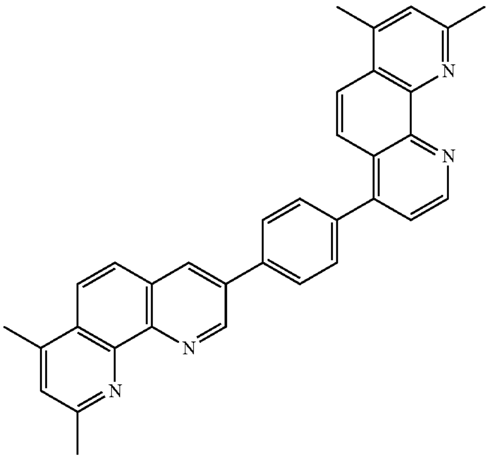
N-41
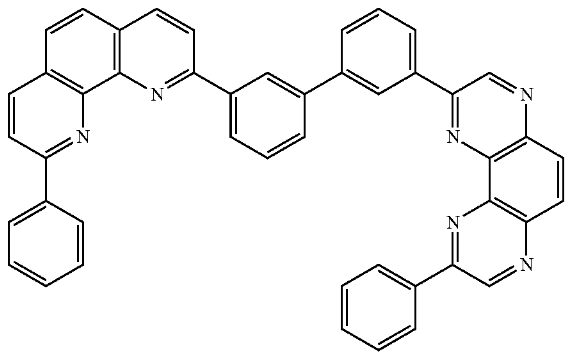

-continued
N-42
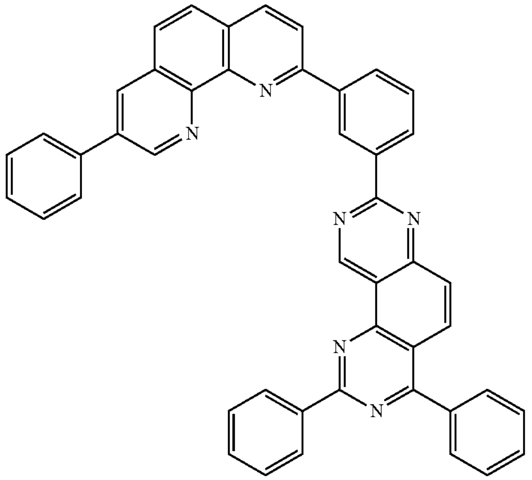
N-43
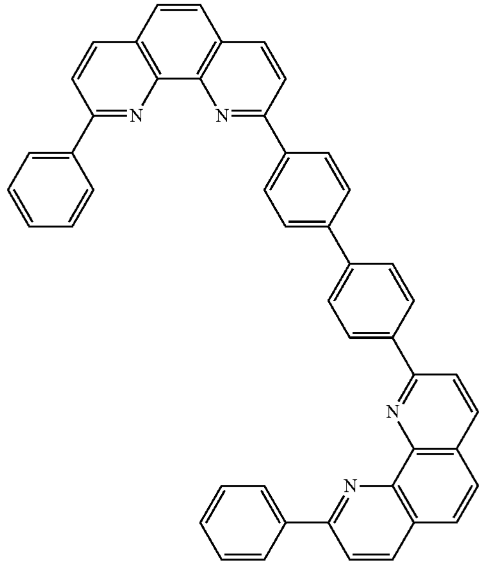
N-44
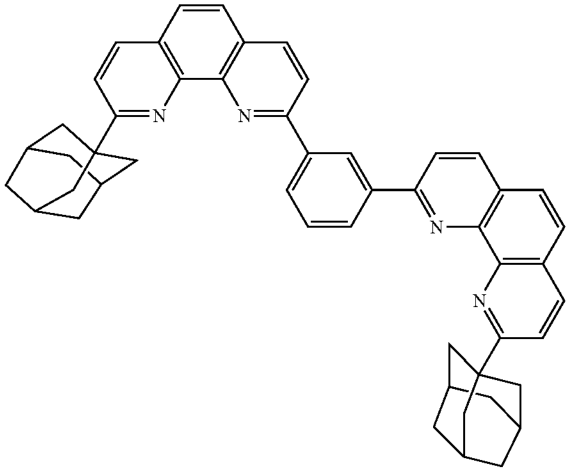
-continued
N-45
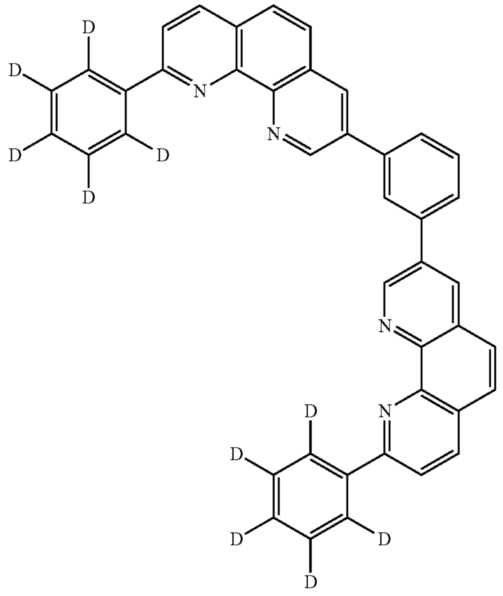
N-46
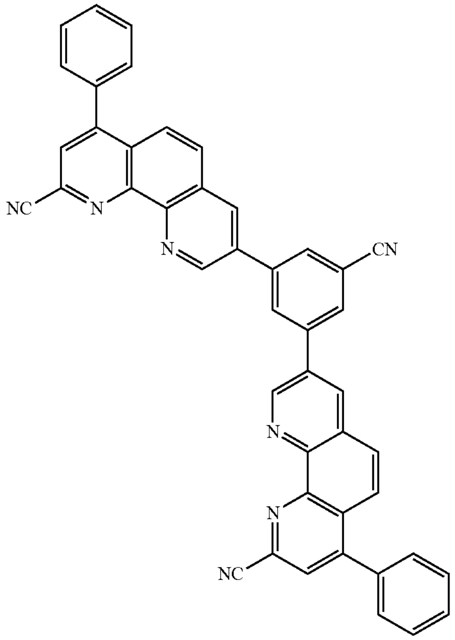

N-47
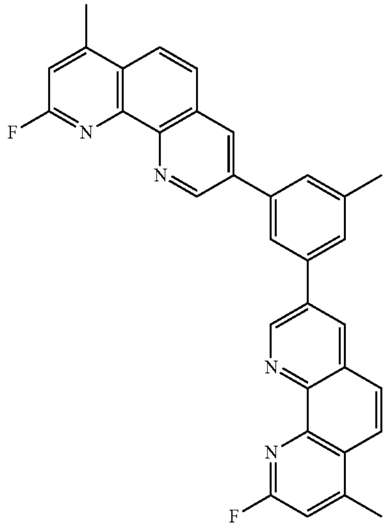
N-48
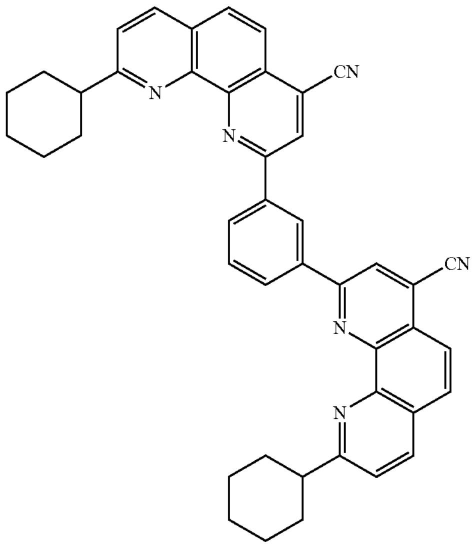
N-49
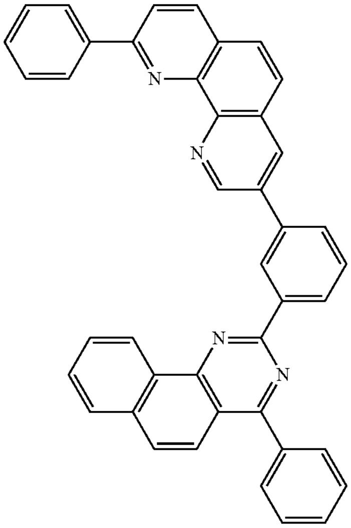
N-50
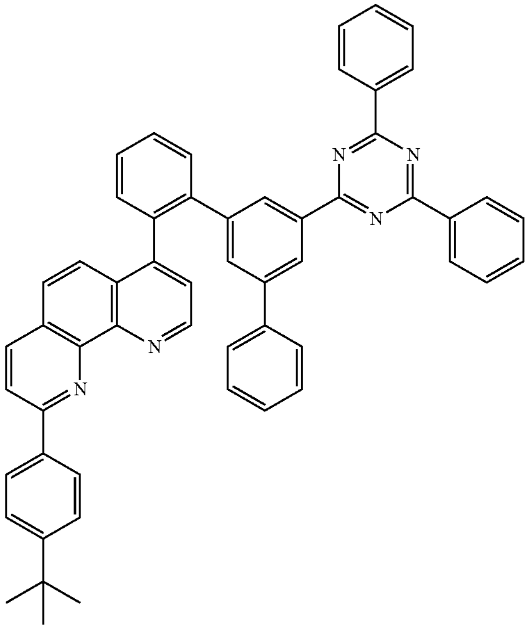
N-51
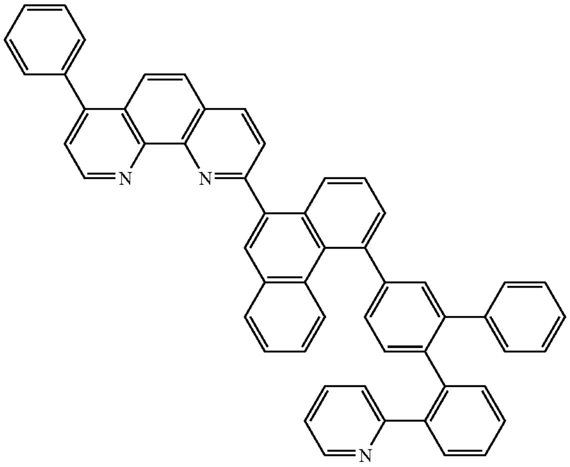
N-52
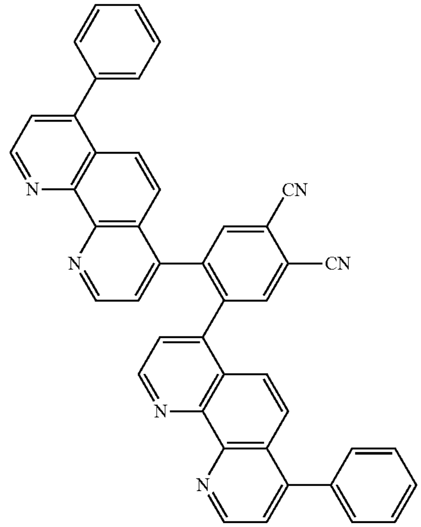

-continued
N-53
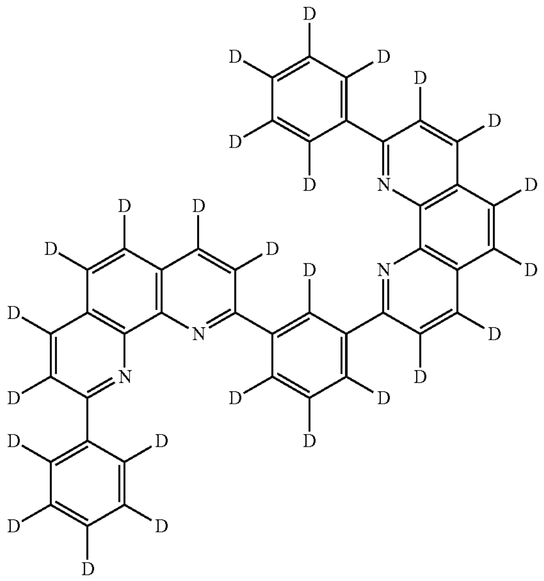
N-54
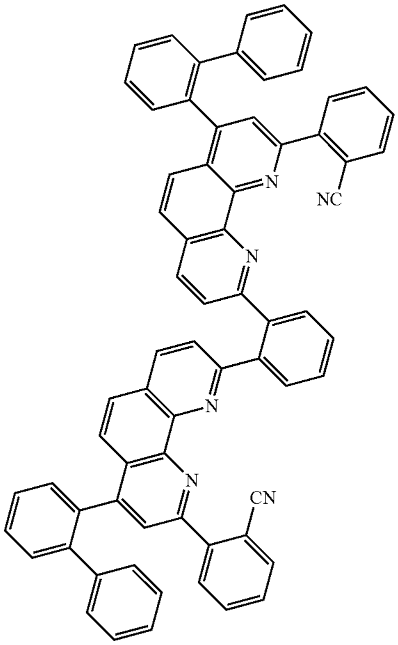
-continued
N-55
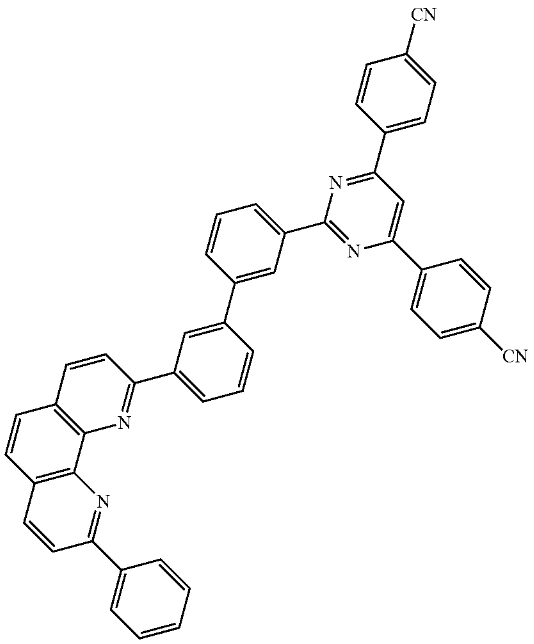
N-56
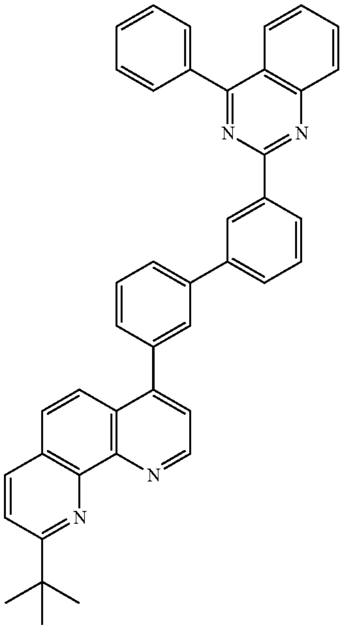

-continued
N-57
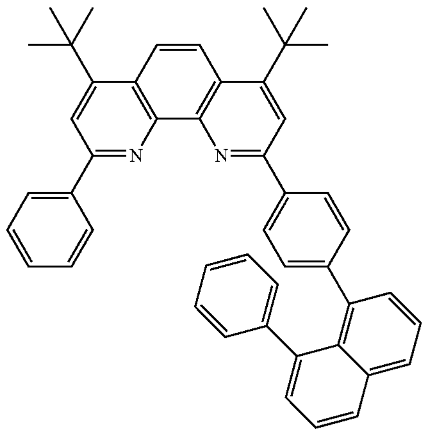
N-58
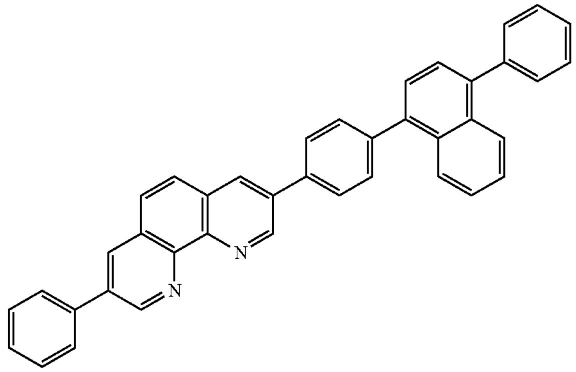
N-59
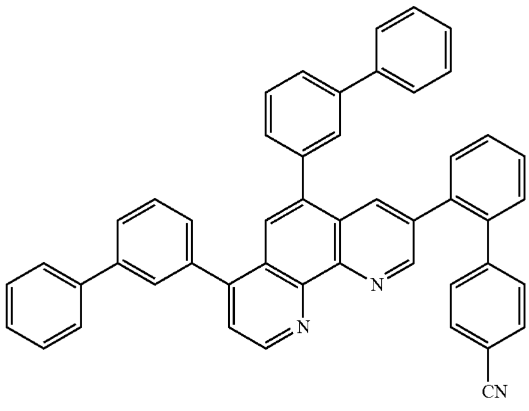
-continued
N-60
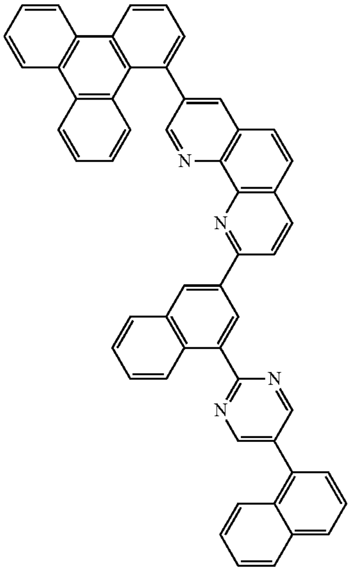
N-61
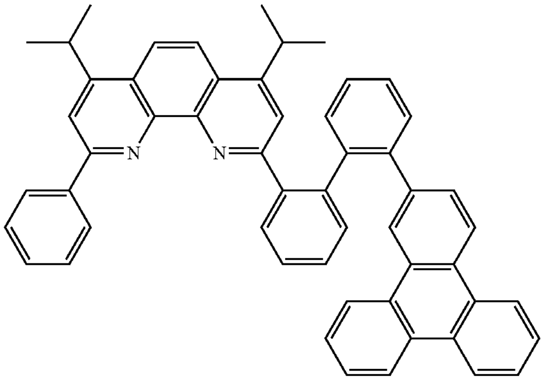
N-62
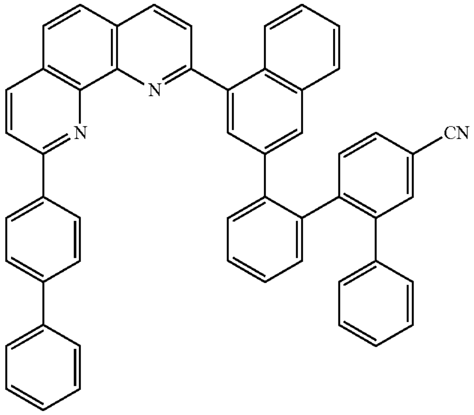

-continued
N-63
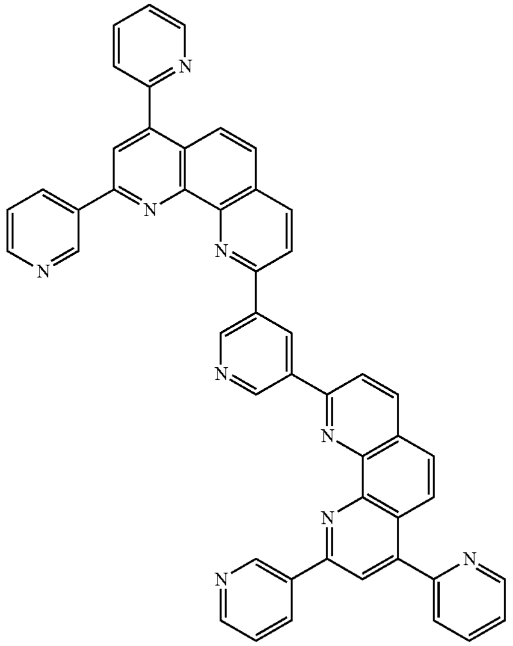
N-64
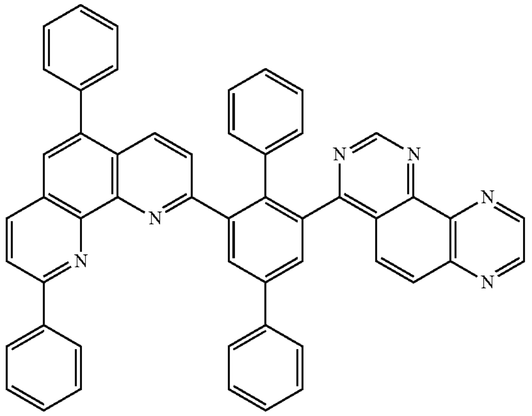
-continued
N-65
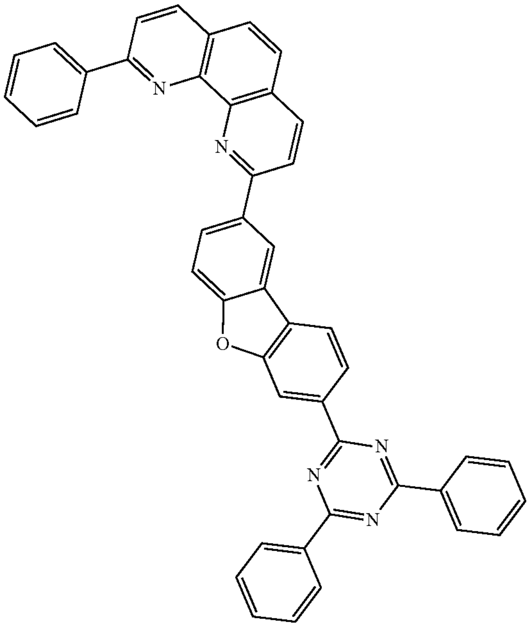
N-66
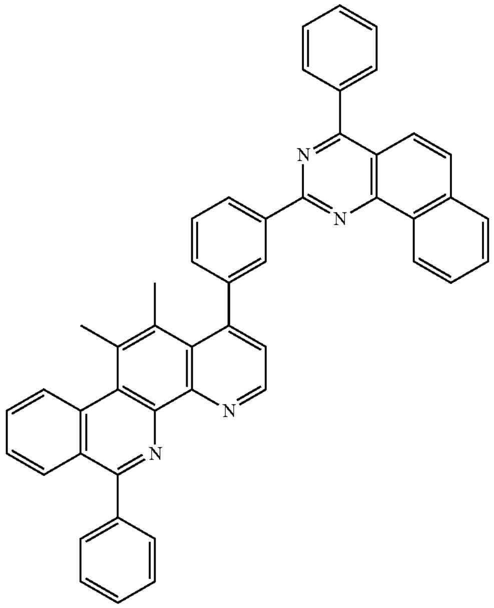

N-67
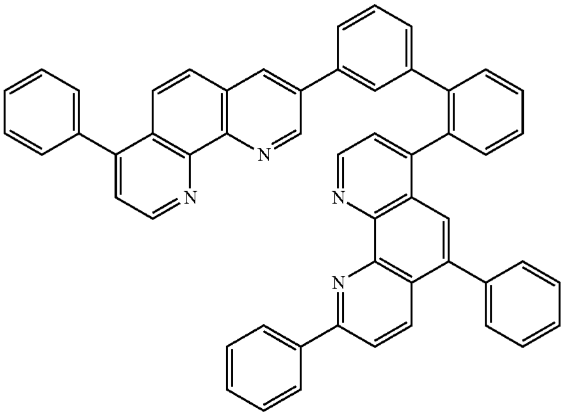
N-68
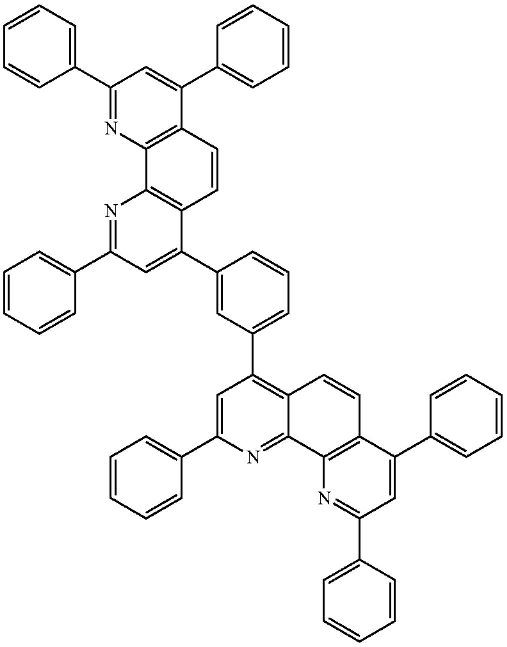
N-69
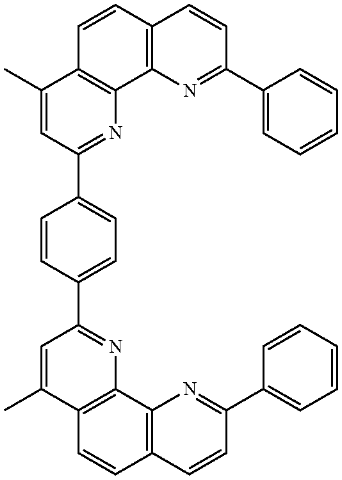
-continued
N-70
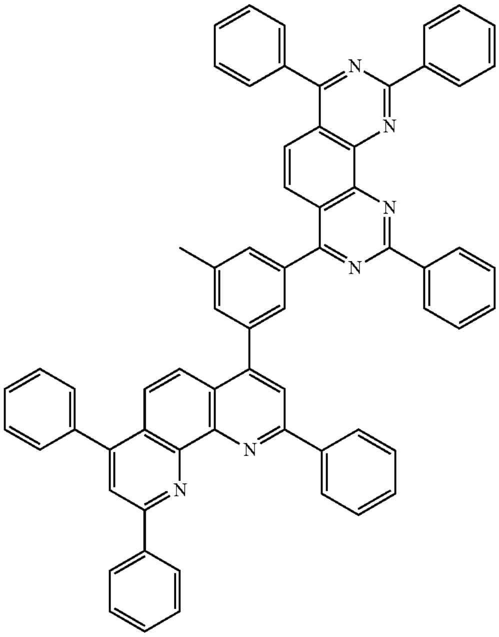
N-71
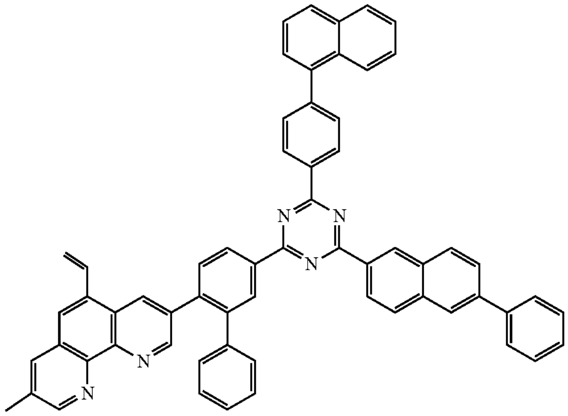
N-72
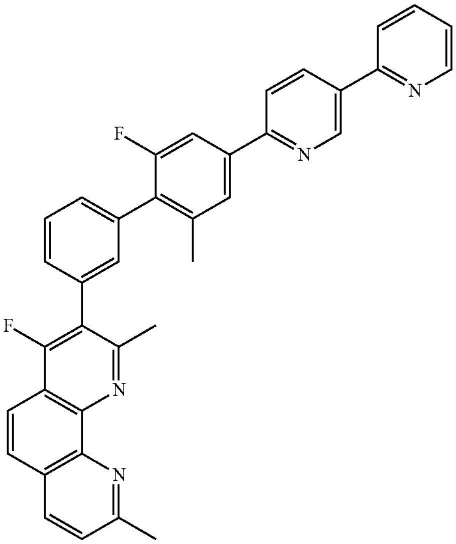

N-73
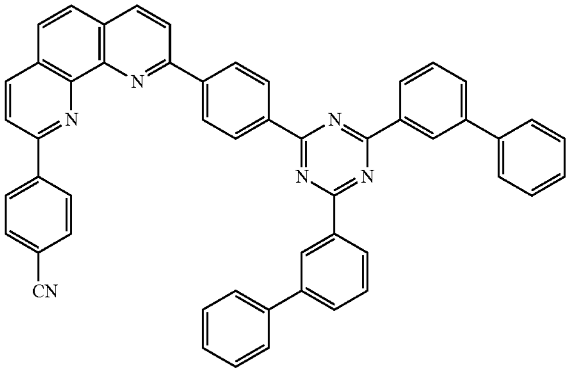
N-74
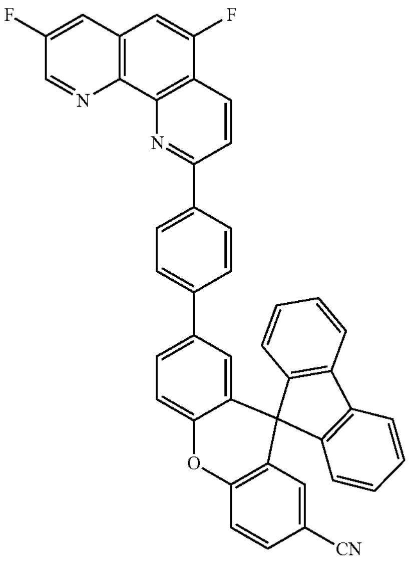
N-75
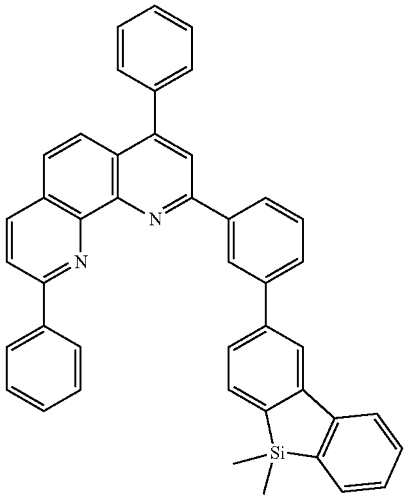
N-76
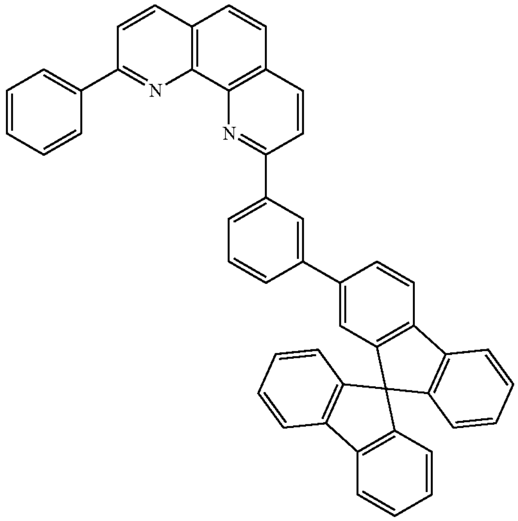
N-77
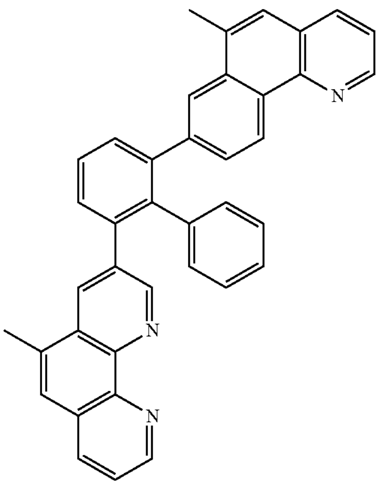

-continued
N-78
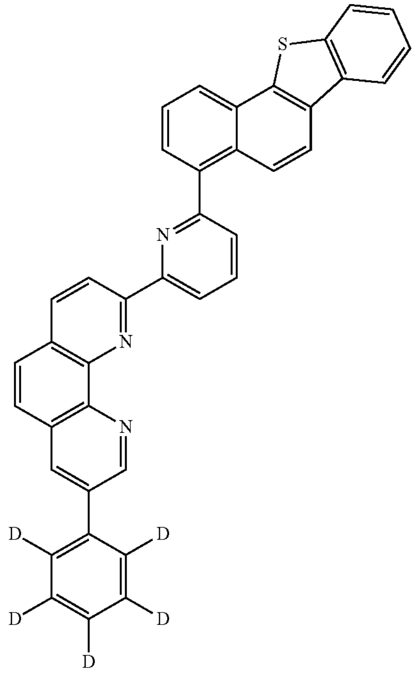
N-79
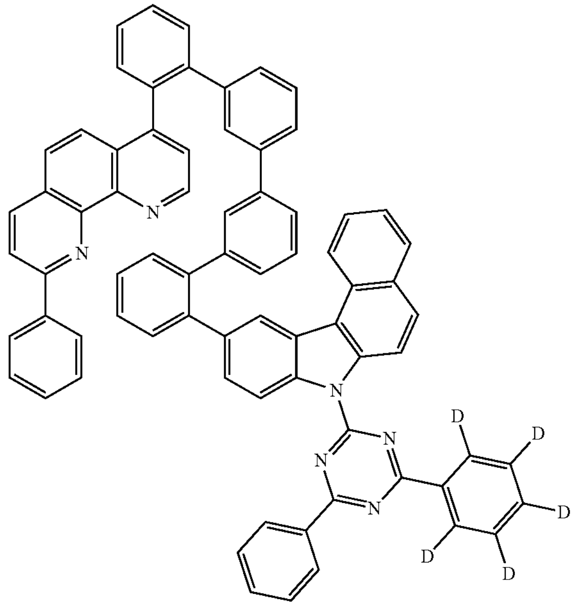
-continued
N-80
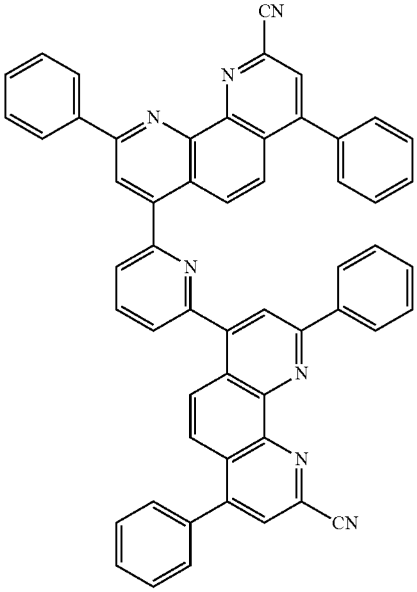
N-81
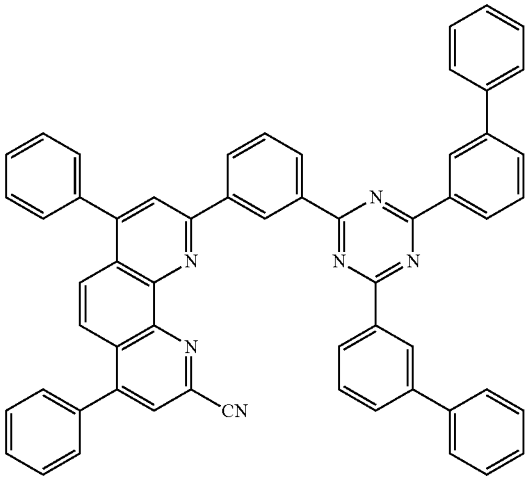
N-82
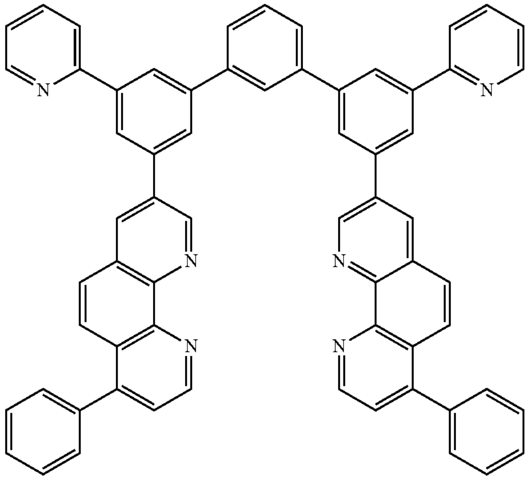

-continued
N-83
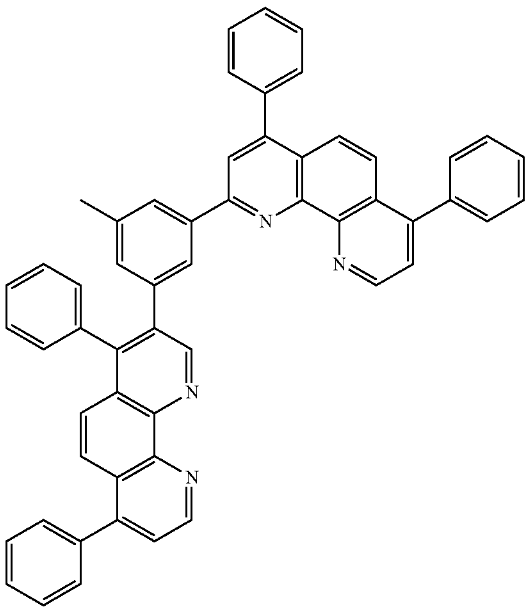
N-84
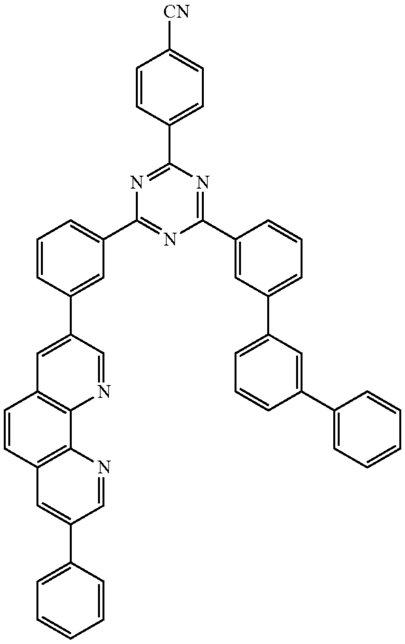
-continued
N-85
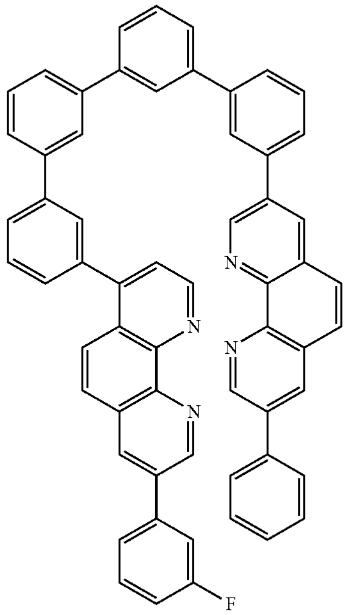
N-86
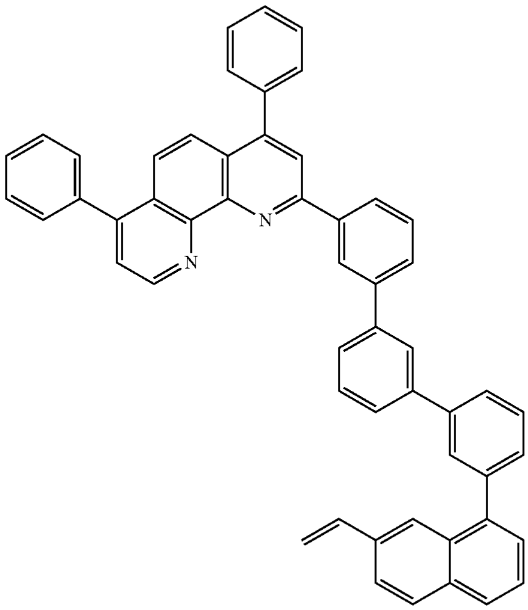

-continued
N-87
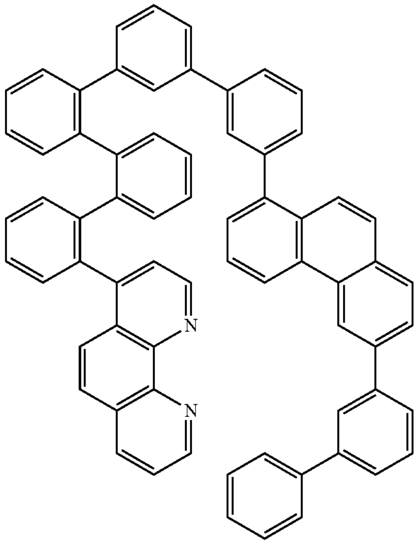
N-88
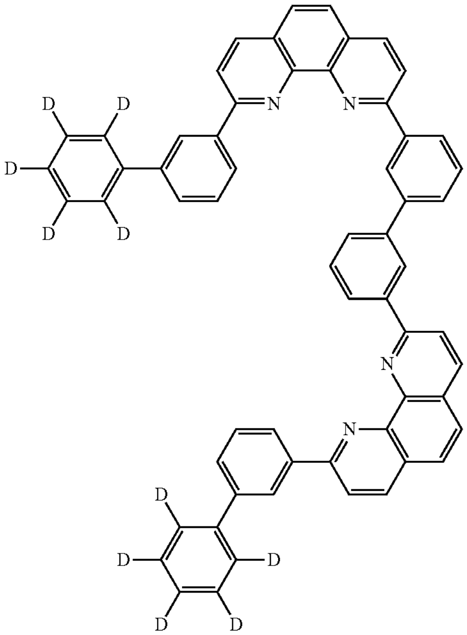
-continued
N-89
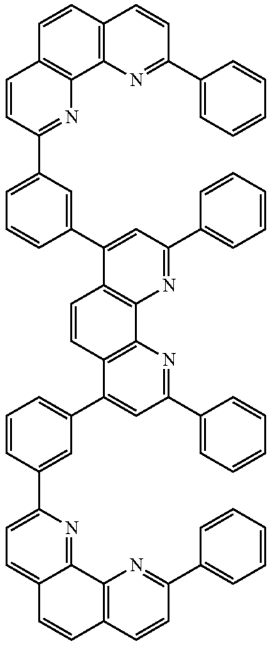
N-90
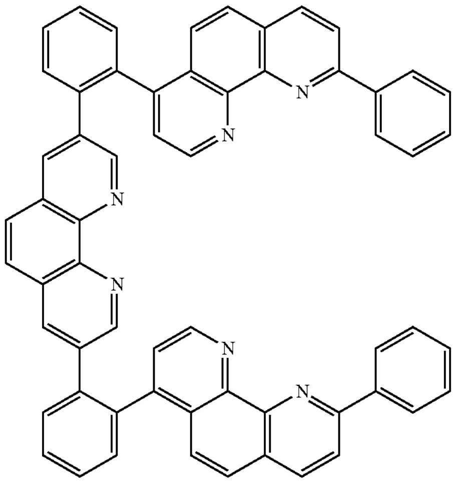

-continued

N-91

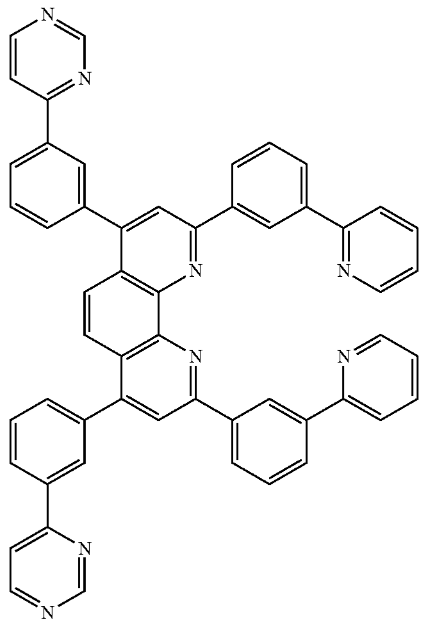

N-92

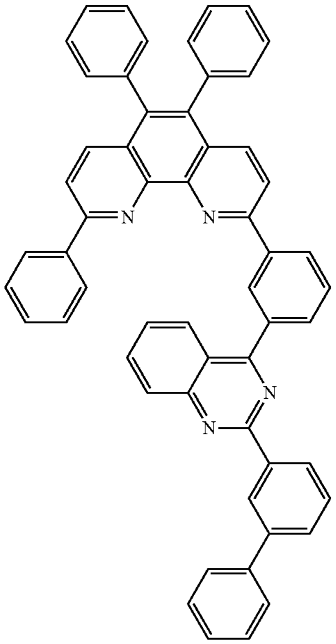

The n-type charge generation layer may be doped with a metal, metal fluoride or metal oxide selected from the group consisting of silver (Ag), magnesium (Mg), aluminum (Al), ytterbium (Yb), copper (Cu), zinc (Zn), cadmium (Cd), gold (Au), nickel (Ni), cobalt (Co), iron (Fe), molybdenum (Mo), niobium (Nb), palladium (Pd), platinum (Pt), lithium (Li), cesium (Cs), calcium (Ca), lithium fluoride (LiF), cesium fluoride (CsF), calcium fluoride ($CaF_2$) and lithium oxide (LiOx), wherein the metal, metal fluoride or metal oxide may be doped with 0.1 w% to 10 w%, preferably 0.5 w% to 5 w%.

Also, the organic electronic element according to the present invention further comprises a light efficiency enhancing layer formed on at least one surface of the first electrode and the second electrode, the surface being opposite to the organic material layer.

In another aspect, the present invention provides an electronic device comprising a display device comprising the organic electronic element; and a control unit for driving the display device. In this case, the organic electronic element is at least one of an organic electroluminescent device, an organic solar cell, an organic photo conductor (OPC), an organic transistor (organic TFT), and a device for monochromatic or white lighting. At this time, the electronic device may be a current or future wired/wireless communication terminal, and covers all kinds of electronic devices including mobile communication terminals such as mobile phones, a personal digital assistant(PDA), an electronic dictionary, a point-to-multipoint (PMP), a remote controller, a navigation unit, a game player, various kinds of TVs, and various kinds of computers.

Also, in another aspect, the present invention provides a compound represented by any one of the following formulas P-1 to P-16.

P-1

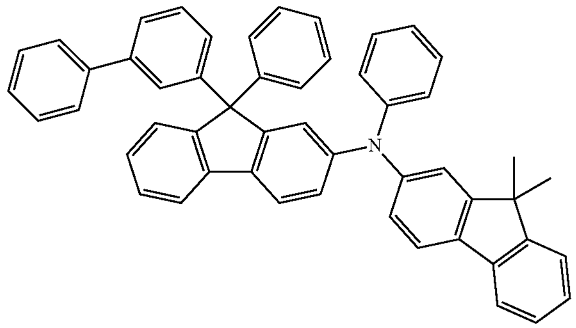

P-2

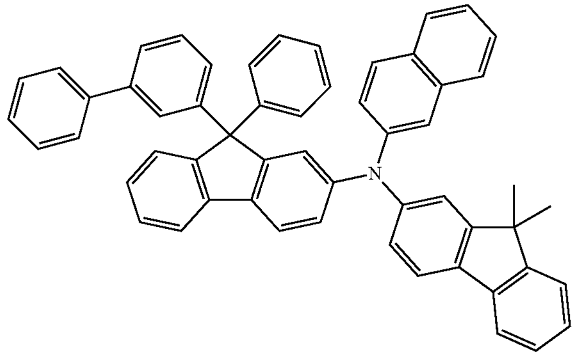

P-3

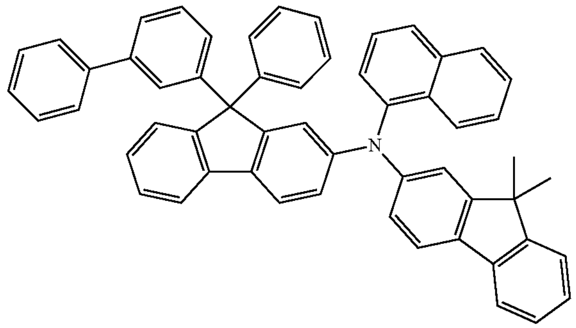

-continued
P-4
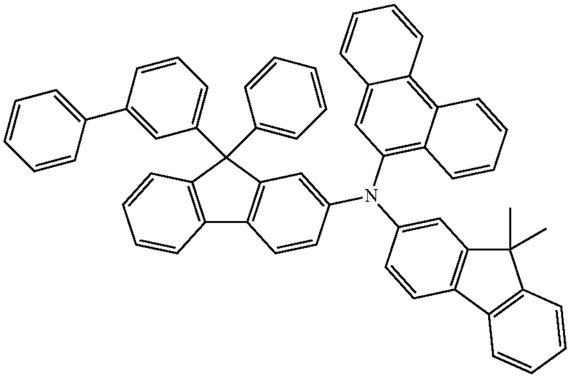
P-5
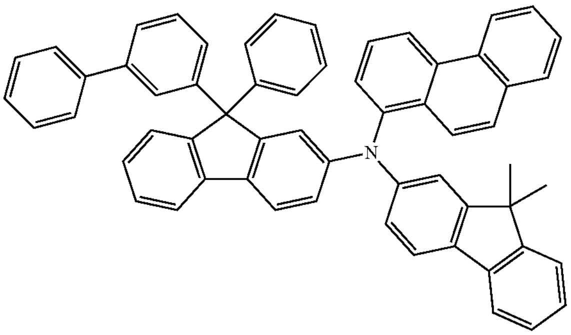
P-6
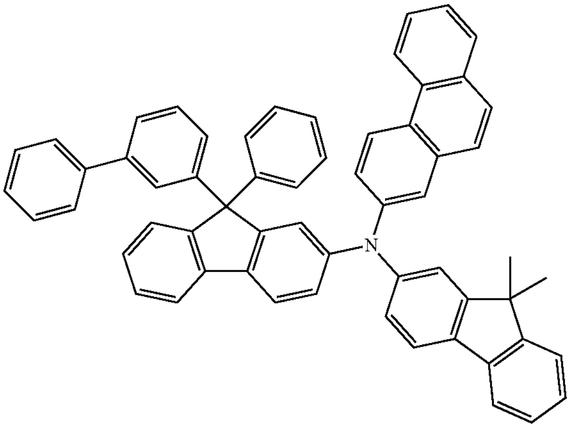
P-7
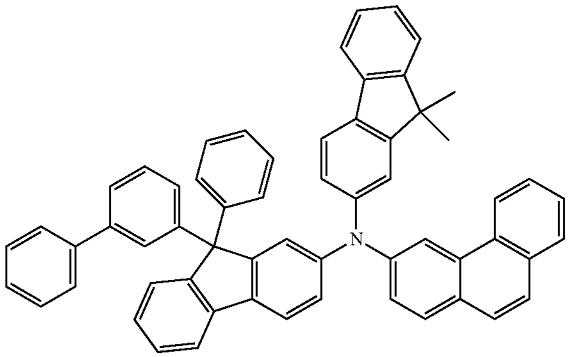
-continued
P-8
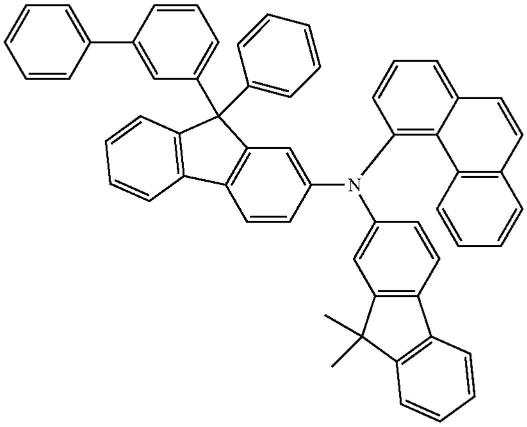
P-9
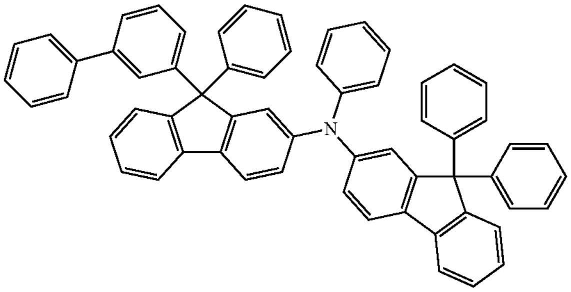
P-10
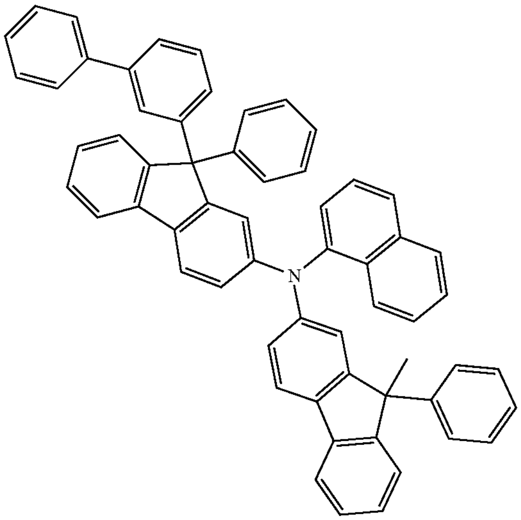

-continued
P-11
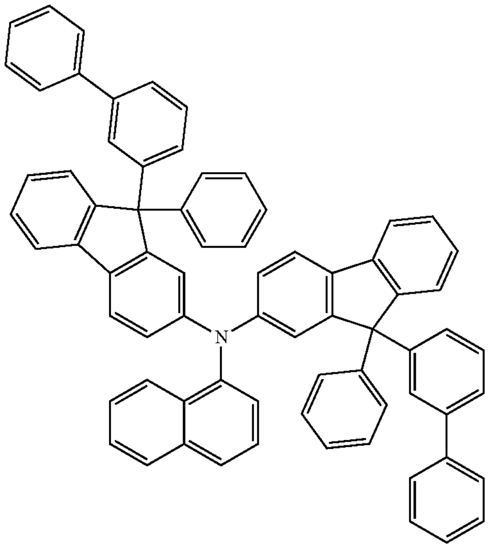
P-12
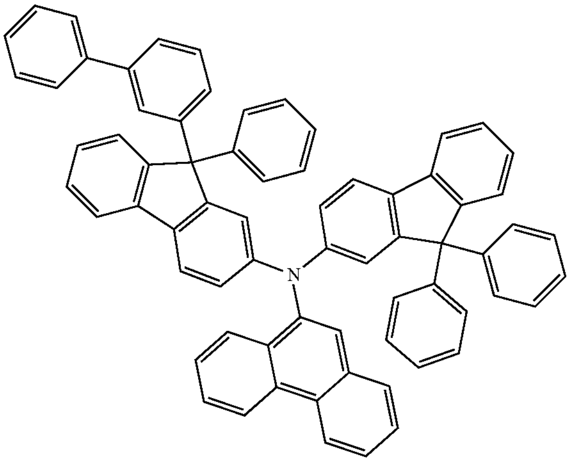
P-13
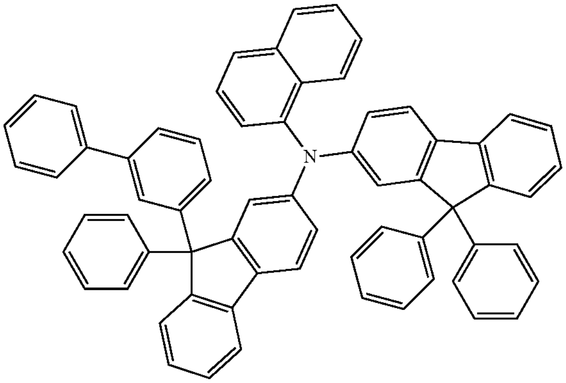
-continued
P-14
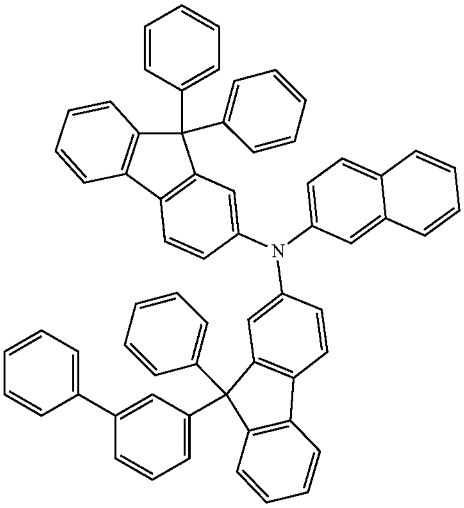
P-15
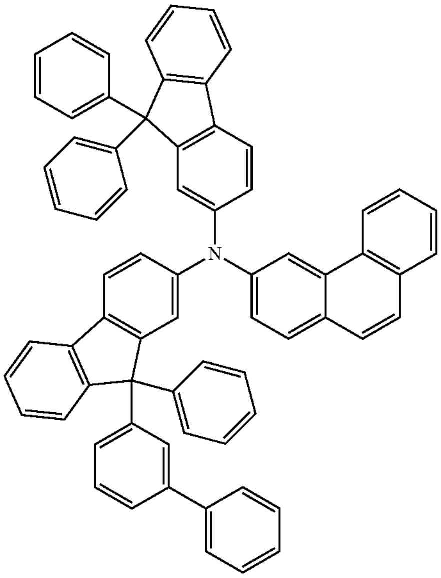
P-16
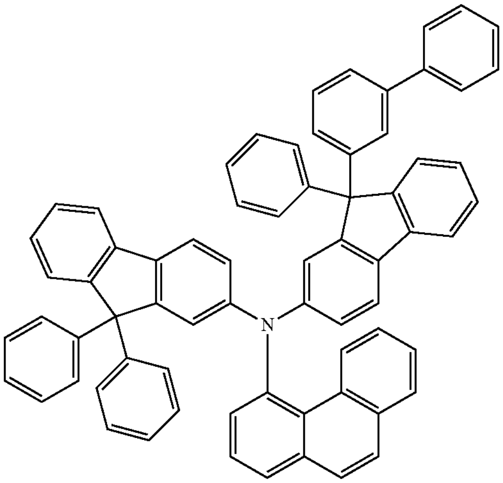
In another aspect, the present invention provides an organic electronic element comprising a compound represented by any one of Formulas P-1 to P-16.

Figure 2:
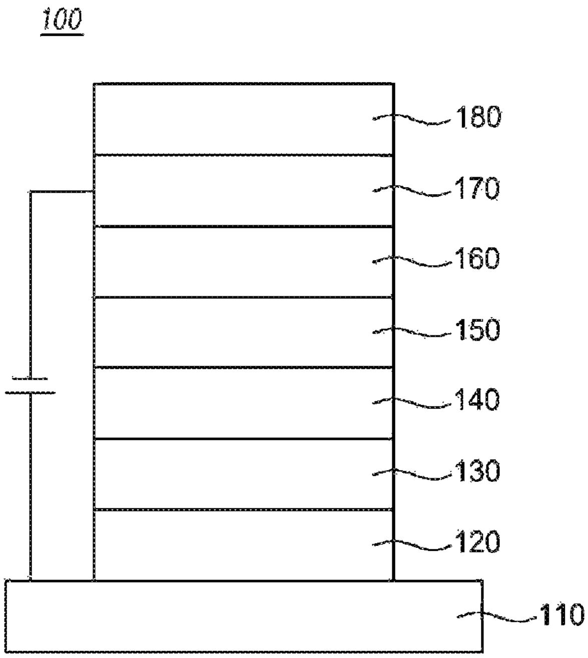

Referring to FIG. 2, the organic electronic element (100) according to the present invention comprises a first electrode (110), a second electrode (170), an organic material layer comprising a single compound or 2 or more compounds represented by Formulas P-1 to P-16 between the first electrode (110) and the second electrode (170). In this case, the first electrode (110) may be an anode, the second electrode (170) may be a cathode, and in the case of an invert type, the first electrode may be a cathode and the second electrode may be an anode.

Figure 3:
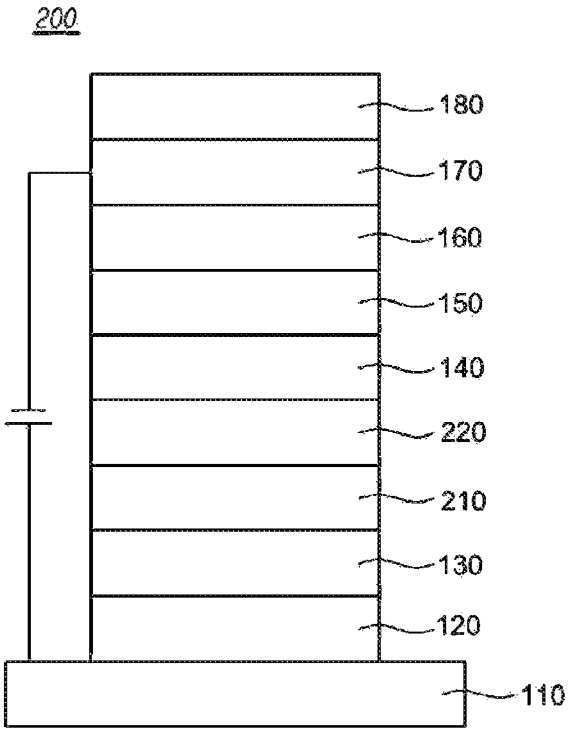

The organic material layer may sequentially comprise a hole injection layer (120), a hole transport layer (130), an emitting layer (140), an electron transport layer (150), and an electron injection layer (160) on the first electrode (110). In this case, the remaining layers except for the emitting layer (140) may not be formed. It may further include a hole blocking layer, an electron blocking layer, an emitting-auxiliary layer (220), a buffer layer (210), etc. and the electron transport layer (150) and the like may serve as a hole blocking layer. (See FIG. 3)

Also, the organic electronic element according to an embodiment of the present invention may further comprise a protective layer or a light efficiency enhancing layer (180). The light efficiency enhancing layer may be formed on one of both surfaces of the first electrode, the surface not in contact with the organic material layer or on one of both surfaces of the second electrode, the surface not in contact with the organic material layer.

The compound represented by any one of Formulas P-1 to P-16 according to the present invention applied to the organic material layer may be used as a material for the hole injection layer (120), the hole transport layer (130), the emitting-auxiliary layer (220), electron transport auxiliary layer, the electron transport layer (150), and an electron injection layer (160), a host or dopant of the emitting layer (140) or the light efficiency enhancing layer. Preferably, for example, the compound represented by any one of Formulas P-1 to P-16 of the present invention may be used as a material for the hole transport layer.

Otherwise, even with the same core, the band gap, electrical characteristics, interface characteristics, etc. may vary depending on which position the substituent is bonded to, therefore the choice of core and the combination of sub-substituents bound thereto are also very important, and in particular, when the optimal combination of energy levels and T1 values and unique properties of materials(mobility, interfacial characteristics, etc.) of each organic material layer is achieved, a long lifespan and high efficiency can be achieved at the same time.

As another specific example, the present invention provides an organic electronic element characterized in that a compound of the same type or a different type of the compound represented by any one of Formulas P-1 to P-16 is mixed and used in the organic material layer.

Also, the present invention provides an electronic device comprising a display device including the organic electric element comprising the compound represented by any one of Formulas P-1 to P-16; and a control unit for driving the display device;

In another aspect, the present invention provides a method for reusing the compound comprising:

the step of depositing an organic light emitting material comprising a compound represented by any one of Formulas P-1 to P-16 in a manufacturing process of an organic light emitting device;

the step of removing impurities from the crude organic light emitting material recovered from the deposition apparatus;

the step of recovering the removed impurities; and the step of purifying the recovered impurities to a purity of 99.9% or higher;

The step of removing impurities from the crude organic light emitting material recovered from the deposition tool may preferably comprise performing a preliminary purification process to obtain a purity of 98% or more by recrystallization in a recrystallization solvent.

The recrystallization solvent may preferably be a polar solvent having a polarity index (PI) of 5.5 to 7.2.

The recrystallization solvent may preferably be used by mixing a polar solvent having a polarity index of 5.5 to 7.2 and a non-polar solvent having a polarity index of 2.0 to 4.7.

When a mixture of a polar solvent and a non-polar solvent is used for the recrystallization solvent, the non-polar solvent may be used in an amount of 15% (v/v) or less relative to the polar solvent.

The recrystallization solvent may be preferably used by mixing N-Methylpyrrolidone (NMP) single solvent; or a mixed polar solvent in which any one selected from the group consisting of 1,3-Dimethyl-2-imidazolidinone, 2-Pyrrolidone, N,N-Dimethyl formamide, Dimethyl acetamide and Dimethyl sulfoxide are mixed to N-Methylpyrrolidone (NMP); or a single; or mixed non-polar solvents; or polar solvents and non-polar solvents selected from the group consisting of Toluene, Dichloromethane (DCM), Dichloroethane (DCE), Tetrahydrofuran (THF), Chloroform, Ethyl acetate and Butanone;

The pre-refining process may comprise the step of dissolving the crude organic light emitting material recovered from the deposition device in a polar solvent at 90° C. to 120° C. and then cooling to 0° C. to 5° C. to precipitate crystals.

The pre-refining process may comprise the step of precipitating crystals after dissolving the crude organic light emitting material recovered from the deposition device in a polar solvent at 90° C. to 120° C., and then cooling to 35° C. to 40° C., and adding a non-polar solvent, and then cooling to 0° C. to 5° C.

The pre-refining process may comprise the step of precipitating crystals while removing the non-polar solvent after dissolving the crude organic light emitting material recovered from the deposition device in a non-polar solvent, concentrating the solvent.

The pre-refining process may comprise the step of recrystallizing with a non-polar solvent again after first recrystallizing with a polar solvent.

The step of purifying the recovered impurities to a purity of 99.9% or higher may comprise performing an adsorption separation process of adsorbing and removing impurities by adsorbing them to an adsorbent.

The adsorbent may be activated carbon, silica gel, alumina, or a material for known adsorption purposes.

The step of purifying the recovered impurities to a purity of 99.9% or higher may comprise performing sublimation purification.

Hereinafter, synthetic examples of the compounds represented by Formulas 1 and 2 according to the present invention and examples of manufacturing an organic electronic element will be described in detail with reference to examples, but the present invention is not limited to the following examples.

[Synthesis Example 1] Synthesis of compounds represented by Formulas P-1 to P-16

1. Synthesis Example of P-1

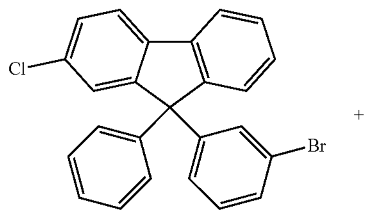

Sub 1A-1

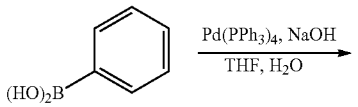

Sub 1A-2

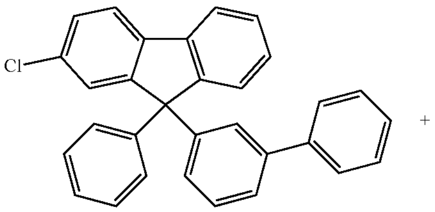

Sub 1A

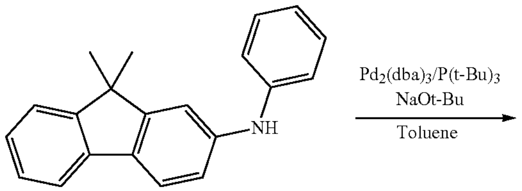

Sub 1B-1

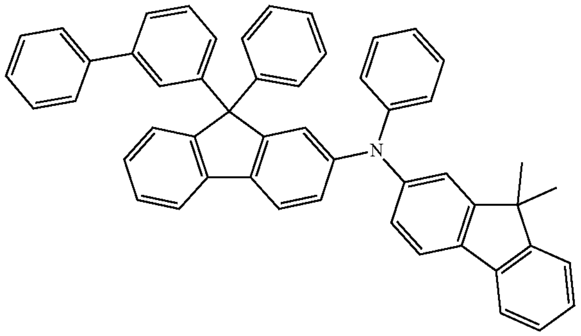

P-1

1) Synthesis of Sub 1A

After putting Sub 1A-1 (50.0 g, 115.8 mmol) in a round bottom flask and dissolving in THF (579 ml), Sub 1A-2 (14.1 g, 115.8 mmol), $Pd(PPh_3)_4$ (8.0 g, 7.0 mmol), NaOH (13.9 g, 347.4 mmol), Water (290 ml) are added and the reaction proceeds at 80° C. After the reaction was completed, extraction was performed with $CH_2Cl_2$ and water, and the organic layer was dried with $MgSO_4$, concentrated, and the resulting organic material was recrystallized using a silicagel column to obtain 42.0 g of the product. (Yield: 84.6%)

2) Synthesis of P-1

After putting Sub 1A (42.0 g, 97.93 mmol) in a round bottom flask and dissolving in THF (490 ml), Sub 1B-1 (27.9 g, 97.9 mmol), $Pd_2(dba)_3$ (2.7 g, 2.9 mmol), $P(t\text{-}Bu)_3$ (1.2 g, 5.8 mmol), NaOt-Bu (18.8 g, 195.8 mmol) are added stirred at 120° C. After the reaction was completed, extraction was performed with $CH_2Cl_2$ and water, and the organic layer was dried with $MgSO_4$, concentrated, and the resulting organic material was recrystallized using a silicagel column to obtain 52.6 g of the product. (Yield: 79.2%)

2. Synthesis Example of P-2

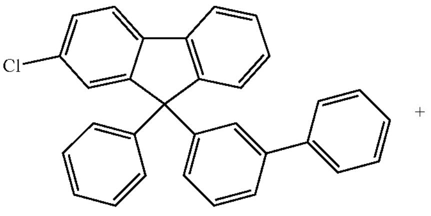

Sub 1A

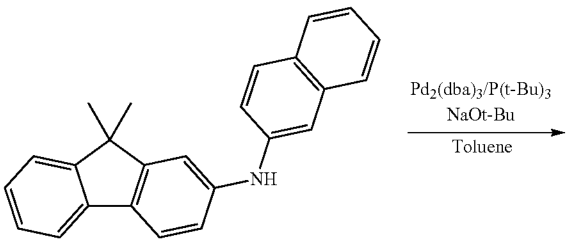

Sub 1B-1

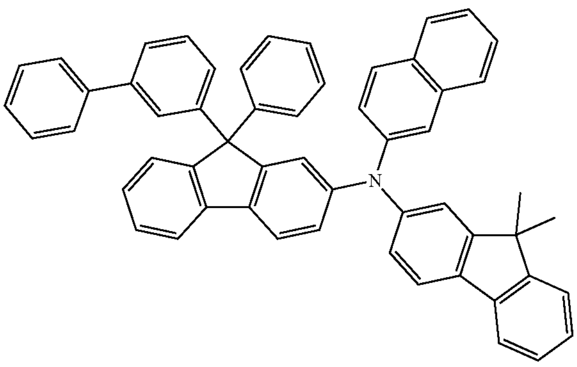

P-2

In a round bottom flask, Sub 1A (50.0 g, 116.6 mmol) and Sub 1B-2 (39.1 g, 116.6 mmol), $Pd_2(dba)_3$ (3.2 g, 3.5 mmol), $P(t\text{-}Bu)_3$ (1.4 g, 7.0 mmol), NaOt-Bu (22.4 g, 233.1 mmol), toluene (583 mL) were tested in the same manner as in P-1 to obtain 63.3 g of product. (Yield: 74.6%)

3. Synthesis Example of P-3

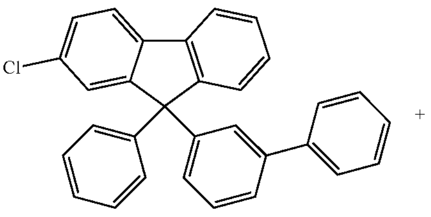

Sub 1A

-continued

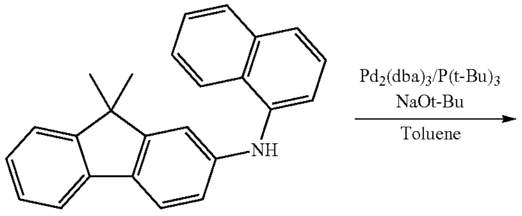

Sub 1B-3

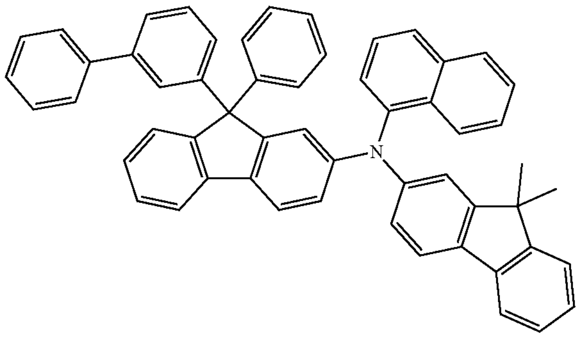

P-3

In a round bottom flask, Sub 1A (50.0 g, 116.6 mmol) and Sub 1B-3 (39.1 g, 116.6 mmol), $Pd_2(dba)_3$ (3.2 g, 3.5 mmol), $P(t\text{-}Bu)_3$ (1.4 g, 7.0 mmol), NaOt-Bu (22.4 g, 233.1 mmol), toluene (583 mL) were tested in the same manner as in P-1 to obtain 62.1 g of product. (Yield: 73.2%)

4. Synthesis Example of P-4

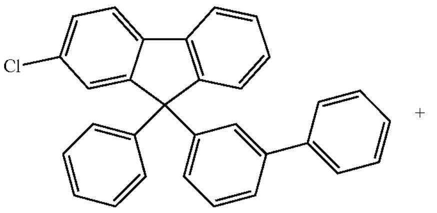

Sub 1A

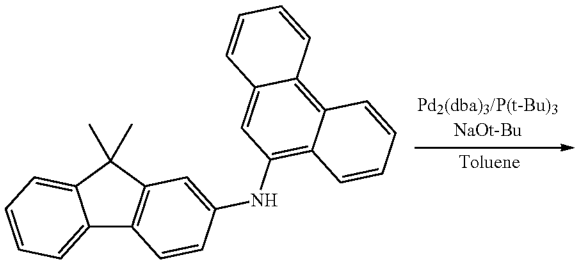

Sub 1B-4

-continued

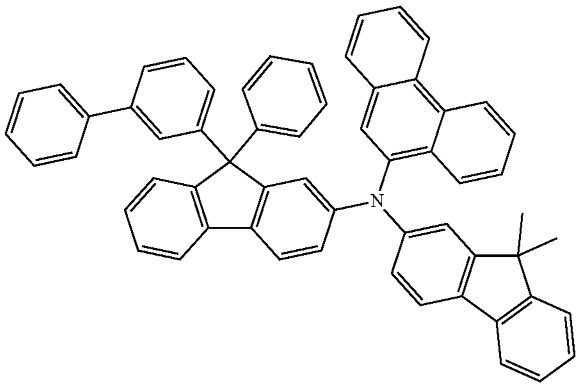

P-4

In a round bottom flask, Sub 1A (50.0 g, 116.6 mmol) and Sub 1B-4 (44.9 g, 116.6 mmol), $Pd_2(dba)_3$ (3.2 g, 3.5 mmol), $P(t\text{-}Bu)_3$ (1.4 g, 7.0 mmol), NaOt-Bu (22.4 g, 233.1 mmol), toluene (583 mL) were tested in the same manner as in P-1 to obtain 65.4 g of product. (Yield: 72.1%)

5. Synthesis Example of P-5

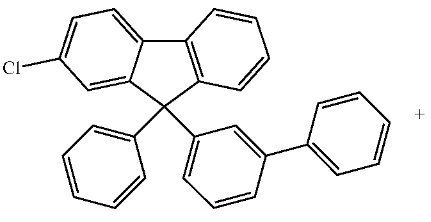

Sub 1A

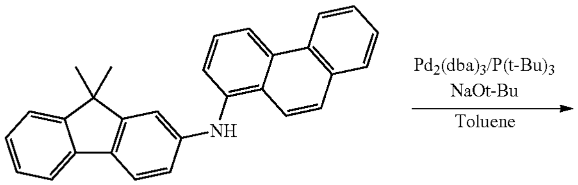

Sub 1B-5

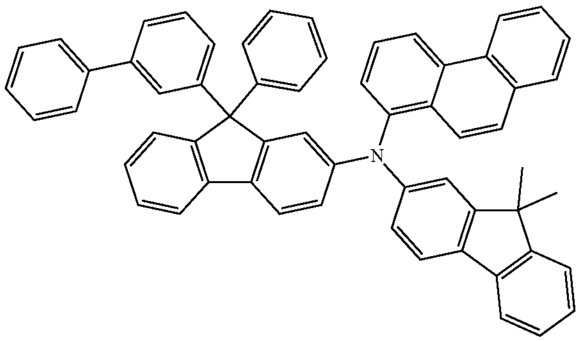

P-5

In a round bottom flask, Sub 1A (50.0 g, 116.6 mmol) and Sub 1B-5 (44.9 g, 116.6 mmol), $Pd_2(dba)_3$ (3.2 g, 3.5 mmol), $P(t\text{-}Bu)_3$ (1.4 g, 7.0 mmol), NaOt-Bu (22.4 g, 233.1 mmol), toluene (583 mL) were tested in the same manner as in P-1 to obtain 65.1 g of product. (Yield: 71.8%)

6. Synthesis Example of P-6

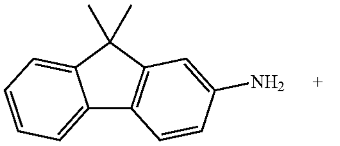

Sub 1B-6-1

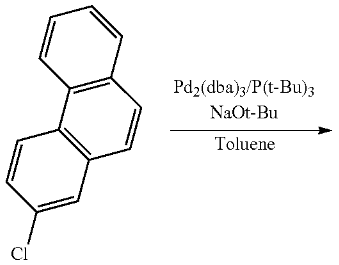

Sub 1B-6-2

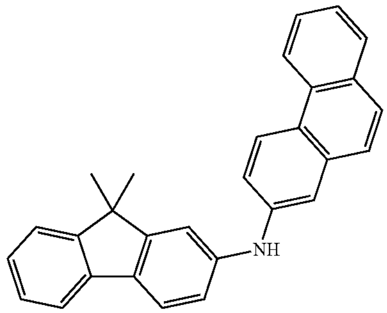

Sub 1B-6

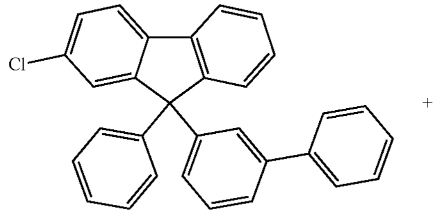

Sub 1A

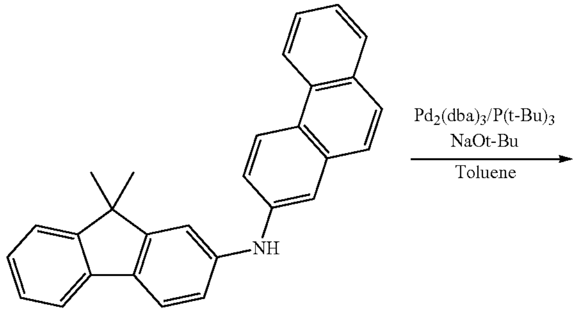

Sub 1B-6

-continued

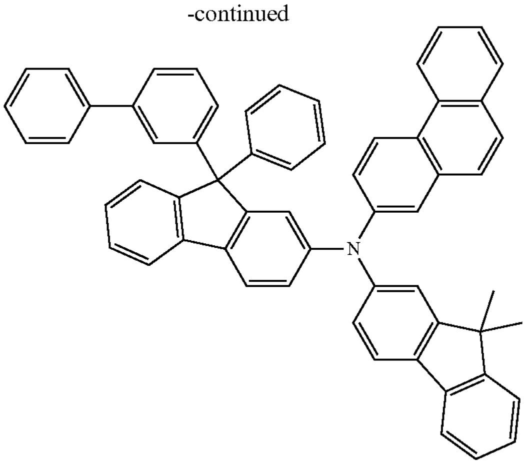

P-6

1) Synthesis of Sub 1B-6

In a round bottom flask, Sub 1B-6-1 (100.0 g, 477.8 mmol) and Sub 1B-6-2 (101.6 g, 477.8 mmol), $Pd_2(dba)_3$ (13.1 g, 14.3 mmol), $P(t-Bu)_3$ (5.8 g, 28.7 mmol), NaOt-Bu (91.8 g, 955.6 mmol), toluene (2389 mL) were tested in the same manner as in P-1 to obtain 135.4 g of product. (Yield: 73.5%)

2) Synthesis of P-6

In a round bottom flask, Sub 1A (50.0 g, 116.6 mmol) and Sub 1B-6 (44.9 g, 116.6 mmol), $Pd_2(dba)_3$ (3.2 g, 3.5 mmol), $P(t-Bu)_3$ (1.4 g, 7.0 mmol), NaOt-Bu (22.4 g, 233.1 mmol), toluene (583 mL) were tested in the same manner as in P-1 to obtain 64.7 g of product. (Yield: 71.3%)

7. Synthesis Example of P-7

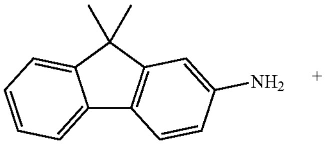

Sub 1B-6-1

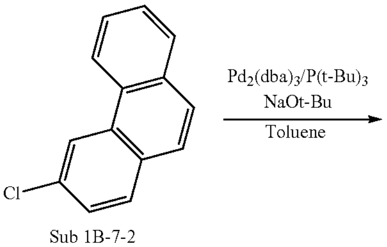

Sub 1B-7-2

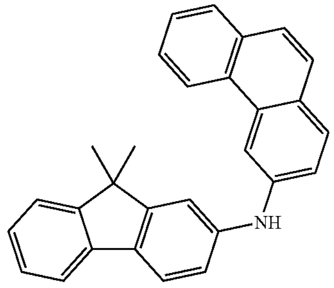

Sub 1B-7

-continued

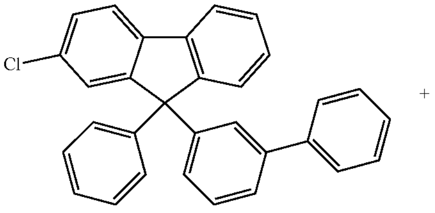

Sub 1A

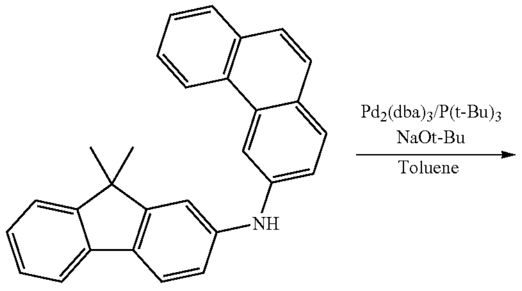

Sub 1B-7

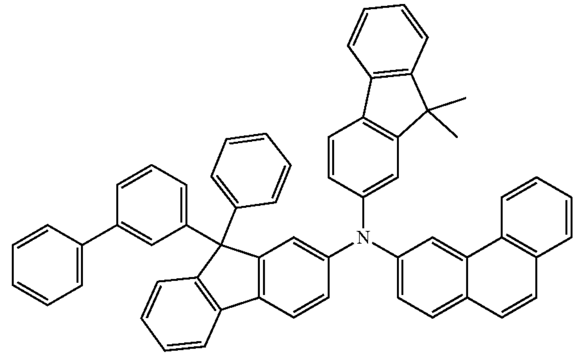

P-7

1) Synthesis of Sub 1B-7

In a round bottom flask, Sub 1B-6-1 (100.0 g, 477.8 mmol) and Sub 1B-7-2 (101.6 g, 477.8 mmol), $Pd_2(dba)_3$ (13.1 g, 14.3 mmol), $P(t\text{-}Bu)_3$ (5.8 g, 28.7 mmol), NaOt-Bu (91.8 g, 955.6 mmol), toluene (2389 mL) were tested in the same manner as in P-1 to obtain 133.2 g of product. (Yield: 72.3%)

2) Synthesis of P-7

In a round bottom flask, Sub 1A (50.0 g, 116.6 mmol) and Sub 1B-7 (44.9 g, 116.6 mmol), $Pd_2(dba)_3$ (3.2 g, 3.5 mmol), $P(t\text{-}Bu)_3$ (1.4 g, 7.0 mmol), NaOt-Bu (22.4 g, 233.1 mmol), toluene (583 mL) were tested in the same manner as in P-1 to obtain 64.9 g of product. (Yield: 71.6%)

8. Synthesis Example of P-8

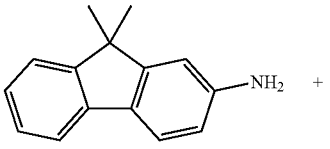

Sub 1B-6-1

-continued

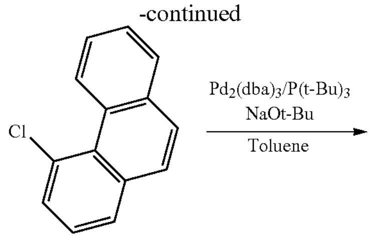

Sub 1B-8-2

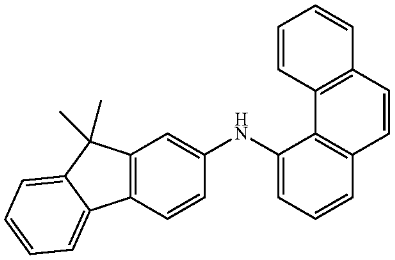

Sub 1B-8

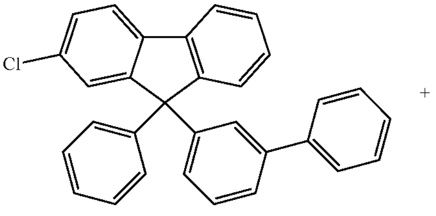

Sub 1A

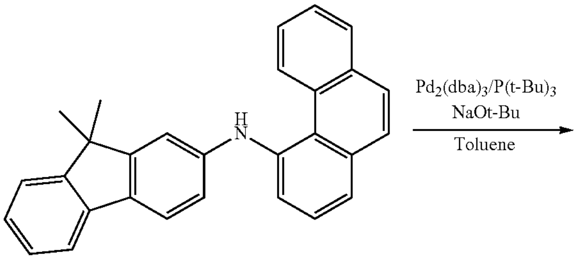

Sub 1B-8

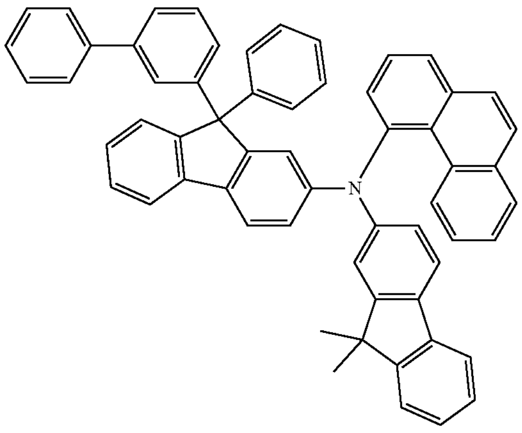

P-8

1) Synthesis of Sub 1B-8

In a round bottom flask, Sub 1B-6-1 (100.0 g, 477.8 mmol) and Sub 1B-8-2 (101.6 g, 477.8 mmol), $Pd_2(dba)_3$ (13.1 g, 14.3 mmol), $P(t\text{-}Bu)_3$ (5.8 g, 28.7 mmol), NaOt-Bu (91.8 g, 955.6 mmol), toluene (2389 mL) were tested in the same manner as in P-1 to obtain 130.2 g of product. (Yield: 70.7%)

2) Synthesis of P-8

In a round bottom flask, Sub 1A (50.0 g, 116.6 mmol) and Sub 1B-8 (44.9 g, 116.6 mmol), $Pd_2(dba)_3$ (3.2 g, 3.5 mmol), $P(t\text{-}Bu)_3$ (1.4 g, 7.0 mmol), NaOt-Bu (22.4 g, 233.1 mmol), toluene (583 mL) were tested in the same manner as in P-1 to obtain 63.0 g of product. (Yield: 69.5%)

9. Synthesis Example of P-9

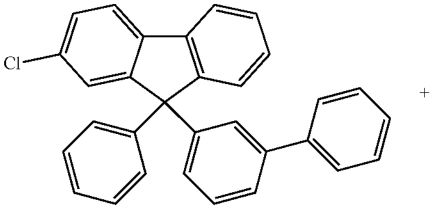

Sub 1A

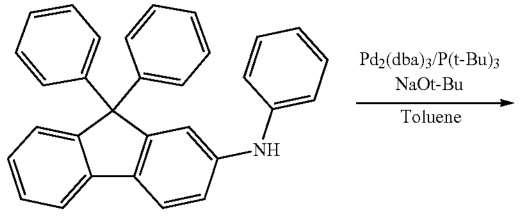

Sub 1B-9

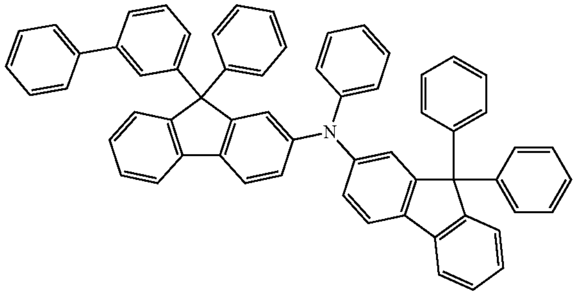

P-9

In a round bottom flask, Sub 1A (50.0 g, 116.6 mmol) and Sub 1B-9 (47.7 g, 116.6 mmol), $Pd_2(dba)_3$ (3.2 g, 3.5 mmol), $P(t\text{-}Bu)_3$ (1.4 g, 7.0 mmol), NaOt-Bu (22.4 g, 233.1 mmol), toluene (583 mL) were tested in the same manner as in P-1 to obtain 69.4 g of product. (Yield: 74.2%)

10. Synthesis Example of P-10

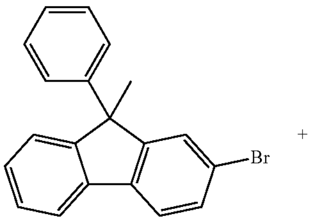

Sub 1B-10-1

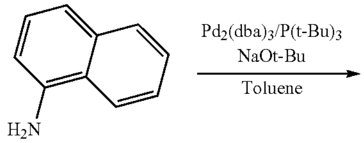

Sub 1B-10-2

-continued

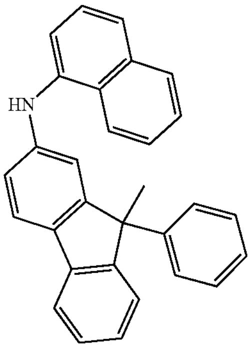

Sub 1B-10

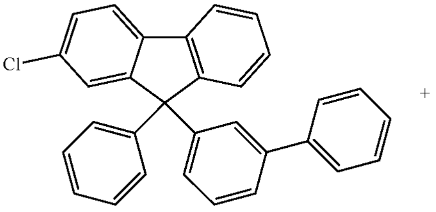

Sub 1A

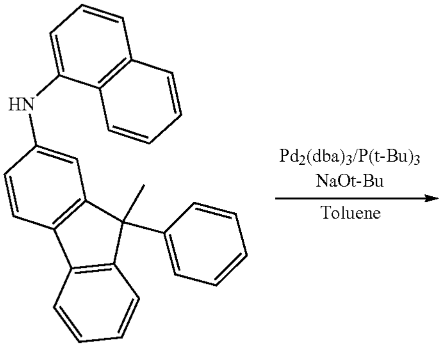

Sub 1B-10

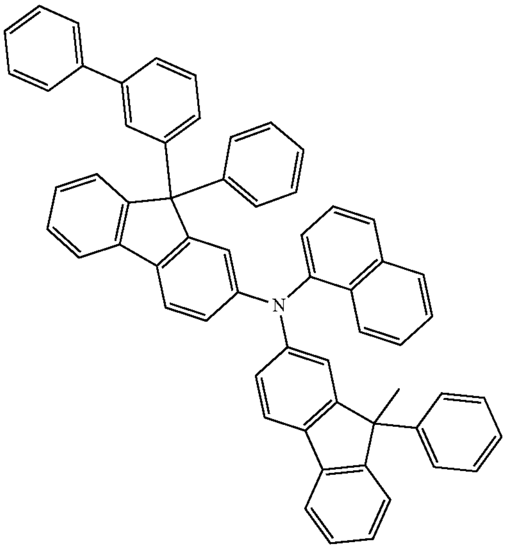

P-10

1) Synthesis of Sub1B-10

In a round bottom flask, Sub 1B-10-1 (100.0 g, 298.3 mmol) and Sub 1B-10-2 (42.7 g, 298.3 mmol), $Pd_2(dba)_3$ (8.2 g, 9.0 mmol), $P(t\text{-}Bu)_3$ (3.6 g, 17.9 mmol), NaOt-Bu (57.3 g, 596.6 mmol), toluene (1491 mL) were tested in the same manner as in P-1 to obtain 85.6 g of product. (Yield: 72.2%)

2) Synthesis of P-10

In a round bottom flask, Sub 1A (50.0 g, 116.6 mmol) and Sub 1B-10 (46.3 g, 116.6 mmol), $Pd_2(dba)_3$ (3.2 g, 3.5 mmol), $P(t\text{-}Bu)_3$ (1.4 g, 7.0 mmol), NaOt-Bu (22.4 g, 233.1 mmol), toluene (583 mL) were tested in the same manner as in P-1 to obtain 69.2 g of product. (Yield: 75.1%)

11. Synthesis Example of P-11

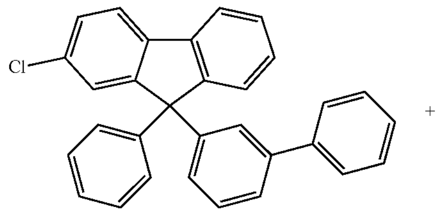

Sub 1A

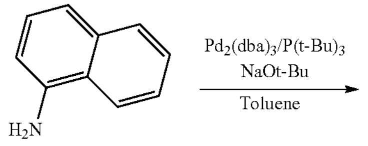

Sub 1B-10-2

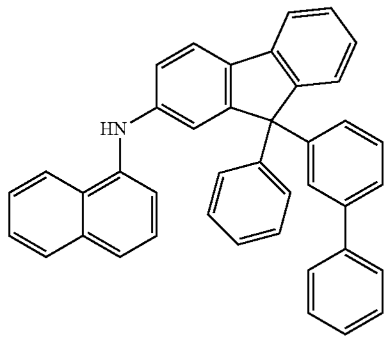

Sub 1B-11

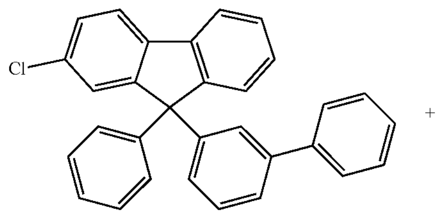

Sub 1A

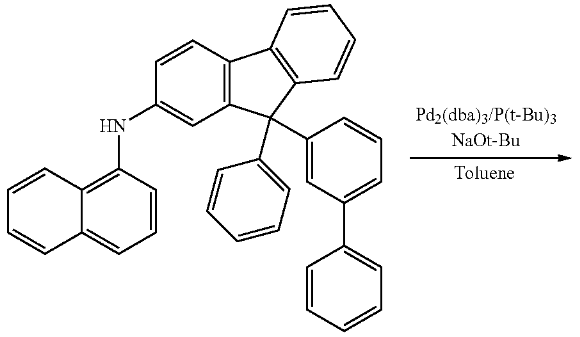

Sub 1B-11

-continued

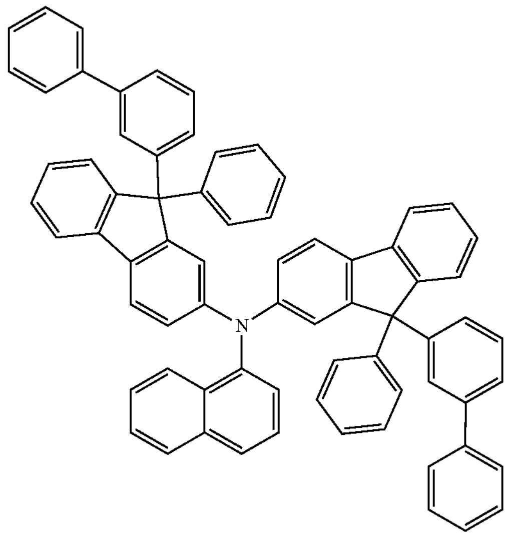

P-11

1) Synthesis of Sub1B-11

In a round bottom flask, Sub 1A (100.0 g, 233.1 mmol) and Sub 1B-10-2 (33.4 g, 233.1 mmol), $Pd_2(dba)_3$ (6.4 g, 7.0 mmol), $P(t\text{-}Bu)_3$ (2.8 g, 14.0 mmol), NaOt-Bu (44.8 g, 466.2 mmol), toluene (1166 mL) were tested in the same manner as in P-1 to obtain 87.2 g of product. (Yield: 69.8%)

2) Synthesis of P-11

In a round bottom flask, Sub 1A (50.0 g, 116.6 mmol) and Sub 1B-11 (62.4 g, 116.6 mmol), $Pd_2(dba)_3$ (3.2 g, 3.5 mmol), $P(t\text{-}Bu)_3$ (1.4 g, 7.0 mmol), NaOt-Bu (22.4 g, 233.1 mmol), toluene (583 mL) were tested in the same manner as in P-1 to obtain 79.3 g of product. (Yield: 73.3%)

12. Synthesis Example of P-12

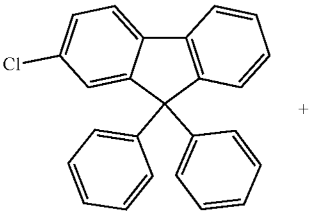

Sub 1B-12-1

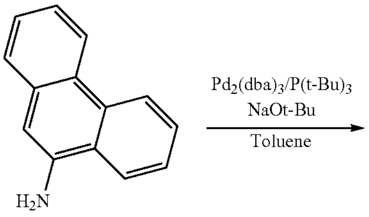

Sub 1B-12-2

-continued

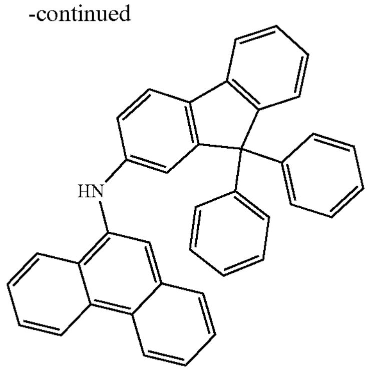

Sub 1B-12

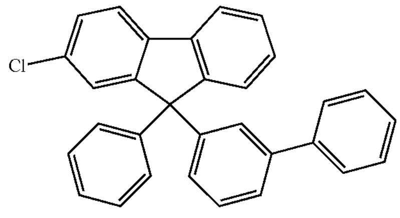

+

Sub 1A

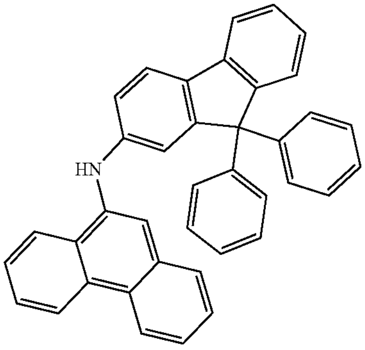

Sub 1B-12

Pd2(dba)3/P(t-Bu)3
NaOt-Bu
Toluene

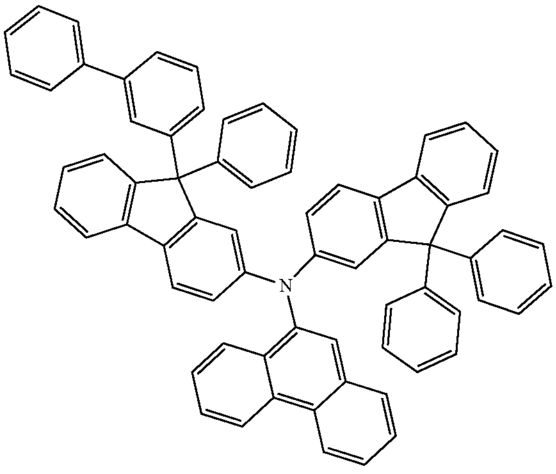

P-12

1) Synthesis of Sub1B-12

In a round bottom flask, Sub 1B-12-1 (100.0 g, 283.4 mmol) and Sub 1B-12-2 (54.8 g, 283.4 mmol), $Pd_2(dba)_3$ (7.8 g, 8.5 mmol), $P(t\text{-}Bu)_3$ (3.4 g, 17.0 mmol), NaOt-Bu (54.5 g, 566.8 mmol), toluene (1417 mL) were tested in the same manner as in P-1 to obtain 99.1 g of product. (Yield: 68.6%)

2) Synthesis of P-12

In a round bottom flask, Sub 1A (50.0 g, 116.6 mmol) and Sub 1B-12 (59.4 g, 116.6 mmol), $Pd_2(dba)_3$ (3.2 g, 3.5 mmol), $P(t\text{-}Bu)_3$ (1.4 g, 7.0 mmol), NaOt-Bu (22.4 g, 233.1 mmol), toluene (583 mL) were tested in the same manner as in P-1 to obtain 75.4 g of product. (Yield: 71.7%)

13. Synthesis Example of P-13

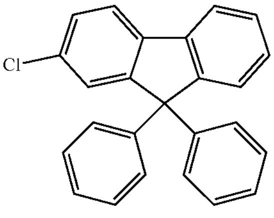

+

Sub 1B-12-1

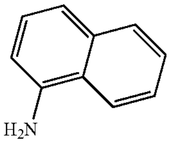

Sub 1B-10-2

Pd2(dba)3/P(t-Bu)3
NaOt-Bu
Toluene

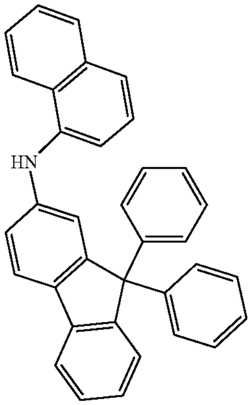

Sub 1B-13

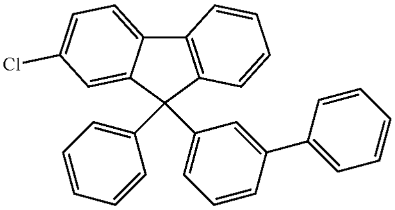

+

Sub 1A

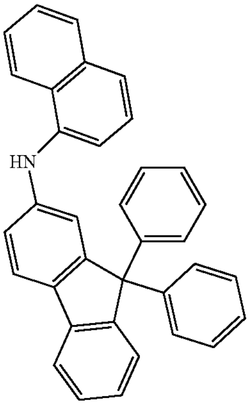

Sub 1B-13

Pd2(dba)3/P(t-Bu)3
NaOt-Bu
Toluene

-continued

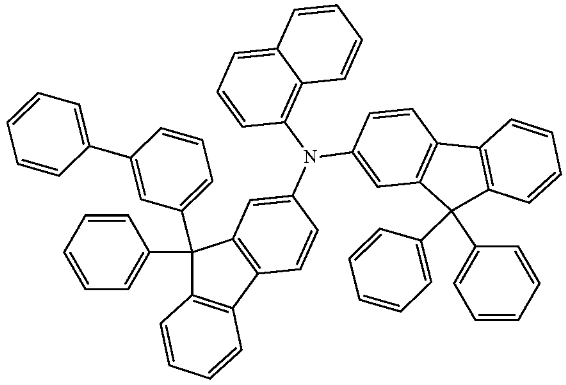

P-13

1) Synthesis of Sub1B-13

In a round bottom flask, Sub 1B-12-1 (100.0 g, 283.4 mmol) and Sub 1B-12-2 (54.8 g, 283.4 mmol), $Pd_2(dba)_3$ (7.8 g, 8.5 mmol), $P(t\text{-}Bu)_3$ (3.4 g, 17.0 mmol), NaOt-Bu (54.5 g, 566.8 mmol), toluene (1417 mL) were tested in the same manner as in P-1 to obtain 90.4 g of product. (Yield: 69.4%)

2) Synthesis of P-13

In a round bottom flask, Sub 1A (50.0 g, 116.6 mmol) and Sub 1B-13 (53.6 g, 116.6 mmol), $Pd_2(dba)_3$ (3.2 g, 3.5 mmol), $P(t\text{-}Bu)_3$ (1.4 g, 7.0 mmol), NaOt-Bu (22.4 g, 233.1 mmol), toluene (583 mL) were tested in the same manner as in P-1 to obtain 71.6 g of product. (Yield: 72.1%)

14. Synthesis Example of P-14

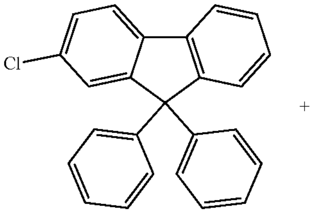

Sub 1B-12-1

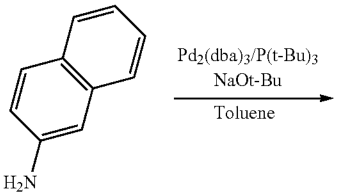

Sub 1B-14-2

-continued

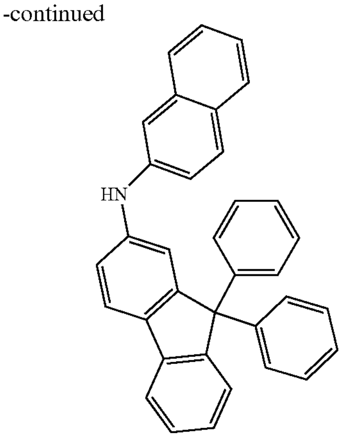

Sub 1B-14

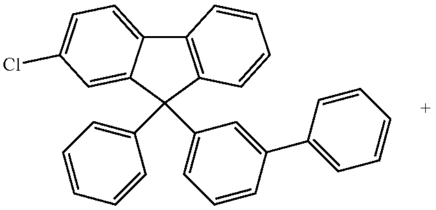

Sub 1A

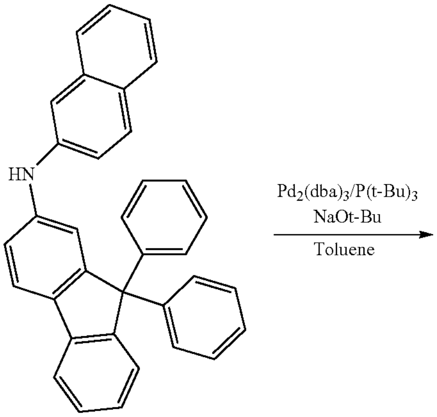

Sub 1B-14

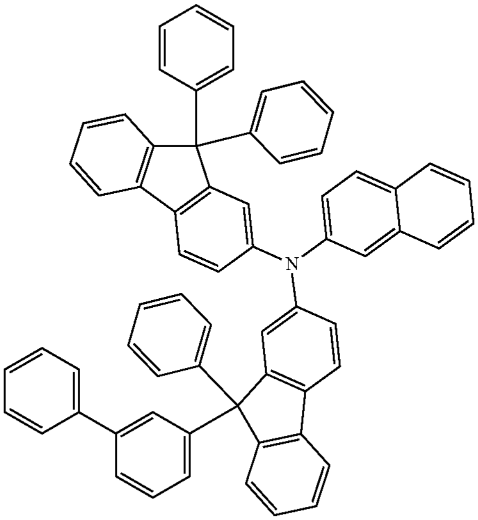

P-14

1) Synthesis of Sub1B-14

In a round bottom flask, Sub 1B-12-1 (100.0 g, 283.4 mmol) and Sub 1B-14-2 (40.6 g, 283.4 mmol), $Pd_2(dba)_3$ (7.8 g, 8.5 mmol), $P(t-Bu)_3$ (3.4 g, 17.0 mmol), NaOt-Bu (54.5 g, 566.8 mmol), toluene (1417 mL) were tested in the same manner as in P-1 to obtain 91.0 g of product. (Yield: 69.9%)

2) Synthesis of P-14

In a round bottom flask, Sub 1A (50.0 g, 116.6 mmol) and Sub 1B-14 (53.6 g, 116.6 mmol), $Pd_2(dba)_3$ (3.2 g, 3.5 mmol), $P(t-Bu)_3$ (1.4 g, 7.0 mmol), NaOt-Bu (22.4 g, 233.1 mmol), toluene (583 mL) were tested in the same manner as in P-1 to obtain 71.9 g of product. (Yield: 72.4%)

15. Synthesis Example of P-15

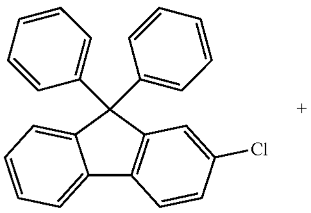

Sub 1B-12-1

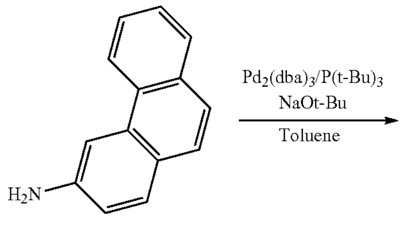

Sub 1B-15-2

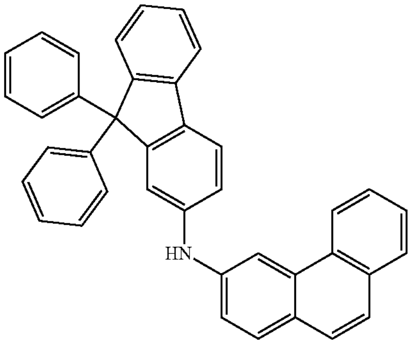

Sub 1B-15

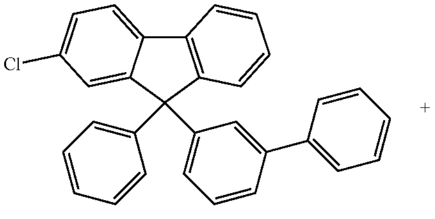

Sub 1A

-continued

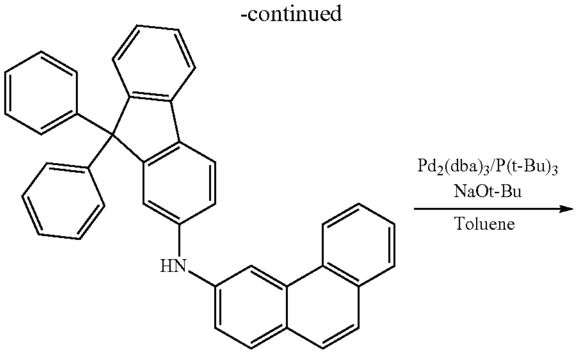

Sub 1B-15

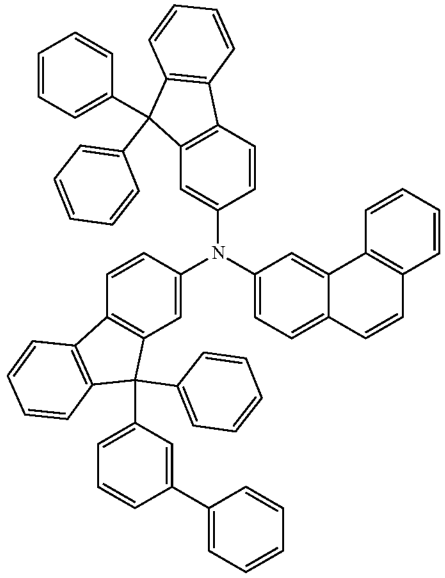

P-15

1) Synthesis of Sub1B-15

In a round bottom flask, Sub 1B-12-1 (100.0 g, 283.4 mmol) and Sub 1B-15-2 (54.8 g, 283.4 mmol), $Pd_2(dba)_3$ (7.8 g, 8.5 mmol), $P(t-Bu)_3$ (3.4 g, 17.0 mmol), NaOt-Bu (54.5 g, 566.8 mmol), toluene (1417 mL) were tested in the same manner as in P-1 to obtain 97.6 g of product. (Yield: 67.6%)

2) Synthesis of P-15

In a round bottom flask, Sub 1A (50.0 g, 116.6 mmol) and Sub 1B-15 (59.4 g, 116.6 mmol), $Pd_2(dba)_3$ (3.2 g, 3.5 mmol), $P(t-Bu)_3$ (1.4 g, 7.0 mmol), NaOt-Bu (22.4 g, 233.1 mmol), toluene (583 mL) were tested in the same manner as in P-1 to obtain 74.6 g of product. (Yield: 70.9%)

16. Synthesis Example of P-16

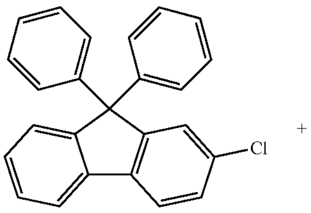

Sub 1B-12-1

-continued

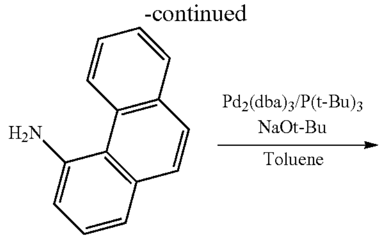

Sub 1B-16-2

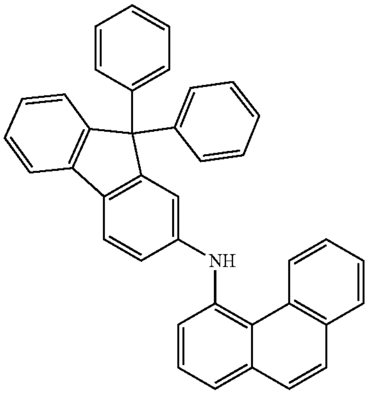

Sub 1B-16

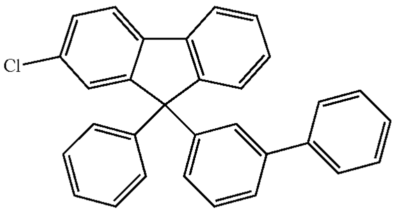

Sub 1A

+

-continued

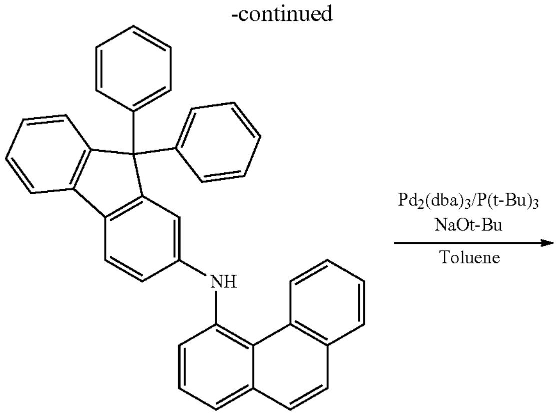

Sub 1B-16

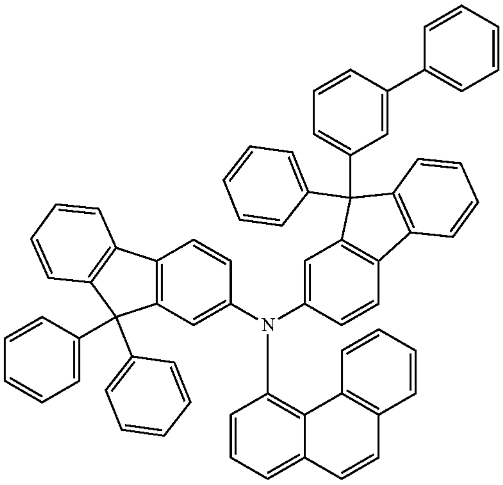

P-16

1) Synthesis of Sub1B-16

In a round bottom flask, Sub 1B-12-1 (100.0 g, 283.4 mmol) and Sub 1B-16-2 (54.8 g, 283.4 mmol), $Pd_2(dba)_3$ (7.8 g, 8.5 mmol), $P(t-Bu)_3$ (3.4 g, 17.0 mmol), NaOt-Bu (54.5 g, 566.8 mmol), toluene (1417 mL) were tested in the same manner as in P-1 to obtain 96.5 g of product. (Yield: 66.8%)

2) Synthesis of P-16

In a round bottom flask, Sub 1A (50.0 g, 116.6 mmol) and Sub 1B-16 (59.4 g, 116.6 mmol), $Pd_2(dba)_3$ (3.2 g, 3.5 mmol), $P(t-Bu)_3$ (1.4 g, 7.0 mmol), NaOt-Bu (22.4 g, 233.1 mmol), toluene (583 mL) were tested in the same manner as in P-1 to obtain 72.9 g of product. (Yield: 69.3%)

FD-MS (Field Desorption-Mass Spectrometry) values of the compounds P-1 to P-16 of the present invention prepared according to the Synthesis Example as described above are shown in Table 1.

TABLE 1

| compound | FD-MS | compound | FD-MS |
|---|---|---|---|
| P-1 | m/z = 677.31($C_{52}H_{39}N$ = 677.89) | P-2 | m/z = 727.32($C_{56}H_{41}N$ = 727.95) |
| P-3 | m/z = 727.32($C_{56}H_{41}N$ = 727.95) | P-4 | m/z = 777.34($C_{60}H_{43}N$ = 778.01) |
| P-5 | m/z = 777.34($C_{60}H_{43}N$ = 778.01) | P-6 | m/z = 777.34($C_{60}H_{43}N$ = 778.01) |
| P-7 | m/z = 777.34($C_{60}H_{43}N$ = 778.01) | P-8 | m/z = 777.34($C_{60}H_{43}N$ = 778.01) |
| P-9 | m/z = 801.34($C_{62}H_{43}N$ = 802.03) | P-10 | m/z = 789.34($C_{61}H_{43}N$ = 790.02) |
| P-11 | m/z = 927.39($C_{72}H_{49}N$ = 928.19) | P-12 | m/z = 901,37($C_{70}H_{47}N$ = 902.15) |
| P-13 | m/z = 851.36($C_{66}H_{45}N$ = 852.09) | P-14 | m/z = 851.36($C_{66}H_{45}N$ = 852.09) |
| P-15 | m/z = 901.37($C_{70}H_{47}N$ = 902.15) | P-16 | m/z = 901.37($C_{70}H_{47}N$ = 902.15) |

[Synthesis Example 2] Compound represented by Formula 2

1. Synthesis example of N-7

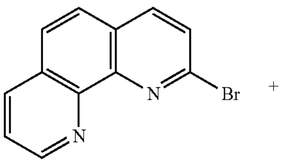

Sub 2A-7

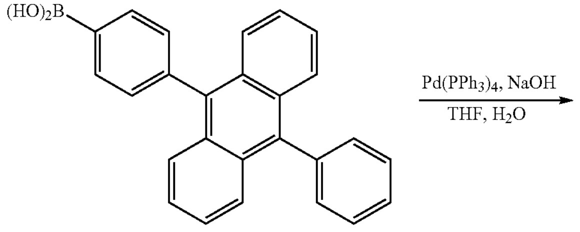

Sub 2B-7

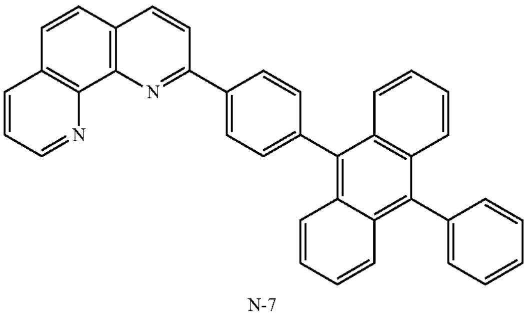

N-7

After putting Sub 2A-7 (50.0 g, 193.0 mmol) in a round bottom flask and dissolving in THF (965 ml), Sub 2B-7 (72.2 g, 193.0 mmol), $Pd(PPh_3)_4$ (13.4 g, 11.6 mmol), NaOH (23.2 g, 578.9 mmol), water (482 ml) were added and tested in the same manner as in Sub 1A-2 to obtain 82.0 g of product. (Yield: 83.5%)

2. Synthesis example of N-18

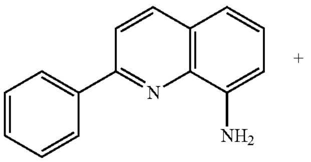

Sub 2A-18-1

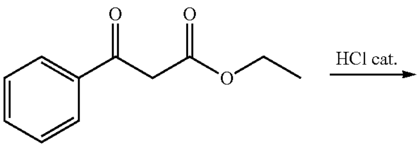

Sub 2A-18-2

-continued

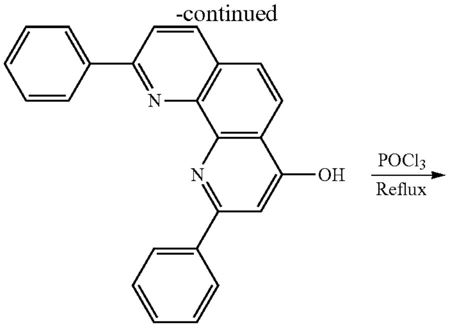

Sub 2A-18-3

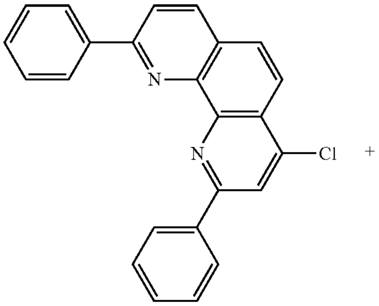

Sub 2A-18

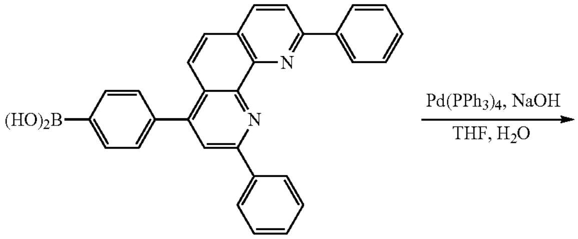

Sub 2B-18

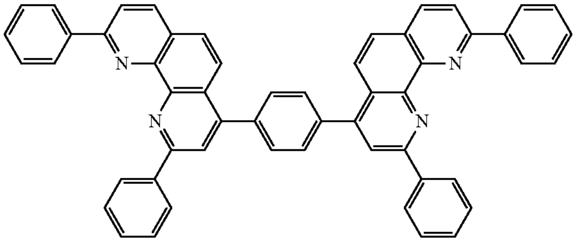

N-18

1) Synthesis of Sub 2A-18-3

Sub 2A-18-1 (50.0 g, 227.0 mmol) and Sub 2A-18-2 (43.6 g, 227.0 mmol) were placed in a round bottom flask, sufficiently dissolved in 1N HCl, and stirred at 120° C. for 24 hours. After the reaction is complete, the mixture is cooled to room temperature, extracted with toluene and water, dried over $MgSO_4$, and concentrated. After repeating the reaction two more times in the same manner as above, the obtained material was transferred to a flask containing Diphenyl Ether (50 ml), heated to 260° C., sufficiently dissolved, and slowly added dropwise to a reactor containing Diphenyl Ether (100 ml). After 30 minutes, the mixture was cooled to room temperature, extracted with hexane and brine, and the organic layer was dried with $MgSO_4$, concentrated, and the resulting organic material was recrystallized using a silica gel column to obtain 42.7 g of the product. (Yield: 54.0%)

2) Synthesis of Sub 2A-18

Sub 2A-18-3 (50.0 g, 115.8 mmol) was added to a round-bottom flask, $POCl_3$ (500 ml) was slowly added, and the mixture was refluxed for 4 hours. After the reaction was completed, cooling to room temperature, the reaction solution was neutralized by adding saturated $NH_4OH$. After extraction with dichloromatane and water, the organic layer was dried with $MgSO_4$, concentrated, and the resulting organic material was recrystallized using a silica gel column to obtain 38.3 g of the product. (Yield: 85.1%)

3) Synthesis of N-18

After putting Sub 2A-18 (38.3 g, 104.4 mmol) in a round bottom flask and dissolving in THF (522 ml), Sub 2B-18 (47.2 g, 104.4 mmol), $Pd(PPh_3)_4$ (7.2 g, 6.3 mmol), NaOH (12.5 g, 313.2 mmol), water (261 ml) were added and 63.0 g of the product was obtained in the same manner as in Sub 1A. (Yield: 81.7%)

3. Synthesis example of N-24

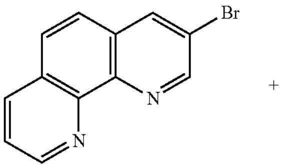

Sub 2A-24

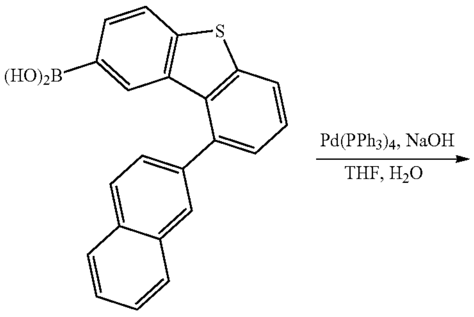

Sub 2B-24

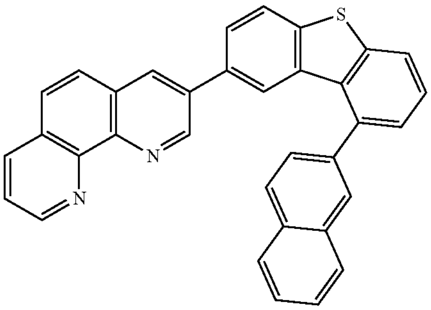

N-24

After putting Sub 2A-24 (30.0 g, 115.8 mmol) in a round bottom flask and dissolving in THF (579 ml), Sub 2B-24 (41.0 g, 115.8 mmol), $Pd(PPh_3)_4$ (8.0 g, 7.0 mmol), NaOH (13.9 g, 347.3 mmol), water (289 ml) were added and 45.6 g of the product was obtained in the same manner as in Sub 1A. (Yield: 80.6%)

4. Synthesis example of N-35

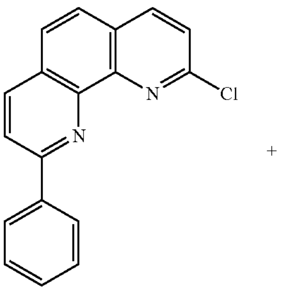

Sub 2A-35

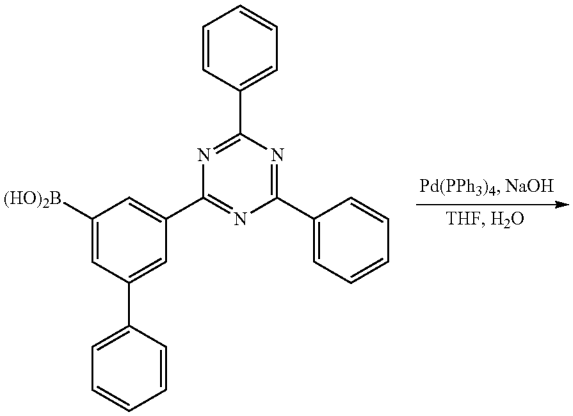

Sub 2B-35

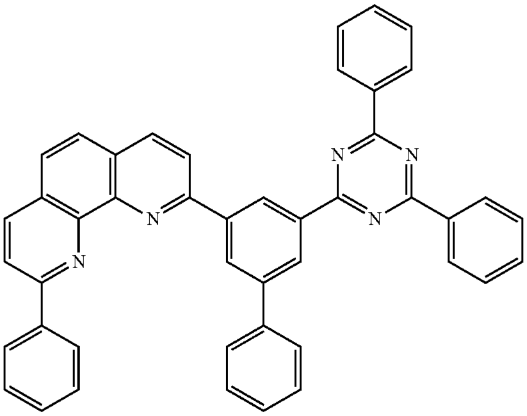

N-35

After putting Sub 2A-35 (30.0 g, 103.2 mmol) in a round bottom flask and dissolving in THF (516 ml), Sub 2B-35 (44.3 g, 103.2 mmol), $Pd(PPh_3)_4$ (7.2 g, 6.2 mmol), NaOH (12.4 g, 309.5 mmol), water (258 ml) were added and 53.5 g of the product was obtained in the same manner as in Sub 1A. (Yield: 81.1%)

5. Synthesis example of N-38

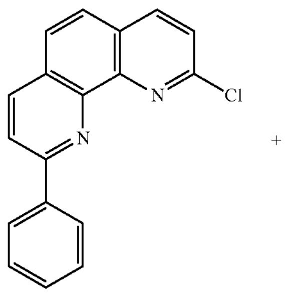

Sub 2A-35

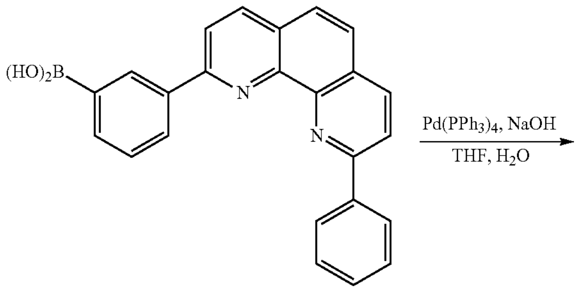

Sub 2B-38

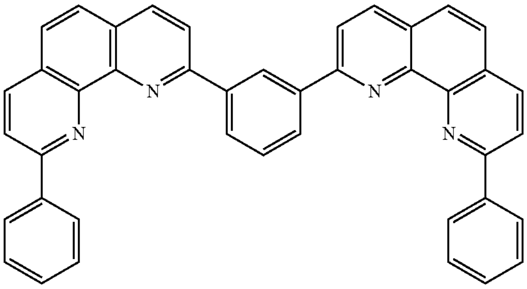

N-38

After putting Sub 2A-35 (30.0 g, 103.2 mmol) in a round bottom flask and dissolving in THF (516 ml), Sub 2B-38 (48.8 g, 103.2 mmol), $Pd(PPh_3)_4$ (7.2 g, 6.2 mmol), NaOH (12.4 g, 309.5 mmol), water (258 ml) were added and 49.8 g of the product was obtained in the same manner as in Sub 1A. (Yield: 82.3%)

6. Synthesis example of N-46

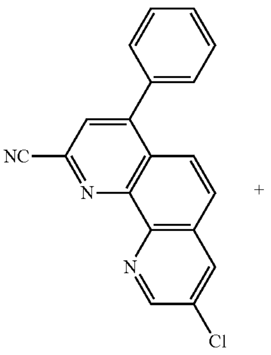

Sub 2A-46

-continued

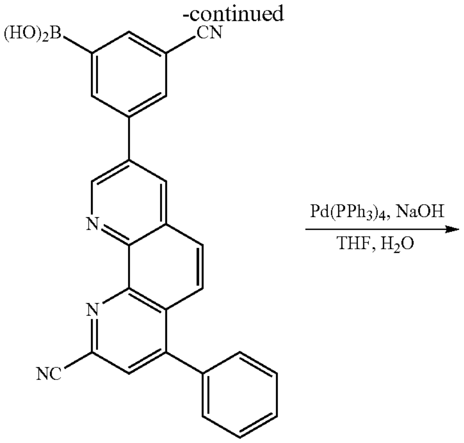

Sub 2B-46

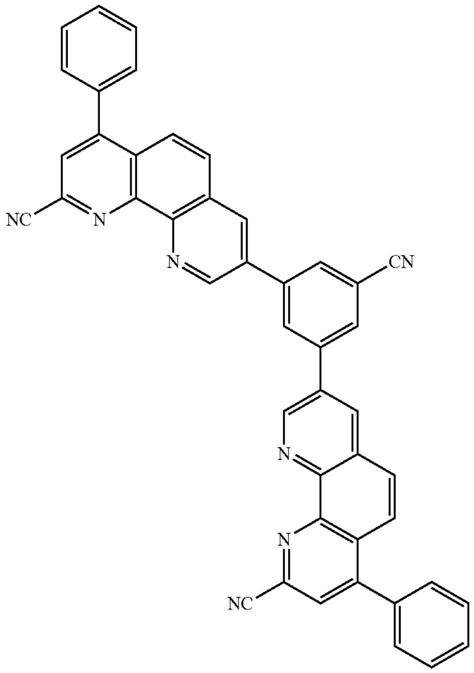

N-46

After putting Sub 2A-46 (30.0 g, 95.0 mmol) in a round bottom flask and dissolving in THF (475 ml), Sub 2B-46 (40.5 g, 95.0 mmol), $Pd(PPh_3)_4$ (6.6 g, 5.7 mmol), NaOH (11.4 g, 285.0 mmol), water (238 ml) were added and 51.9 g of the product was obtained in the same manner as in Sub 1A. (Yield: 82.6%)

7. Synthesis example of N-57

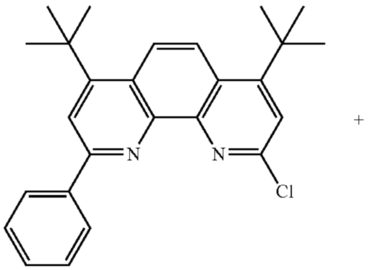

Sub 2A-57

-continued

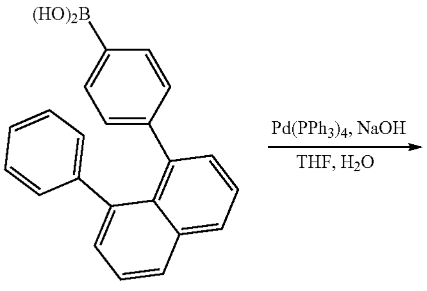

Sub 2B-57

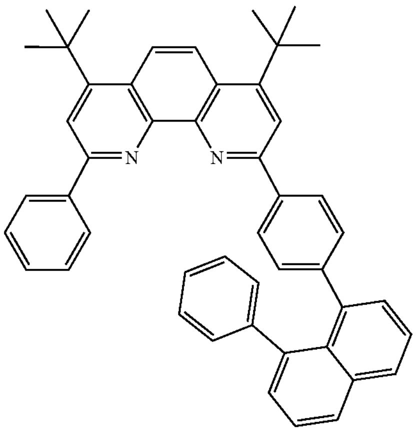

N-57

After putting Sub 2A-57 (30.0 g, 74.4 mmol) in a round bottom flask and dissolving in THF (372 ml), Sub 2B-57 (24.1 g, 74.4 mmol), $Pd(PPh_3)_4$ (5.2 g, 4.5 mmol), NaOH (8.9 g, 223.3 mmol), water (186 ml) were added and 39.4 g of the product was obtained in the same manner as in Sub 1A. (Yield: 81.8%)

8. Synthesis example of N-92

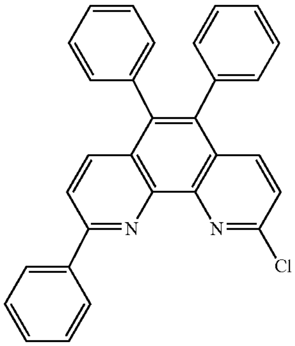

Sub 2A-92

+

-continued

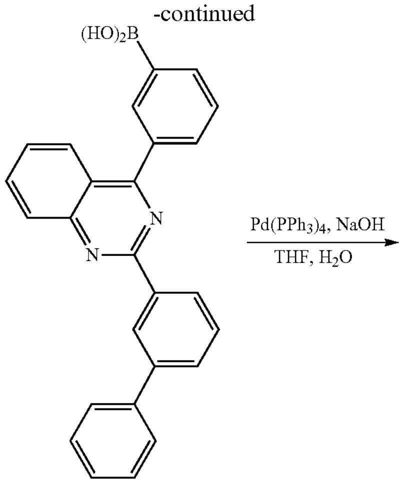

Sub 2B-92

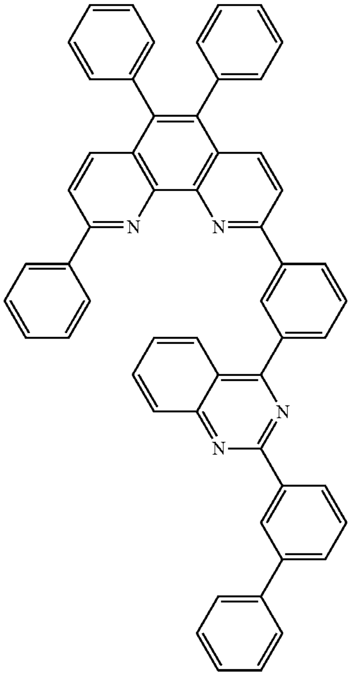

N-92

After putting Sub 2A-92 (30.0 g, 67.7 mmol) in a round bottom flask and dissolving in THF (339 ml), Sub 2B-92 (27.2 g, 67.7 mmol), $Pd(PPh_3)_4$ (4.7 g, 4.1 mmol), NaOH (8.1 g, 203.2 mmol), water (169 ml) were added and 41.4 g of the product was obtained in the same manner as in Sub 1A. (Yield: 79.9%)

FD-MS (Field Desorption-Mass Spectrometry) values of the compounds N-1 to N-92 of the present invention prepared according to the Synthesis Example as described above are shown in Table 2.

TABLE 2

| compound | FD-MS | compound | FD-MS |
|---|---|---|---|
| N-1 | m/z = 458.18($C_{34}H_{22}N_2$ = 458.56) | N-2 | m/z = 610.24($C_{46}H_{30}N_2$ = 610.76) |
| N-3 | m/z = 610.24($C_{46}H_{30}N_2$ = 610.76) | N-4 | m/z = 411.17($C_{29}H_{21}N_3$ = 411.51) |
| N-5 | m/z = 486.18($C_{34}H_{22}N_4$ = 486.58) | N-6 | m/z = 459.17($C_{33}H_{21}N_3$ = 459.55) |
| N-7 | m/z = 508.19($C_{38}H_{24}N_2$ = 508.62) | N-8 | m/z = 432.16($C_{32}H_{20}N_2$ = 432.53) |
| N-9 | m/z = 482.18($C_{36}H_{22}N_2$ = 482.59) | N-10 | m/z = 482.18($C_{36}H_{22}N_2$ = 482.59) |
| N-11 | m/z = 508.19($C_{38}H_{24}N_2$ = 508.62) | N-12 | m/z = 584.23($C_{44}H_{28}N_2$ = 584.72) |
| N-13 | m/z = 634.24($C_{48}H_{30}N_2$ = 634.78) | N-14 | m/z = 565.25($C_{41}H_{31}N_3$ = 565.72) |
| N-15 | m/z = 542.18($C_{38}H_{26}N_2S$ = 542.70) | N-16 | m/z = 482.18($C_{36}H_{22}N_2$ = 482.59) |
| N-17 | m/z = 434.15($C_{30}H_{18}N_4$ = 434.50) | N-18 | m/z = 738.28($C_{54}H_{34}N_4$ = 738.89) |
| N-19 | m/z = 492.23($C_{34}H_{28}N_4$ = 492.63) | N-20 | m/z = 562.22($C_{40}H_{26}N_4$ = 562.68) |
| N-21 | m/z = 659.33($C_{48}H_{41}N_3$ = 659.88) | N-22 | m/z = 792.35($C_{60}H_{44}N_2$ = 793.03) |
| N-23 | m/z = 574.20($C_{42}H_{26}N_2O$ = 574.68) | N-24 | m/z = 488.13($C_{34}H_{20}N_2S$ = 488.61) |
| N-25 | m/z = 768.30($C_{54}H_{36}N_6$ = 768.92) | N-26 | m/z = 562.22($C_{40}H_{26}N_4$ = 562.68) |
| N-27 | m/z = 639.24($C_{45}H_{29}N_5$ = 639.76) | N-28 | m/z = 536.20($C_{38}H_{24}N_4$ = 536.64) |
| N-29 | m/z = 802.33($C_{61}H_{42}N_2$ = 803.02) | N-30 | m/z = 662.25($C_{48}H_{30}N_4$ = 662.80) |
| N-31 | m/z = 648.26($C_{49}H_{32}N_2$ = 648.81) | N-32 | m/z = 546.30($C_{40}H_{38}N_2$ = 546.76) |
| N-33 | m/z = 601.35($C_{43}H_{43}N_3$ = 601.84) | N-34 | m/z = 536.17($C_{36}H_{20}N_6$ = 536.60) |
| N-35 | m/z = 639.24($C_{45}H_{29}N_5$ = 639.76) | N-36 | m/z = 668.29($C_{48}H_{36}N_4$ = 668.84) |
| N-37 | m/z = 586.22($C_{42}H_{26}N_4$ = 586.70) | N-38 | m/z = 586.22($C_{42}H_{26}N_4$ = 586.70) |
| N-39 | m/z = 586.22($C_{42}H_{26}N_4$ = 586.70) | N-40 | m/z = 490.22($C_{34}H_{26}N_4$ = 490.61) |
| N-41 | m/z = 664.24($C_{46}H_{28}N_6$ = 664.77) | N-42 | m/z = 664.24($C_{46}H_{28}N_6$ = 664.77) |
| N-43 | m/z = 662.25($C_{48}H_{30}N_4$ = 662.80) | N-44 | m/z = 702.37($C_{50}H_{46}N_4$ = 702.95) |
| N-45 | m/z = 596.28($C_{42}H_{16}D_{10}N_4$ = 596.76) | N-46 | m/z = 661.20($C_{45}H_{23}N_7$ = 661.73) |
| N-47 | m/z = 512.18($C_{33}H_{22}F_2N_4$ = 512.56) | N-48 | m/z = 648.30($C_{44}H_{36}N_6$ = 648.81) |
| N-49 | m/z = 586.22($C_{42}H_{26}N_4$ = 586.70) | N-50 | m/z = 771.34($C_{55}H_{41}N_5$ = 771.97) |
| N-51 | m/z = 737.28($C_{55}H_{35}N_3$ = 737.91) | N-52 | m/z = 636.21($C_{44}H_{24}N_6$ = 636.72) |
| N-53 | m/z = 612.38($C_{42}D_{26}N_4$ = 612.86) | N-54 | m/z = 940.33($C_{68}H_{40}N_6$ = 941.11) |
| N-55 | m/z = 688.24($C_{48}H_{28}N_6$ = 688.79) | N-56 | m/z = 592.26($C_{42}H_{32}N_4$ = 592.75) |
| N-57 | m/z = 646.33($C_{48}H_{42}N_2$ = 646.88) | N-58 | m/z = 534.21($C_{40}H_{26}N_2$ = 534.66) |
| N-59 | m/z = 661.25($C_{49}H_{31}N_3$ = 661.81) | N-60 | m/z = 736.26($C_{54}H_{32}N_4$ = 736.88) |
| N-61 | m/z = 718.33($C_{54}H_{42}N_2$ = 718.94) | N-62 | m/z = 711.27($C_{53}H_{33}N_3$ = 711.87) |
| N-63 | m/z = 743.25($C_{49}H_{29}N_9$ = 743.83) | N-64 | m/z = 740.27($C_{52}H_{32}N_6$ = 740.87) |
| N-65 | m/z = 653.22($C_{45}H_{27}N_5O$ = 653.75) | N-66 | m/z = 664.26($C_{48}H_{32}N_4$ = 664.81) |
| N-67 | m/z = 738.28($C_{54}H_{34}N_4$ = 738.89) | N-68 | m/z = 890.34($C_{66}H_{42}N_4$ = 891.09) |
| N-69 | m/z = 614.25($C_{44}H_{30}N_4$ = 614.75) | N-70 | m/z = 906.35($C_{65}H_{4}2N_6$ = 907.09) |
| N-71 | m/z = 855.34($C_{62}H_{41}N_5$ = 856.04) | N-72 | m/z = 564.21($C_{37}H_{26}F_2N_4$ = 564.64) |
| N-73 | m/z = 740.27($C_{52}H_{32}N_6$ = 740.87) | N-74 | m/z = 647.18($C_{44}H_{23}F_2N_3O$ = 647.68) |
| N-75 | m/z = 616.23($C_{44}H_{32}N_2Si$ = 616.84) | N-76 | m/z = 646.24($C_{49}H_{30}N_2$ = 646.79) |
| N-77 | m/z = 537.22($C_{39}H_{27}N_3$ = 537.67) | N-78 | m/z = 570.19($C_{39}H_{18}D_5N_3S$ = 570.72) |
| N-79 | m/z = 1011.41($C_{73}H_{41}D_5N_6$ = 1012.24) | N-80 | m/z = 789.26($C_{55}H_{31}N_7$ = 789.90) |
| N-81 | m/z = 816.30($C_{58}H_{36}N_6$ = 816.97) | N-82 | m/z = 892.33($C_{64}H_{40}N_6$ = 893.07) |
| N-83 | m/z = 752.29($C_{55}H_{36}N_4$ = 752.92) | N-84 | m/z = 740.27($C_{52}H_{32}N_6$ = 740.87) |
| N-85 | m/z = 832.30($C_{60}H_{37}FN_4$ = 832.98) | N-86 | m/z = 712.29($C_{54}H_{36}N_2$ = 712.90) |
| N-87 | m/z = 888.35($C_{68}H_{44}N_2$ = 889.11) | N-88 | m/z = 824.37($C_{60}H_{28}D_{10}N_4$ = 825.05) |
| N-89 | m/z = 992.36($C_{72}H_{44}N_6$ = 993.19) | N-90 | m/z = 840.30($C_{60}H_{36}N_6$ = 840.99) |
| N-91 | m/z = 794.29($C_{54}H_{34}N_8$ = 794.92) | N-92 | m/z = 764.29($C_{56}H_{36}N_4$ = 764.93) |

Otherwise, the synthesis examples of the present invention represented by the Formulas 1 and 2 have been described, but these are all based on the Buchwald-Hartwig cross coupling reaction, Miyaura boration reaction, Suzuki cross-coupling reaction, Intramolecular acid-induced cyclization reaction (J. mater. Chem. 1999, 9, 2095.), Pd(II)-catalyzed oxidative cyclization reaction (Org. Lett.2011, 13, 5504), and $PPh_3$-mediated reductive cyclization reaction (J. Org. Chem. 2005, 70, 5014.), and it will be easily understood by those skilled in the art that the reaction proceeds even when other substituents defined in Formulas 1 and 2 are bonded in addition to the substituents specified in the specific synthesis examples.

Evaluation of Manufacture of Organic Electronic element

When the organic electronic element according to the present specification is a top emission type, and the first electrode is formed on the substrate before forming the organic material layer and the second electrode, not only a transparent material but also an opaque material having excellent light reflectance can be used as a material for the first electrode.

When the organic electronic element according to the present specification is a bottom emission type, and the first electrode is formed on the substrate before forming the organic material layer and the second electrode, a transparent material must be used as the first electrode material, or an opaque material must be formed into a thin film to such an extent that it becomes transparent.

In this embodiment, a top emission type tandem OLED is manufactured and the following embodiments are presented, but the embodiments of the present invention are not limited thereto. A tandem OLED according to an embodiment of the present invention is manufactured by connecting a plurality of stacks through charge generation layers.

In Tandem OLED according to an embodiment of the present invention, the same compound is used in the emitting layer and the electron transport layer of each of the 2 stacks, but is not limited thereto.

[Example 1] tandem OLED with two stacks connected

A tandem OLED with two stacks connected was manufactured with the structure of first electrode/hole transport region/emitting layer/electron transport region/charge generation region/hole transport region/emitting layer/electron transport region/electron injection layer/second electrode.

Specifically, $N^1$-(naphthalen-2-yl)-$N^4$, $N^4$-bis(4-(naphthalen-2-yl(phenyl)amino)phenyl)-$N^1$-phenylbenzene-1,4-diamine (hereinafter abbreviated as 2-TNATA) and HATCN were used on the ITO layer (first electrode) formed on the glass substrate, but HATCN was doped in a weight ratio of 90:10 to form a hole injection layer having a thickness of 60 nm. A hole transport layer was formed on the hole injection layer by vacuum depositing N,N'-bis(1-naphthalenyl)-N,N'-bis-phenyl-(1,1'-biphenyl)-4,4'-diamine (hereinafter abbreviated as NPB) to a thickness of 145 nm.

Subsequently, 4,4'-Bis(2,2-diphenylethenyl)-1,1'-biphenyl (hereinafter abbreviated as DPVBi) was used as a host material for the emitting layer and 4,4'-bis (9-ethyl-3-carbazovinylene)-1,1'-biphenyl (hereinafter abbreviated as BCzVBi) was used as a dopant material on the hole transport layer, but the dopant was doped in a weight ratio of 95:5 to form an emitting layer having a thickness of 115 nm.

Next, on the emitting layer, Tris(8-hydroxyquinolinato) aluminium (hereinafter abbreviated as $Alq_3$) was vacuum deposited to a thickness of 90 nm to form an electron transport layer. (hereinafter abbreviated as the first stack)

Next, bathophenanthroline (hereinafter abbreviated as Bphen) and Li are used to connect the two stacks, but Li is doped with a weight of 97:3 to form an n-type charge generation layer with a thickness of 50 nm, and the compound P-1 of the present invention and HATCN were used on the n-type charge generation layer, but HATCN was doped in a weight ratio of 90:10 to form a p-type charge generation layer having a thickness of 65 nm.

A hole transport layer, an emitting layer, and an electron transport layer identical to those formed in the first stack were sequentially formed on the p-type charge generation layer. (hereinafter abbreviated as the second stack)

Then, lithium fluoride (hereinafter abbreviated as LiF) was vacuum deposited to a thickness of 6 nm as an electron injection layer, and then Ag: Mg was deposited to a thickness of 150 nm to form a second electrode, thereby manufacturing a tandem OLED.

[Example 2] to [Example 40]

An organic electronic element was manufactured in the same manner as in Example 1, except that the compounds shown in Table 3 were used as materials for the n-type charge generation layer and the p-type charge generation layer.

[Comparative Example 1] to [Comparative Example 6]

An organic electronic element was manufactured in the same manner as in Example 1, except that Comparative Compounds A to Comparative Compounds C were used as materials for the n-type charge generation layer and the p-type charge generation layer.

[Comparative Compound A]

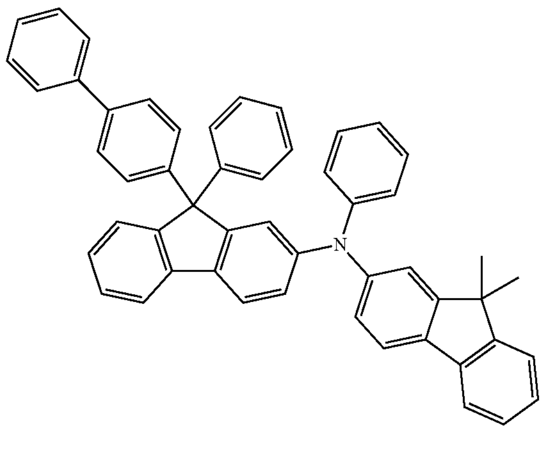

-continued

[Comparative Compound B]

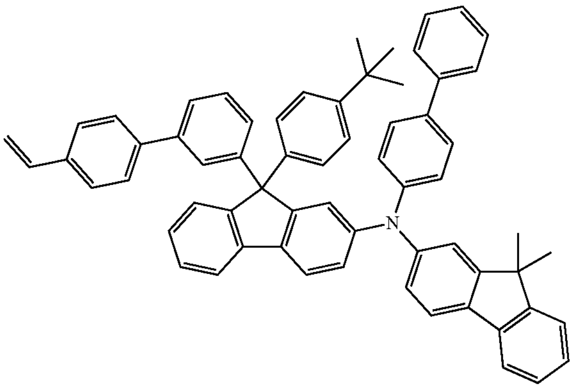

[Comparative Compound C]

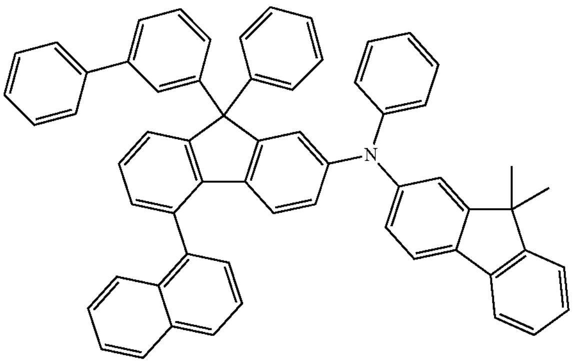

[Example 41] to [Example 56]

An organic electronic element was fabricated in the same manner as in Example 1, except that the compounds of the present invention described in Table 4 were used as materials for the p-type charge generation layer and the hole transport layer of the second stack.

[Comparative Example 7] to [Comparative Example 9]

An organic electronic element was fabricated in the same manner as in Example 41, except that Comparative Compounds A to Comparative Compounds C described in Table 4 were used as materials for the hole transport layer of the second stack.

To the OLEDs of examples and comparative examples prepared as described above, a forward bias direct current voltage was applied, and electroluminescent(EL) properties were measured using PR-650 of Photoresearch Co., and T95 life was measured using a life measuring apparatus manufactured by McScience Inc. with a reference luminance of 1,500 cd/$m^2$. Table 3 and Table 4 show the results of device fabrication and evaluation.

TABLE 3

| | charge generation area | | | | | | |
|---|---|---|---|---|---|---|---|
| | n-type charge generation layer | p-type charge generation layer | Voltage (V) | Current Density ($mA/cm^2$) | Brightness ($cd/m^2$) | Efficiency (cd/A) | T(95) |
| Comparative example (1) | BPhen | Comparative compound A | 12.6 | 14.9 | 1500.0 | 10.1 | 60.2 |
| Comparative example (2) | BPhen | Comparative compound B | 14.2 | 17.4 | 1500.0 | 8.6 | 42.8 |
| Comparative example (3) | BPhen | Comparative compound C | 13.1 | 16.1 | 1500.0 | 9.3 | 57.9 |
| Comparative example (4) | N-35 | Comparative compound A | 11.9 | 13.8 | 1500.0 | 10.9 | 62.5 |
| Comparative example (5) | N-35 | Comparative compound B | 13.7 | 17.2 | 1500.0 | 8.7 | 44.3 |
| Comparative example (6) | N-35 | Comparative compound C | 12.5 | 15.0 | 1500.0 | 10.0 | 59.7 |
| Example (1) | Bphen | P-1 | 8.8 | 11.0 | 1500.0 | 13.6 | 77.6 |
| Example (2) | N-35 | P-1 | 7.8 | 9.5 | 1500.0 | 15.8 | 86.4 |
| Example (3) | N-35 | P-2 | 7.9 | 9.9 | 1500.0 | 15.1 | 82.5 |
| Example (4) | N-35 | P-3 | 7.9 | 9.9 | 1500.0 | 15.2 | 85.5 |
| Example (5) | N-35 | P-4 | 8.0 | 9.9 | 1500.0 | 15.2 | 85.7 |
| Example (6) | N-35 | P-5 | 8.1 | 9.6 | 1500.0 | 15.6 | 83.9 |
| Example (7) | N-35 | P-6 | 7.9 | 9.7 | 1500.0 | 15.5 | 82.1 |
| Example (8) | N-35 | P-7 | 7.9 | 9.7 | 1500.0 | 15.5 | 83.7 |
| Example (9) | N-35 | P-8 | 8.1 | 9.8 | 1500.0 | 15.3 | 83.3 |
| Example (10) | N-35 | P-9 | 8.2 | 10.1 | 1500.0 | 14.9 | 81.6 |
| Example (11) | N-35 | P-10 | 8.3 | 10.4 | 1500.0 | 14.4 | 81.2 |
| Example (12) | N-35 | P-11 | 8.3 | 10.3 | 1500.0 | 14.6 | 80.1 |
| Example (13) | N-35 | P-12 | 8.4 | 10.1 | 1500.0 | 14.8 | 82.0 |
| Example (14) | N-35 | P-13 | 8.3 | 10.1 | 1500.0 | 14.9 | 80.3 |
| Example (15) | N-35 | P-14 | 8.3 | 10.0 | 1500.0 | 15.0 | 81.9 |
| Example (16) | N-35 | P-15 | 8.3 | 10.1 | 1500.0 | 14.8 | 80.6 |
| Example (17) | N-35 | P-16 | 8.4 | 10.0 | 1500.0 | 15.0 | 81.4 |
| Example (18) | N-37 | P-1 | 7.5 | 9.2 | 1500.0 | 16.3 | 90.6 |
| Example (19) | N-37 | P-2 | 7.6 | 9.7 | 1500.0 | 15.4 | 87.8 |
| Example (20) | N-37 | P-3 | 7.6 | 9.7 | 1500.0 | 15.5 | 90.1 |
| Example (21) | N-37 | P-4 | 7.7 | 9.6 | 1500.0 | 15.7 | 88.9 |
| Example (22) | N-37 | P-5 | 7.8 | 9.7 | 1500.0 | 15.4 | 87.3 |
| Example (23) | N-37 | P-6 | 7.7 | 9.7 | 1500.0 | 15.5 | 89.3 |
| Example (24) | N-37 | P-7 | 7.7 | 9.4 | 1500.0 | 15.9 | 88.2 |
| Example (25) | N-37 | P-8 | 7.9 | 9.5 | 1500.0 | 15.8 | 88.3 |
| Example (26) | N-37 | P-9 | 8.0 | 9.8 | 1500.0 | 15.3 | 86.1 |
| Example (27) | N-37 | P-10 | 8.1 | 9.9 | 1500.0 | 15.1 | 85.9 |
| Example (28) | N-37 | P-11 | 8.1 | 9.9 | 1500.0 | 15.2 | 84.7 |
| Example (29) | N-37 | P-12 | 8.2 | 9.8 | 1500.0 | 15.3 | 85.5 |
| Example (30) | N-37 | P-13 | 8.1 | 9.9 | 1500.0 | 15.2 | 85.9 |
| Example (31) | N-37 | P-14 | 8.1 | 10.0 | 1500.0 | 15.0 | 85.1 |
| Example (32) | N-37 | P-15 | 8.1 | 9.9 | 1500.0 | 15.1 | 86.5 |
| Example (33) | N-37 | P-16 | 8.2 | 10.0 | 1500.0 | 15.0 | 86.0 |
| Example (34) | N-59 | P-1 | 8.0 | 10.0 | 1500.0 | 15.0 | 83.8 |
| Example (35) | N-59 | P-2 | 8.2 | 10.3 | 1500.0 | 14.6 | 82.9 |
| Example (36) | N-59 | P-6 | 8.3 | 10.2 | 1500.0 | 14.7 | 83.1 |
| Example (37) | N-59 | P-9 | 8.4 | 10.6 | 1500.0 | 14.2 | 81.4 |
| Example (38) | N-59 | P-11 | 8.5 | 10.6 | 1500.0 | 14.1 | 81.7 |
| Example (39) | N-59 | P-14 | 8.5 | 10.7 | 1500.0 | 14.0 | 81.3 |
| Example (40) | N-59 | P-15 | 8.6 | 10.6 | 1500.0 | 14.1 | 81.2 |

As can be seen from the results of Table 3, in the case of manufacturing a tandem OLED using the compounds represented by Formulas P-1 to P-16 of the present invention as a material for the p-type charge generation layer, the driving voltage, efficiency and lifespan of the organic electronic element can be improved compared to Comparative Examples using Comparative Compound A to Comparative Compound C having a similar basic skeleton to the compound of the present invention. In the case of the p-type charge generation layer, the role of hole transfer from the p-type charge generation layer to the hole transport layer of the second stack and the Charge separation ability to quickly move electrons to the n-type charge generation layer are required, Charge separation ability of the compound of the present invention is superior to that of Comparative Compound A to Comparative Compound C.

Additionally comparing Example 1 and Example 2, it can be confirmed that the materials formed in the n-type charge generation layer are Bphen and the compound represented by Formula 2, respectively, and have different structures, and the performance of the device is improved when the compound represented by Formula 2 is applied to the n-type charge generation layer. When the compound represented by Formula 2 is used as the n-type charge generation layer and the compounds represented by Formulas P-1 to P-16 are used as the p-type charge generation layer, the performance of the device is improved by maximizing the charge balance of the device.

TABLE 4

| | p-type charge generation layer | 2nd stack hole transport layer | Voltage | Current Density ($mA/cm^2$) | Brightness ($cd/m^2$) | Efficiency (cd/A) | T(95) |
|---|---|---|---|---|---|---|---|
| Comparative example(7) | P-1 | Comparative compound A | 11.4 | 13.4 | 1500.0 | 11.2 | 67.4 |
| Comparative example(8) | P-1 | Comparative compound B | 13.8 | 16.3 | 1500.0 | 9.2 | 44.6 |
| Comparative example(9) | P-1 | Comparative compound C | 12.5 | 13.8 | 1500.0 | 10.9 | 63.8 |
| Example (41) | P-1 | | 7.5 | 7.6 | 1500.0 | 19.7 | 117.8 |
| Example (42) | P-2 | | 7.6 | 8.8 | 1500.0 | 17.1 | 113.0 |
| Example (43) | P-3 | | 7.6 | 8.5 | 1500.0 | 17.7 | 115.4 |
| Example (44) | P-4 | | 7.7 | 8.8 | 1500.0 | 17.0 | 110.4 |
| Example (45) | P-5 | | 7.8 | 8.5 | 1500.0 | 17.7 | 115.5 |
| Example (46) | P-6 | | 7.6 | 8.4 | 1500.0 | 17.8 | 112.0 |
| Example (47) | P-7 | | 7.6 | 8.9 | 1500.0 | 16.9 | 113.0 |
| Example (48) | P-8 | | 7.8 | 8.9 | 1500.0 | 16.8 | 114.4 |
| Example (49) | P-9 | | 7.9 | 9.5 | 1500.0 | 15.8 | 105.0 |
| Example (50) | P-10 | | 7.9 | 10.2 | 1500.0 | 14.7 | 106.9 |
| Example (51) | P-11 | | 7.9 | 10.1 | 1500.0 | 14.8 | 109.6 |
| Example (52) | P-12 | | 8.0 | 10.1 | 1500.0 | 14.9 | 109.7 |
| Example (53) | P-13 | | 7.9 | 9.8 | 1500.0 | 15.3 | 106.0 |
| Example (54) | P-14 | | 7.9 | 9.6 | 1500.0 | 15.7 | 105.5 |
| Example (55) | P-15 | | 7.9 | 10.1 | 1500.0 | 14.9 | 108.3 |
| Example (56) | P-16 | | 8.0 | 10.3 | 1500.0 | 14.6 | 108.2 |

In the case of Table 4, it is an experiment to confirm the interaction between the p-type charge generation layer and the hole transport layer of the second stack. As can be seen in Comparative Examples 7 to 9 and Examples 41 to 56 of the present invention, when compounds represented by Formulas P-1 to P-16 are included in the p-type charge generation layer and the hole transport layer of the second stack, Charge balance of the device is maximized and the performance of the device appears to be improved.

As a result, it can be confirmed that the compounds of the present invention represented by Formulas P-1 to Formulas P-16 have better device performance than other comparative compounds not described herein.

[Example 57] Green organic light emitting device (hole transport layer)

$N^1$-(naphthalen-2-yl)-$N^4$, $N^4$-bis(4-(naphthalen-2-yl(phenyl)amino)phenyl)-$N^1$-phenylbenzene-1,4-diamine (hereinafter abbreviates as 2-TNATA) was vacuum deposited on the ITO layer (anode) formed on the glass substrate to form a hole injection layer having a thickness of 60 nm. A hole transport layer was formed by vacuum depositing the inventive compound P-1 on the hole injection layer to a thickness of 60 nm.

Then, 4,4'-N,N'-dicarbazole-biphenyl (hereinafter abbreviates as CBP) as a host material of the emitting layer on the hole transport layer, $Ir(ppy)_3$ [tris(2-phenylpyridine)-iridium] was used as a dopant material, and the dopant was doped in a weight ratio of 90:10 to form an emitting layer having a thickness of 30 nm.

Next, (1,1'-biphenyl-4-olato)bis(2-methyl-8-quinolinolato)aluminum (hereinafter abbreviates as BAlq) was vacuum deposited on the emitting layer to form a hole blocking layer having a thickness of 10 nm, and an electron transport layer was formed by vacuum depositing bis(10-hydroxybenzo[h]quinolinato)beryllium (hereinafter abbreviates as $BeBq_2$) on the hole blocking layer to a thickness of 40 nm. Thereafter, LiF was deposited on the electron transport layer to form an electron injection layer having a thickness of 0.2 nm, and then Al was deposited to form a cathode having a thickness of 150 nm.

[Example 58] to [Example 72]

An organic electroluminescent device was manufactured in the same manner as in Example 57, except that the compound of the present invention shown in Table 5 was used instead of the compound P-1 of the present invention as the hole transport layer material.

[Comparative Example 10] to [Comparative Example 12]

An organic light emitting device was manufactured in the same manner as in Example 57, except that Comparative Compounds A to C were used as the hole transport layer material instead of Compound P-1 of the present invention.

To the OLEDs manufactured by Examples 57 to 72 and Comparative Examples 10 to 12 of the present invention, a forward bias direct current voltage was applied, and electroluminescent(EL) properties were measured using PR-650 of Photoresearch Co., and T95 life was measured using a life measuring apparatus manufactured by McScience Inc. with a reference luminance of 5,000 $cd/m^2$. Table 5 shows the results of device fabrication and evaluation.

TABLE 5

| | Compound | Voltage (V) | Current Density ($mA/cm^2$) | Brightness ($cd/m^2$) | Efficiency (cd/A) | T(95) |
|---|---|---|---|---|---|---|
| Comparative example(10) | Comparative compound A | 5.7 | 22.4 | 5000.0 | 22.3 | 80.2 |
| Comparative example(11) | Comparative compound B | 6.4 | 26.0 | 5000.0 | 19.2 | 73.4 |
| Comparative example(12) | Comparative compound C | 5.9 | 23.5 | 5000.0 | 21.3 | 79.6 |
| Example (57) | P-1 | 5.3 | 13.1 | 5000.0 | 38.2 | 107.5 |
| Example (58) | P-2 | 5.4 | 13.6 | 5000.0 | 36.8 | 104.8 |
| Example (59) | P-3 | 5.4 | 13.6 | 5000.0 | 36.9 | 104.8 |
| Example (60) | P-4 | 5.5 | 13.5 | 5000.0 | 37.1 | 103.7 |
| Example (61) | P-5 | 5.5 | 13.9 | 5000.0 | 35.9 | 103.6 |
| Example (62) | P-6 | 5.5 | 13.3 | 5000.0 | 37.6 | 104.7 |
| Example (63) | P-7 | 5.5 | 13.6 | 5000.0 | 36.8 | 104.4 |
| Example (64) | P-8 | 5.5 | 13.9 | 5000.0 | 35.9 | 103.9 |
| Example (65) | P-9 | 5.5 | 15.6 | 5000.0 | 32.1 | 102.7 |
| Example (66) | P-10 | 5.5 | 14.3 | 5000.0 | 35.0 | 101.6 |
| Example (67) | P-11 | 5.5 | 15.7 | 5000.0 | 31.9 | 101.4 |
| Example (68) | P-12 | 5.6 | 15.4 | 5000.0 | 32.4 | 102.5 |
| Example (69) | P-13 | 5.5 | 15.9 | 5000.0 | 31.4 | 101.5 |

TABLE 5-continued

| | Compound | Voltage (V) | Current Density (mA/cm²) | Brightness (cd/m²) | Efficiency (cd/A) | T(95) |
|---|---|---|---|---|---|---|
| Example (70) | P-14 | 5.5 | 14.2 | 5000.0 | 35.3 | 100.7 |
| Example (71) | P-15 | 5.6 | 14.9 | 5000.0 | 33.6 | 101.3 |
| example(72) | P-16 | 5.6 | 15.3 | 5000.0 | 32.8 | 101.8 |

As can be seen from the results of Table 5, when a green organic light emitting device is manufactured by using the compound P-1 to compound P-16 of the present invention as a hole transport layer material in an organic light emitting device, compared to the case of using Comparative Compound A to Comparative Compound C, the driving voltage was lowered and the efficiency and lifespan were remarkably improved.

As a result, it can be seen that the compounds of the present invention represented by Formulas P-1 to P-16 exhibit significant effects compared to other comparative compounds not described herein.

These results suggests that even for compounds with similar molecular components, the properties of compounds such as hole properties, light efficiency properties, energy level, hole injection and mobility properties, Charge balance between holes and electrons, volume density and distance between molecules, etc. can vary significantly to the extent that it is difficult to predict, depending on the type and position of the substituent to be substituted, and also the performance of the device may vary due to complex factors, rather than one configuration affecting the overall result of the device.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment.

The scope of the present invention shall be construed on the basis of the accompanying claims, and it shall be construed that all of the technical ideas included within the scope equivalent to the claims belong to the present invention.

What is claimed is:

1. An organic electronic element comprising a first electrode, a second electrode, and an organic layer disposed between the first electrode and the second electrode;

wherein the organic layer includes a first stack and a second stack;

a charge generation region is further comprised between the first stack and the second stack;

the charge generation region comprises an n-type charge generation layer and a p-type charge generation layer;

the n-type charge generation layer faces the first electrode, and the p-type charge generation layer faces the second electrode; and the p-type charge generation layer comprises any one selected from the group consisting of Compounds P-1 to P-16:

P-1

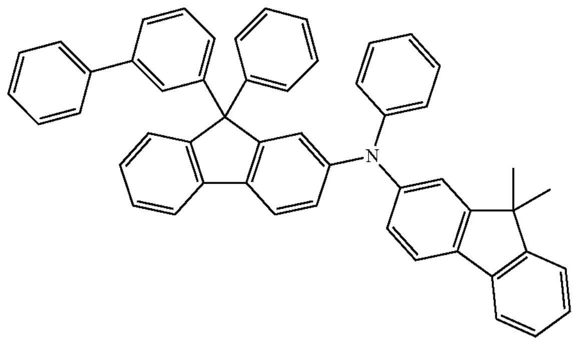

P-2

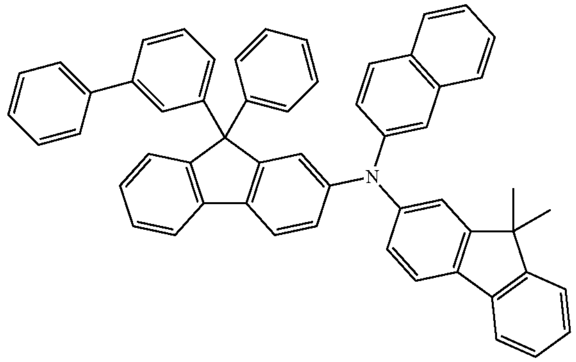

P-3

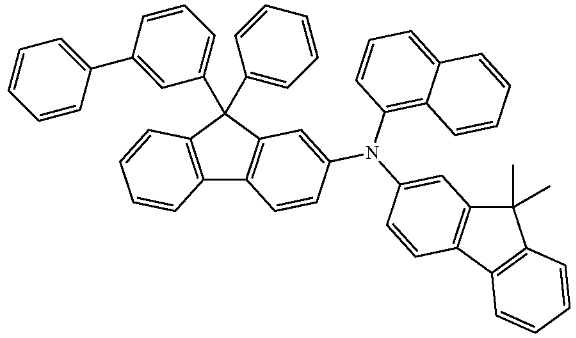

P-4

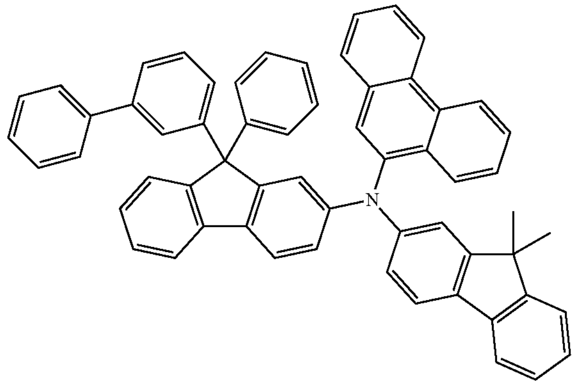

-continued
P-5
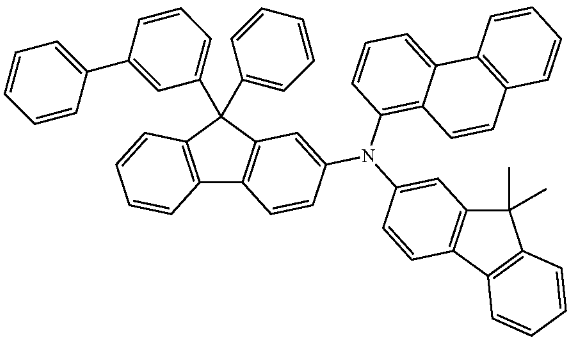
P-6
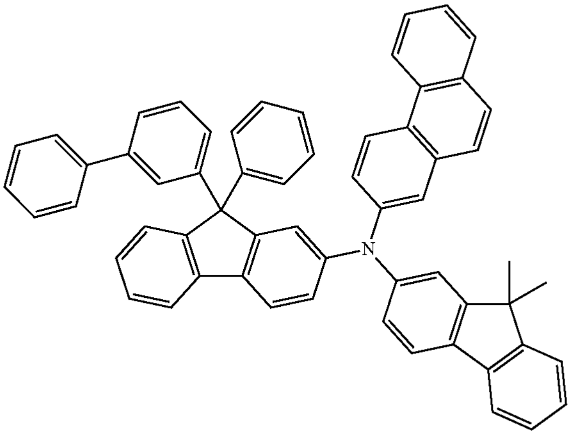
P-7
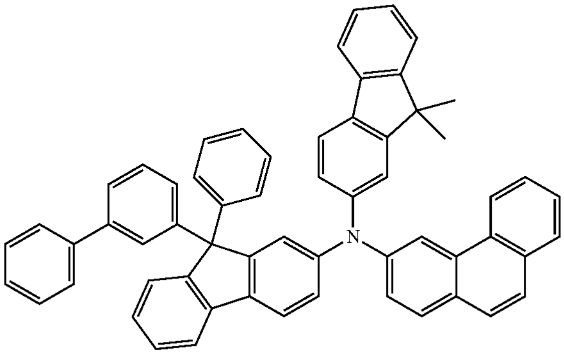
P-8
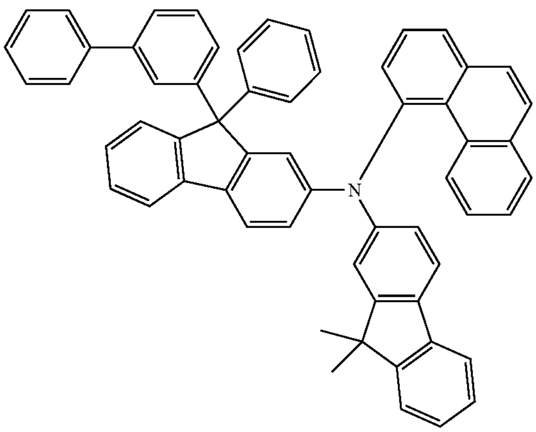
-continued
P-9
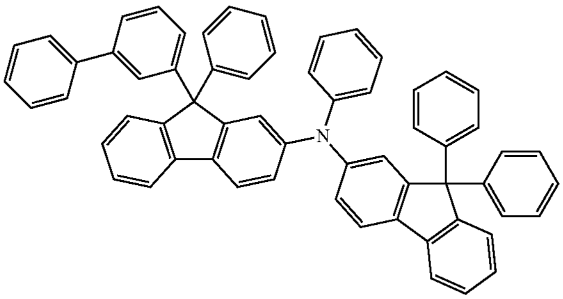
P-10
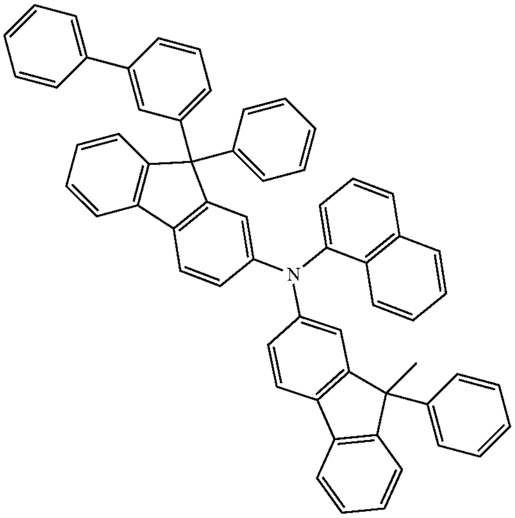
P-11
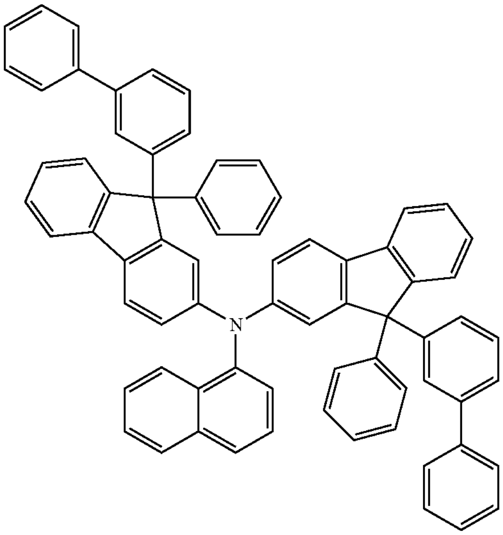

-continued

P-12

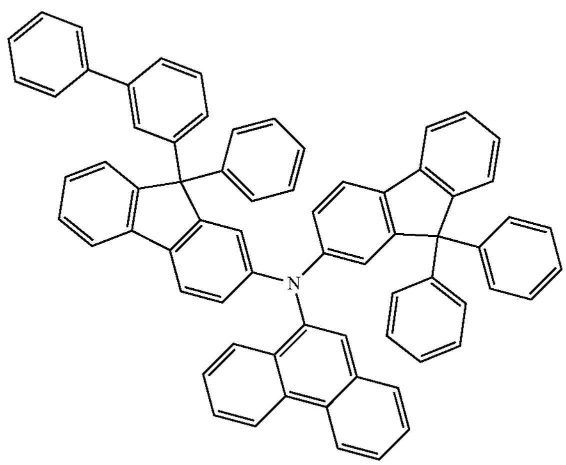

P-13

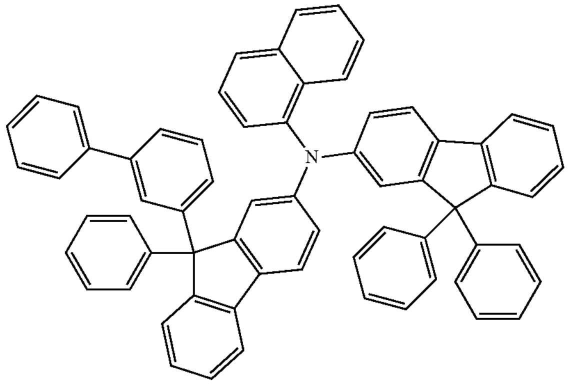

P-14

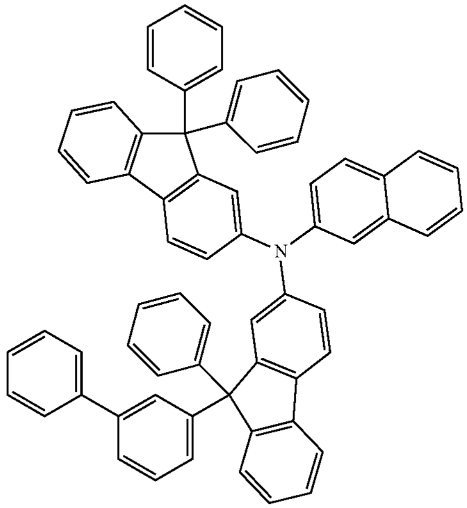

-continued

P-15

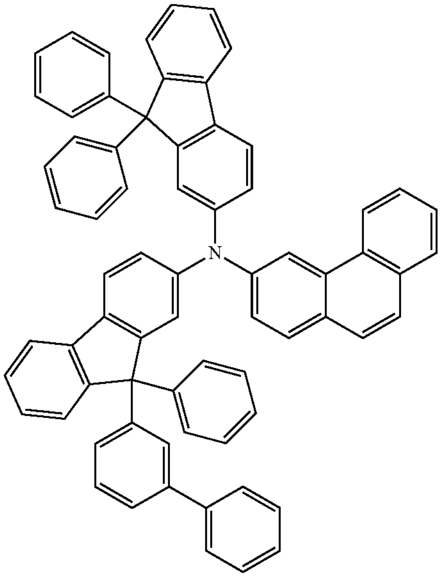

P-16

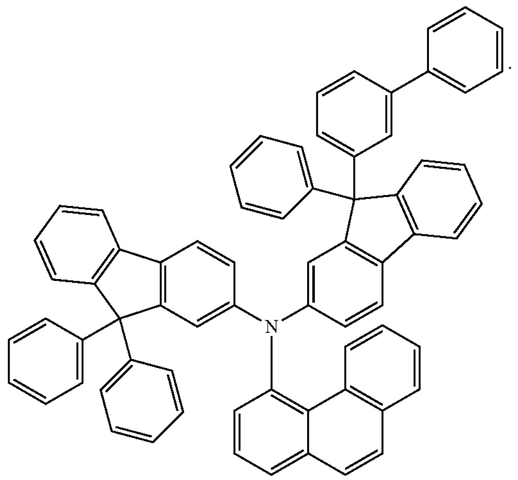

2. The organic electronic element of claim 1, wherein the second stack sequentially comprises a hole transport region, an emitting layer, and an electron transport region, the hole transport region comprises at least one hole transport layer, and the hole transport layer comprises a compound selected from the group consisting of Compounds P-1 to P-16.

3. The organic electronic element of claim 2, comprising an emitting auxiliary layer on the hole transport layer.

4. The organic electronic element of claim 1, wherein the n-type charge generation layer comprises a compound represented by Formula 2:

Formula 2

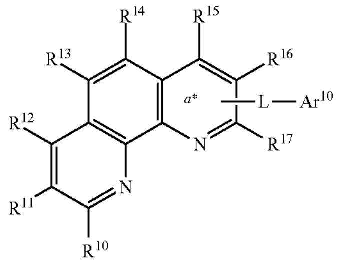

wherein:

1) $R^{10}$, $R^{11}$, $R^{12}$, $R^{13}$, $R^{14}$, $R^{15}$, $R^{16}$ and $R^{17}$ are each independently selected from a group consisting of hydrogen; deuterium; halogen; cyano group; nitro group; a $C_6$-$C_{60}$ aryl group; fluorenyl group; a $C_2$-$C_{60}$ heterocyclic group including at least one heteroatom of O, N, S, Si or P; a $C_3$-$C_{60}$ aliphatic ring; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group, wherein at least one of $R^{15}$, $R^{16}$ and $R^{17}$ is bonded to a* to form a single bond;

2) L is an $C_6$-$C_{60}$ arylene group; or a $C_2$-$C_{60}$ heterocyclic group including at least one heteroatom of O, N, S, Si or P;

3) $Ar^{10}$ is an $C_6$-$C_{60}$ aryl group; or a $C_2$-$C_{60}$ heterocyclic group including at least one heteroatom of O, N, S, Si or P;

wherein the aryl group, arylene group, heterocyclic group, fluorenyl group, aliphatic ring, fused ring group, alkyl group, alkenyl group, alkynyl group, alkoxy group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_1$-$C_{20}$ alkyl group substituted with deuterium; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_3$-$C_{20}$ aliphatic ring group; $C_3$-$C_{20}$ aliphatic ring group substituted with deuterium; $C_2$~$C_{20}$ heterocyclic group; $C_2$~$C_{20}$ heterocyclic group substituted with deuterium; $C_3$~$C_{20}$ cycloalkyl group; $C_7$-$C_{20}$ arylalkyl group; and $C_8$-$C_{20}$ arylalkenyl group; and also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

5. The organic electronic element of claim 4, wherein L is represented by any one of Formulas L-1 to L-16:

[Formula L-1]

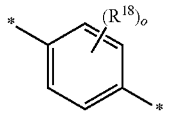

-continued

[Formula L-2]

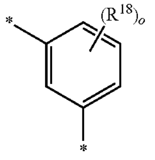

[Formula L-3]

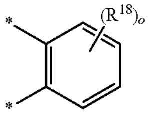

[Formula L-4]

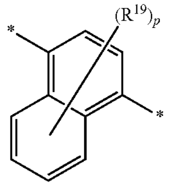

[Formula L-5]

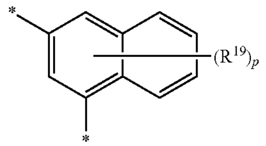

[Formula L-6]

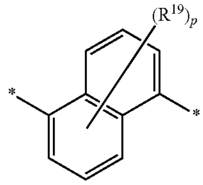

[Formula L-7]

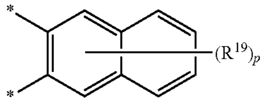

[Formula L-8]

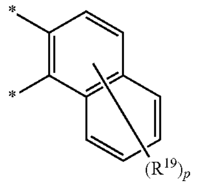

[Formula L-9]

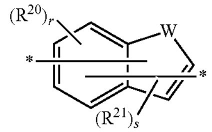

[Formula L-10]

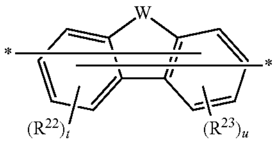

-continued

[Formula L-11]

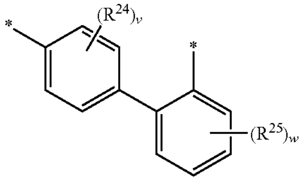

[Formula L-12]

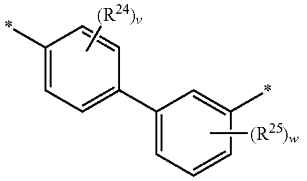

[Formula L-13]

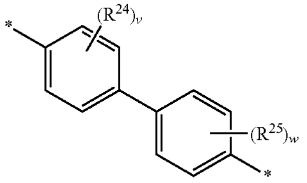

[Formula L-14]

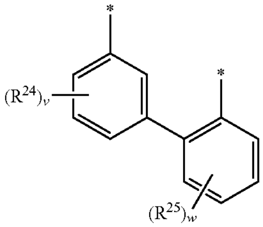

[Formula L-15]

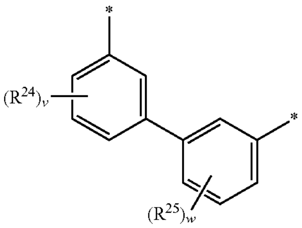

[Formula L-16]

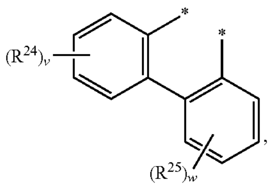

wherein:

1) W is O, S, $C(R^{26})(R^{27})$ or $N(Ar^{12})$,

2) $R^{18}$, $R^{19}$, $R^{20}$, $R^{21}$, $R^{22}$, $R^{23}$, $R^{24}$, $R^{25}$, $R^{26}$ and $R^{27}$ are each independently selected from a group consisting of hydrogen; deuterium; halogen; cyano group; nitro group; a $C_6$-$C_{60}$ aryl group; fluorenyl group; a $C_2$-$C_{60}$ heterocyclic group including at least one heteroatom of O, N, S, Si or P; a $C_3$-$C_{60}$ aliphatic ring; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group, or adjacent groups may be bonded to each other to form a ring;

3) $Ar^{12}$ is an $C_6$-$C_{60}$ aryl group; or a $C_2$-$C_{60}$ heterocyclic group including at least one heteroatom of O, N, S, Si or P;

4) o, r, t, u, v and w are each independently an integer of 0 to 4, p is an integer of 0 to 6, s is an integer of 0 to 2; and 5) * indicates a bonding position.

6. The organic electronic element of claim 4, wherein $Ar^{10}$ is represented by any of Formulas Ar-1 to Ar-15:

[Formula Ar-1]

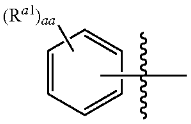

[Formula Ar-2]

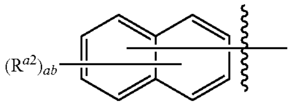

[Formula Ar-3]

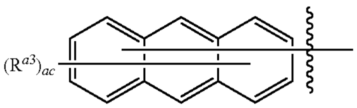

[Formula Ar-4]

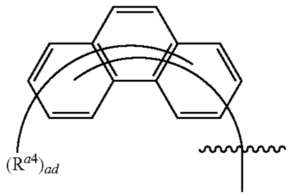

[Formula Ar-5]

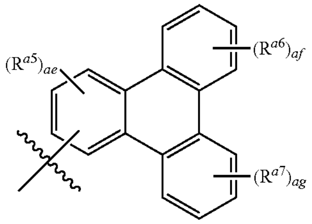

[Formula Ar-6]

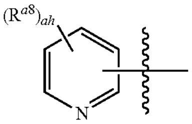

[Formula Ar-7]

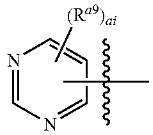

[Formula Ar-8]

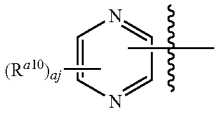

[Formula Ar-9]

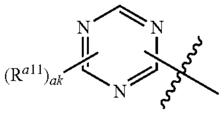

-continued

[Formula Ar-10]

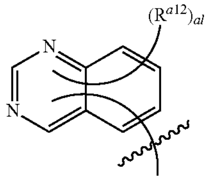

[Formula Ar-11]

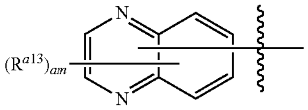

[Formula Ar-12]

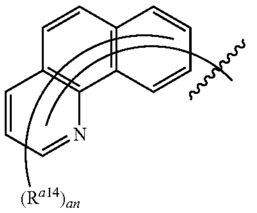

[Formula Ar-13]

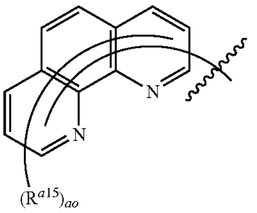

[Formula Ar-14]

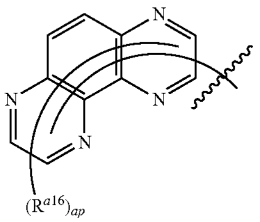

[Formula Ar-15]

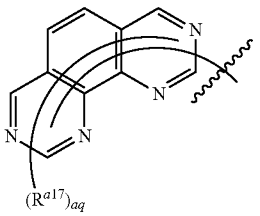

wherein:

1) $R^{a1}$, $R^{a2}$, $R^{a3}$, $R^{a4}$, $R^{a5}$, $R^{a6}$, $R^{a7}$, $R^{a8}$, $R^{a9}$, $R^{a10}$, $R^{a11}$, $R^{a12}$, $R^{a13}$, $R^{a14}$, $R^{a15}$, $Ra^{16}$ and $R^{a17}$ are each independently selected from a group consisting of hydrogen; deuterium; halogen; cyano group; nitro group; a $C_6$-$C_{60}$ aryl group; fluorenyl group; a $C_2$-$C_{60}$ heterocyclic group including at least one heteroatom of O, N, S, Si or P; a $C_3$-$C_{60}$ aliphatic ring; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group, or adjacent groups may be bonded to each other to form a ring, 2) aa, al, am, ap and aq are each independently an integer of 0 to 5, ab and ao are each independently an integer of 0 to 7, ac and ad are each independently an integer of 0 to 9, ae, ai, and aj are each independently an integer of 0 to 3, af, ag and ah are each independently an integer of 0 to 4, ak is an integer of 0 to 2, an is an integer of 0 to 8; and 3)  indicates a bonding position.

7. The organic electronic element of claim 4, wherein Formula 2 is any one selected from the following compounds N-1 to N-92:

N-1

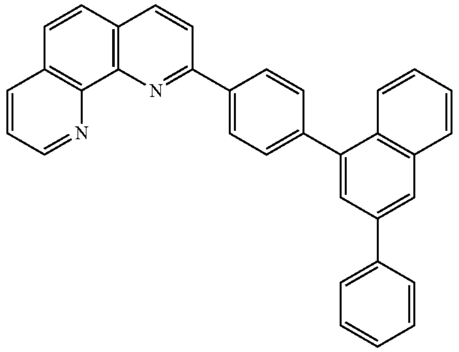

N-2

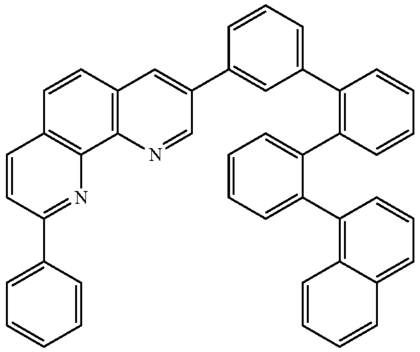

N-3

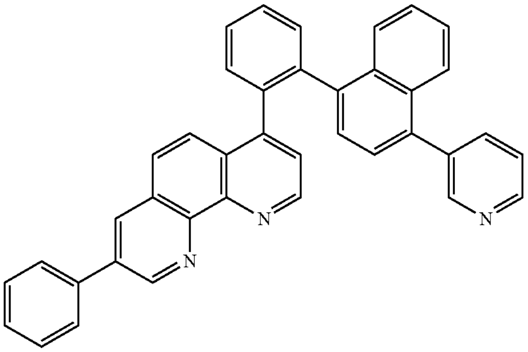

N-4

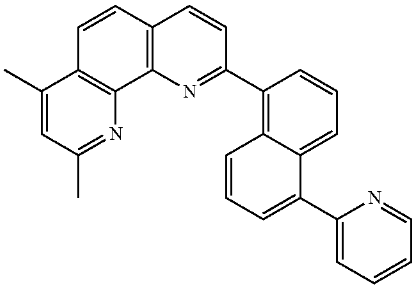

-continued
N-5
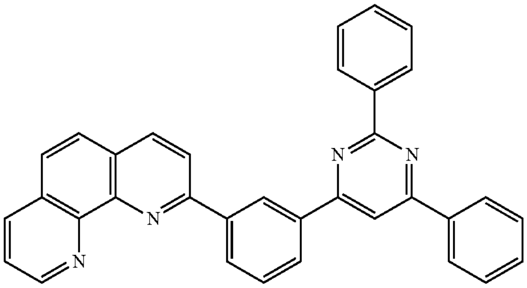
N-6
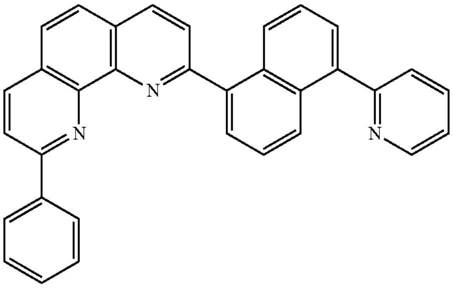
N-7
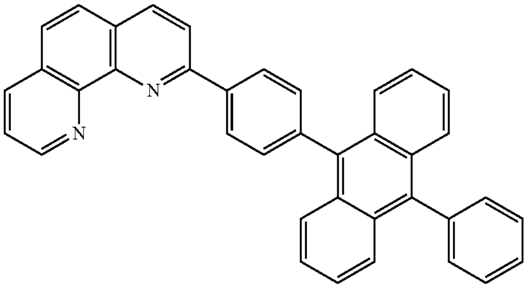
N-8
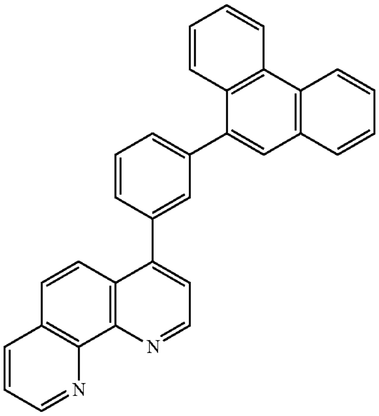
N-9
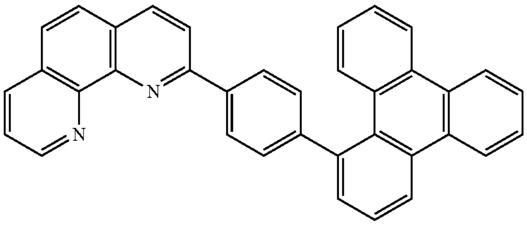
-continued
N-10
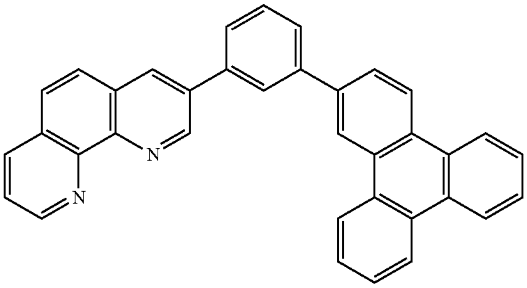
N-11
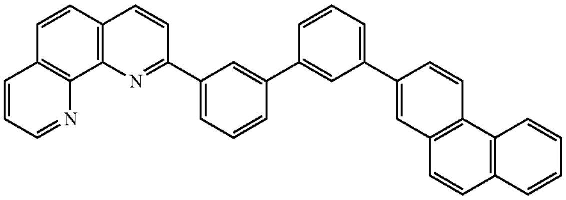
N-12
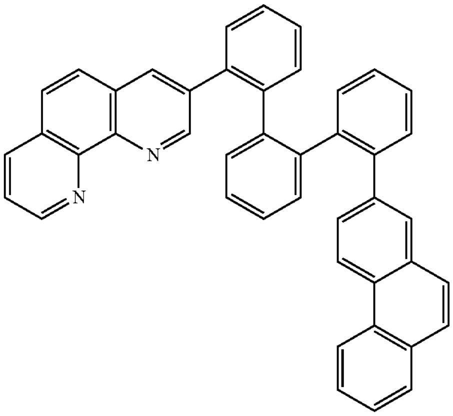
N-13
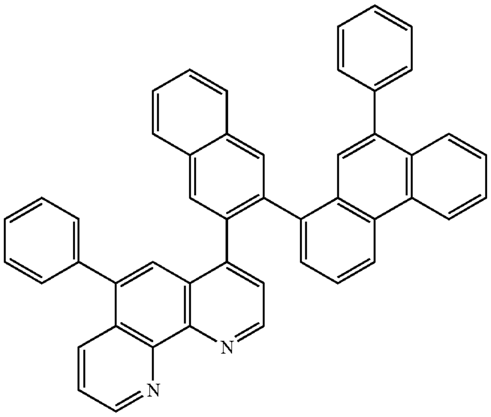

-continued
N-14
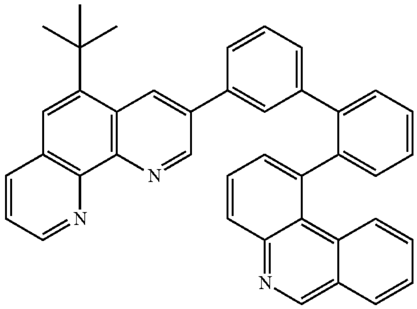
N-15
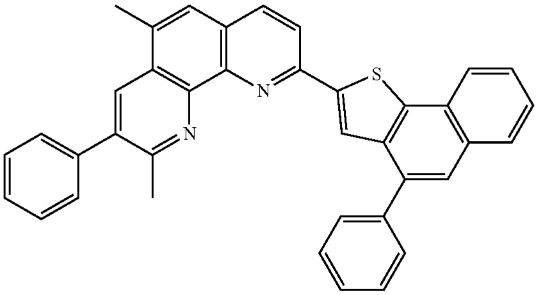
N-16
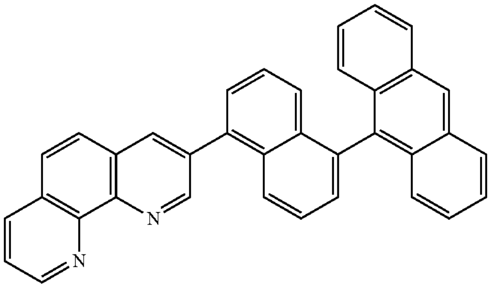
N-17
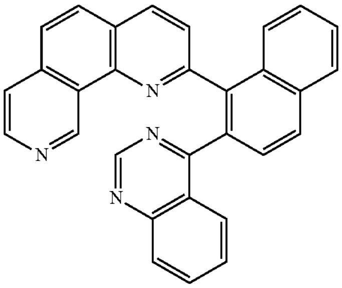
N-18
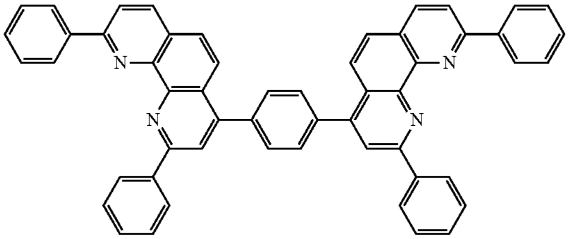
-continued
N-19
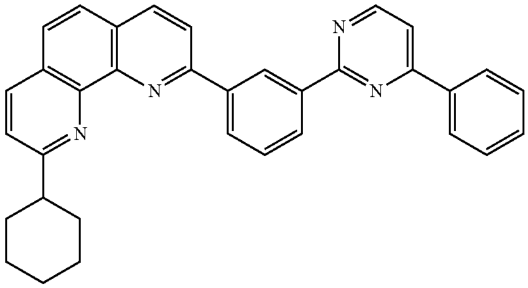
N-20
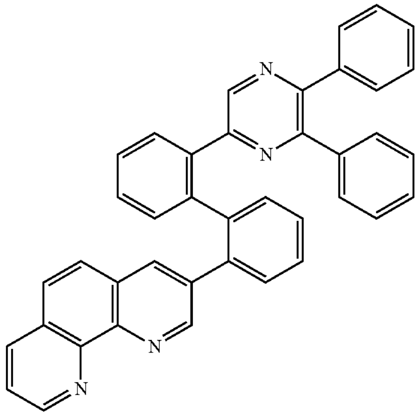
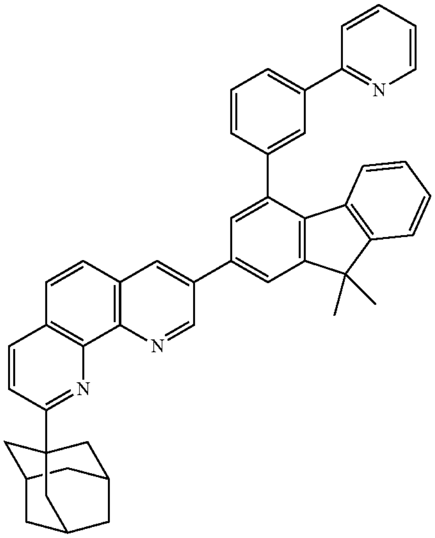

N-22
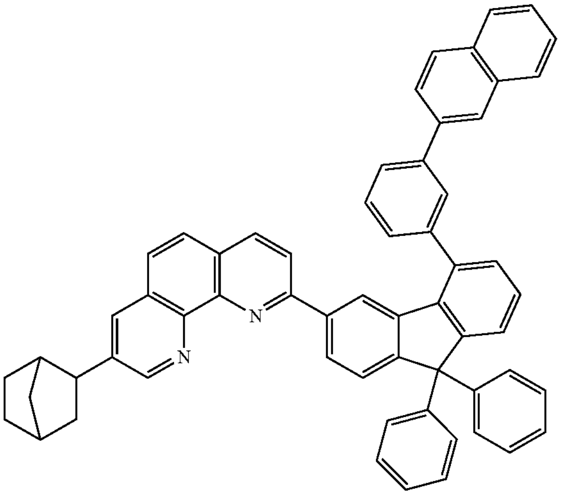
N-23
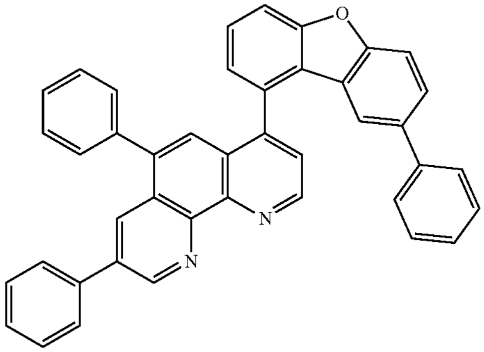
N-24
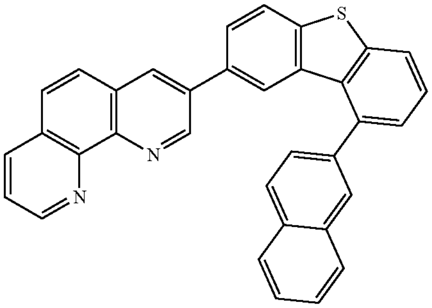
N-25
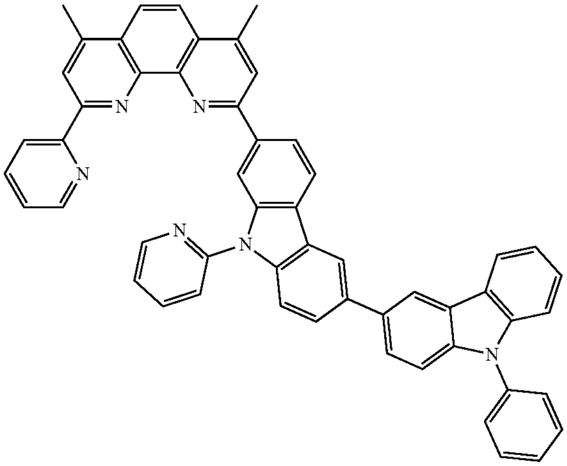
N-26
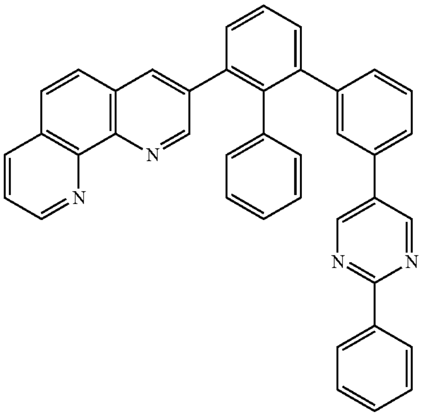
N-27
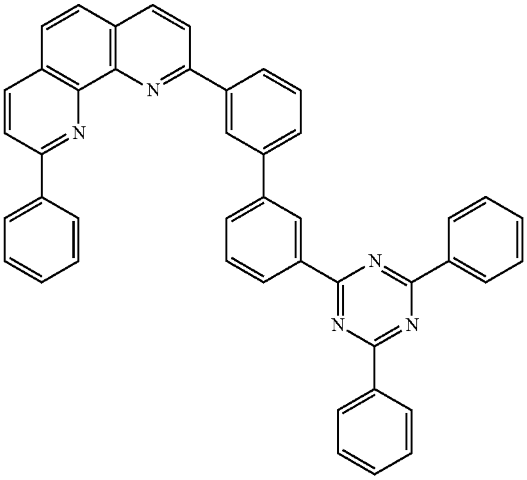

N-28
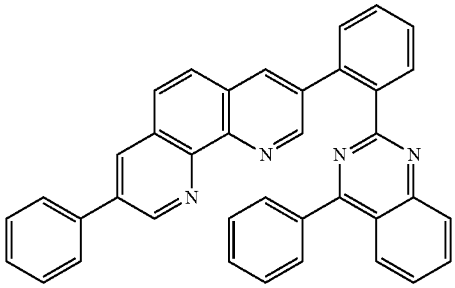
N-29
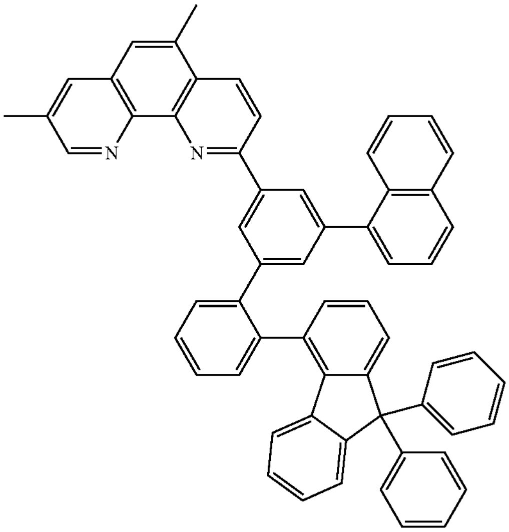
N-30
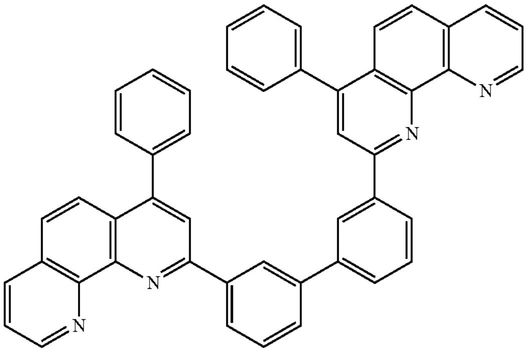
N-31
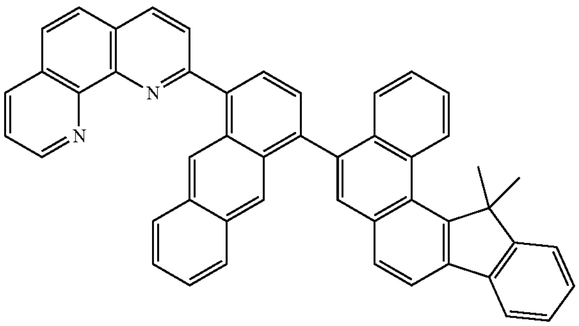
N-32
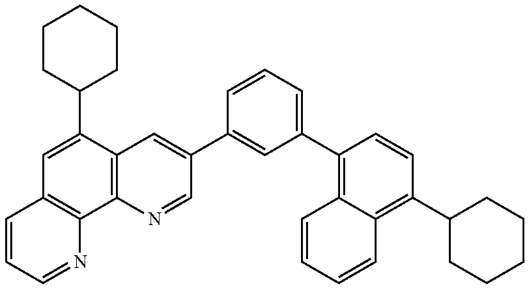
N-33
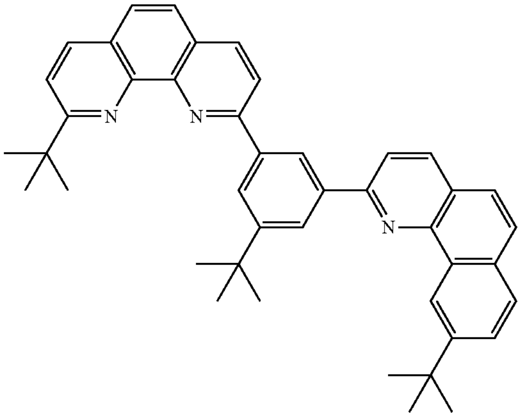
N-34
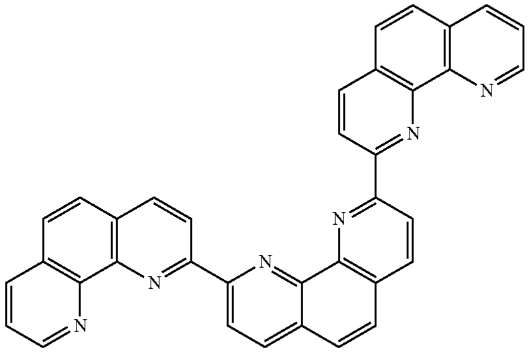
N-35
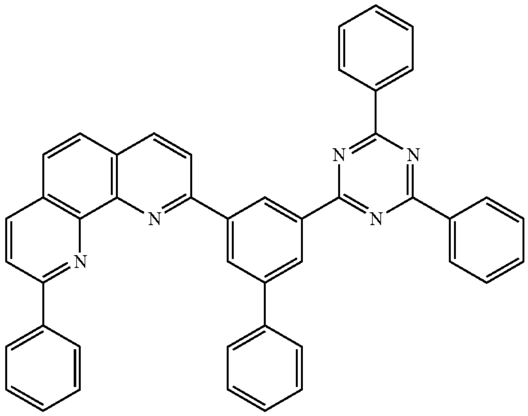

-continued
N-36
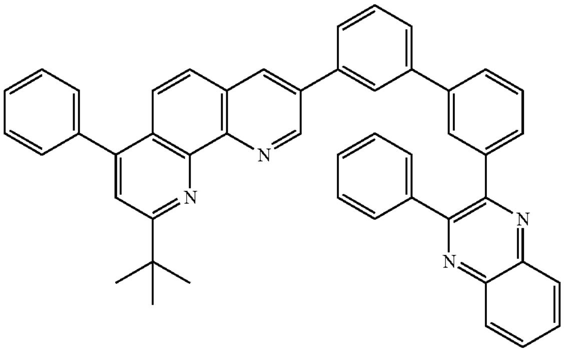
N-37
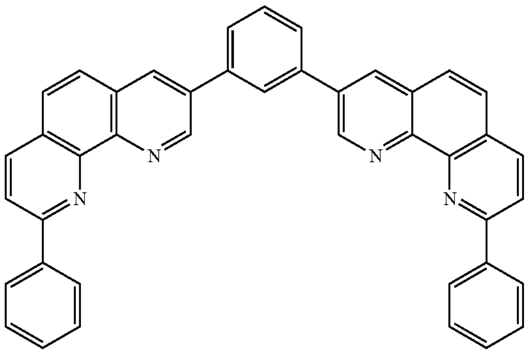
N-38
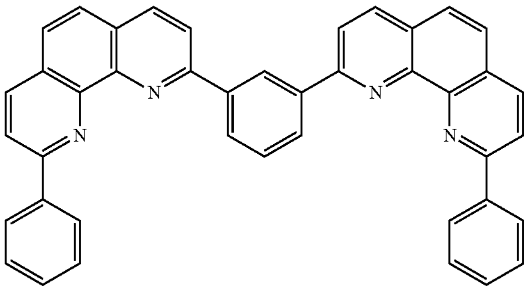
N-39
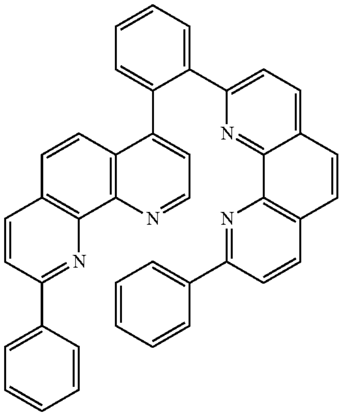
-continued
N-40
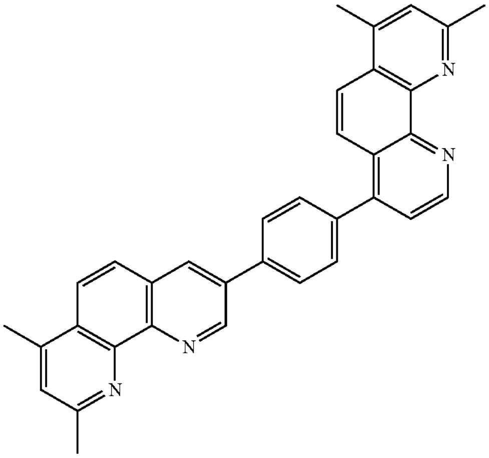
N-41
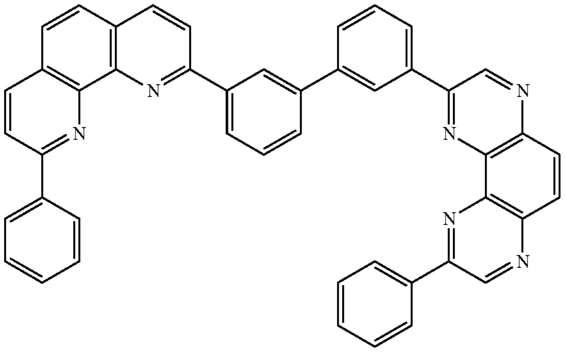
N-42
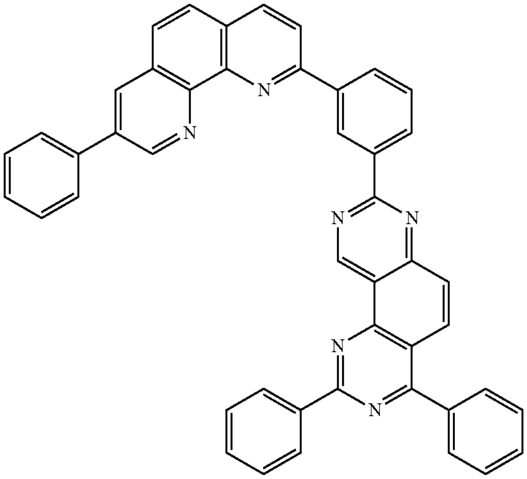

-continued
N-43
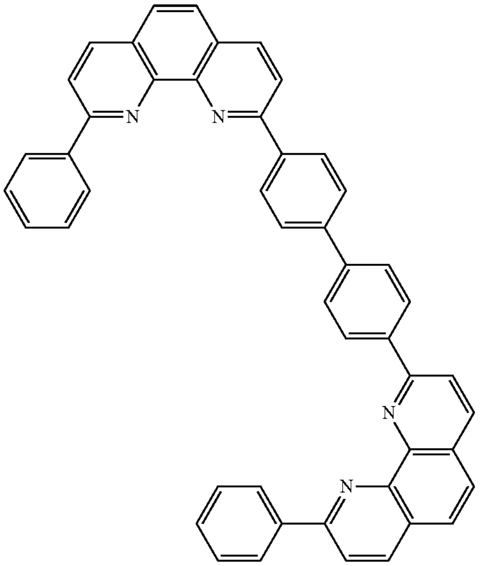
N-44
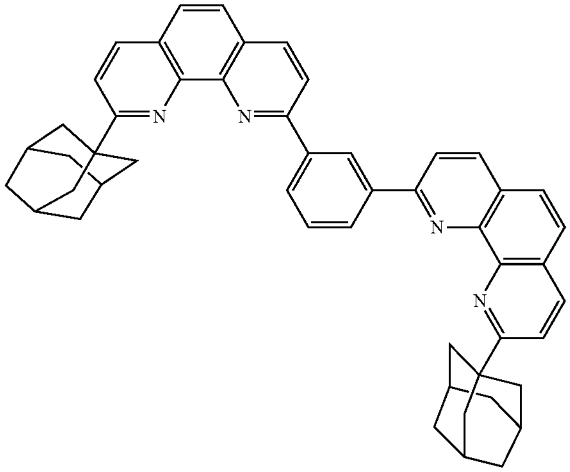
N-45
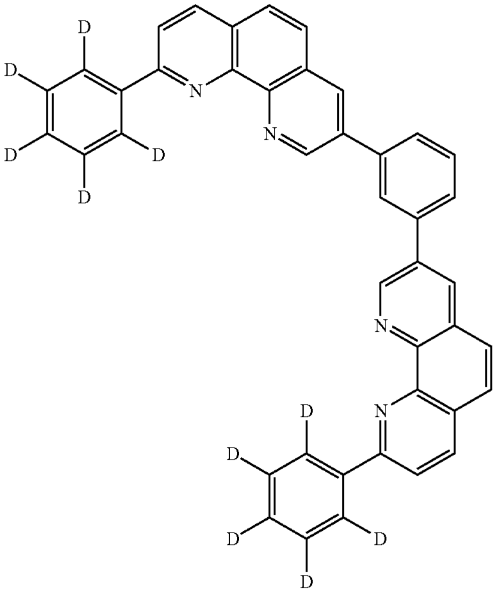
-continued
N-46
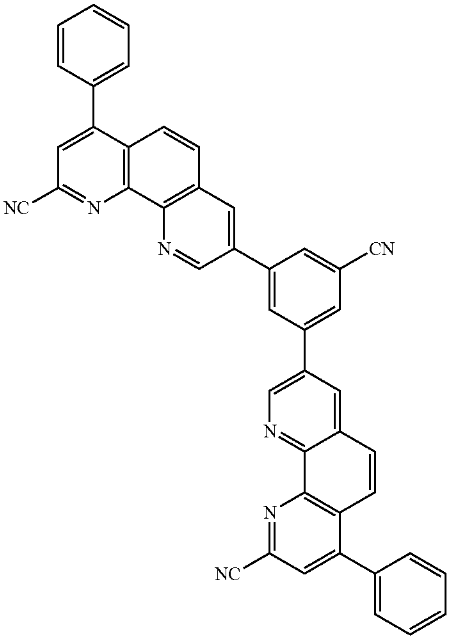
N-47
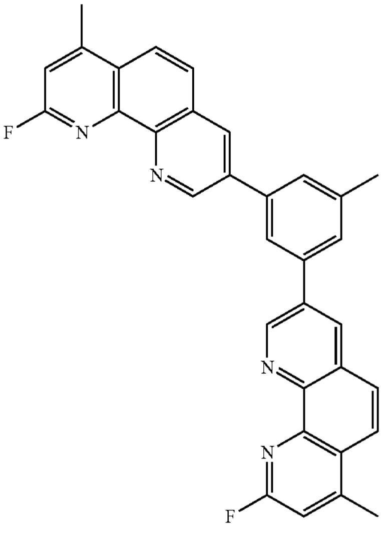

-continued
N-48
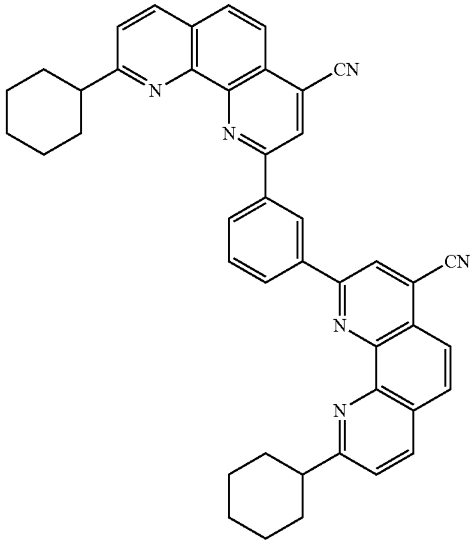
N-49
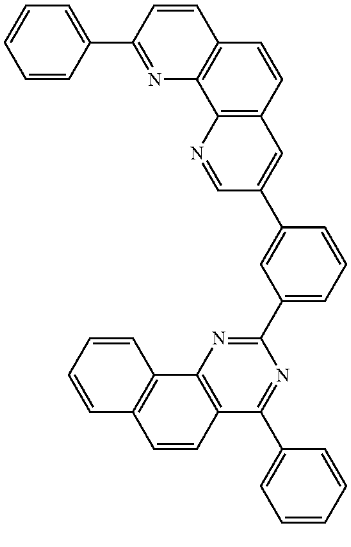
-continued
N-50
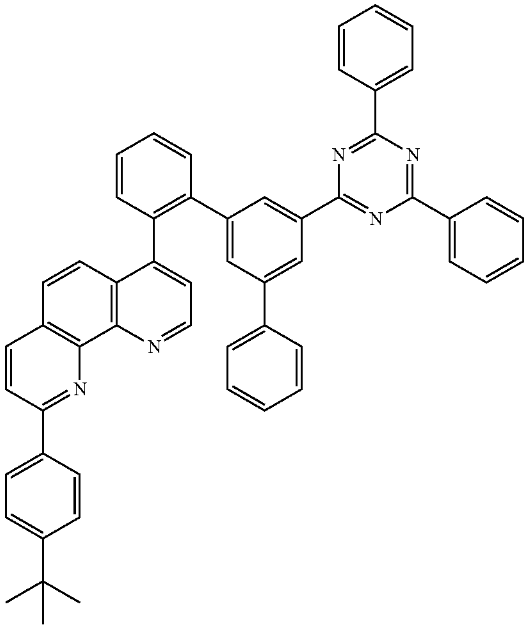
N-51
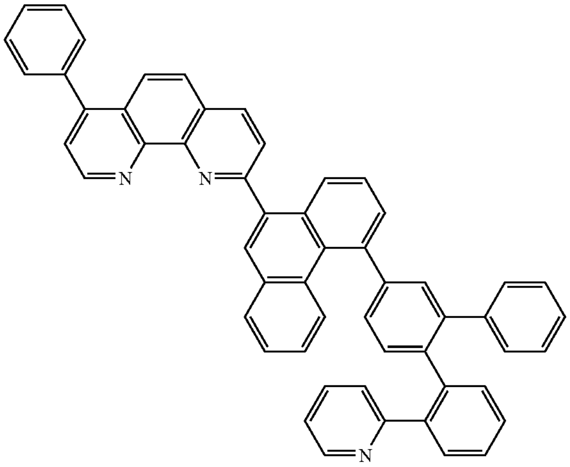
N-52
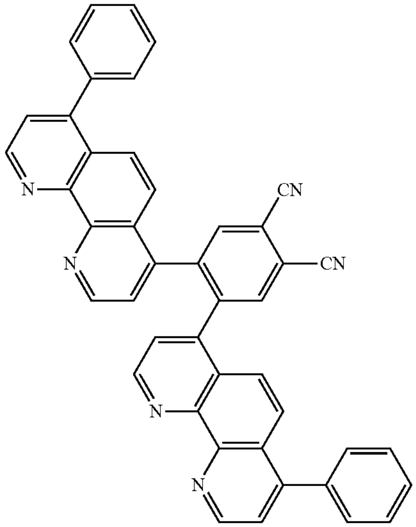

-continued
N-53
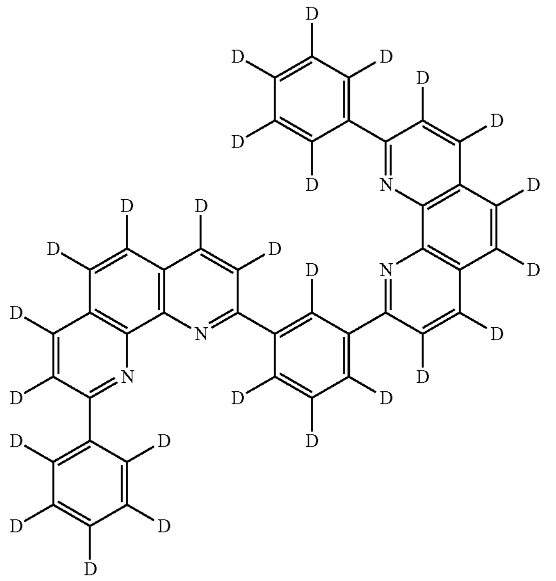
N-54
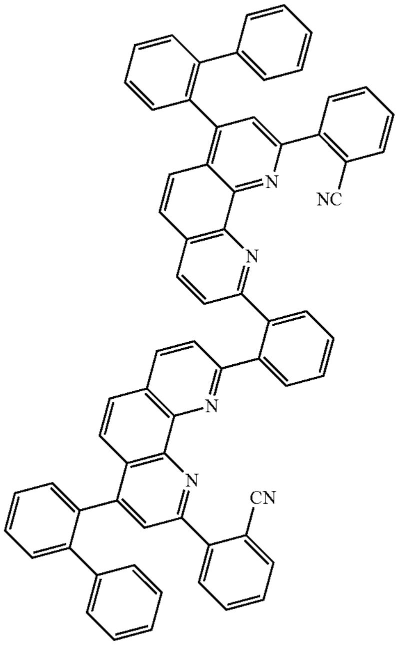
-continued
N-55
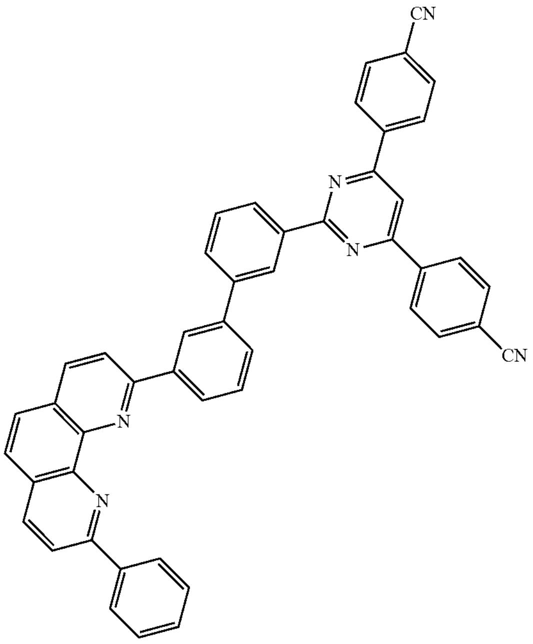
N-56
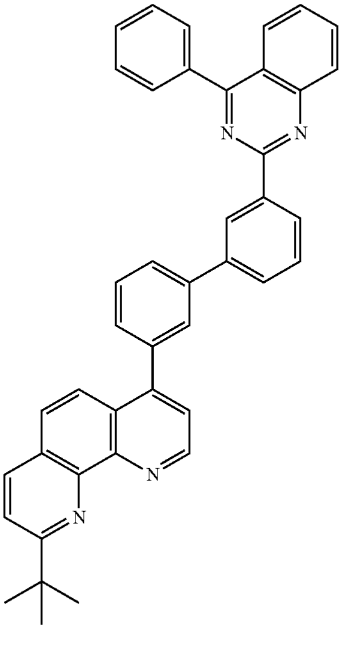

-continued
N-57
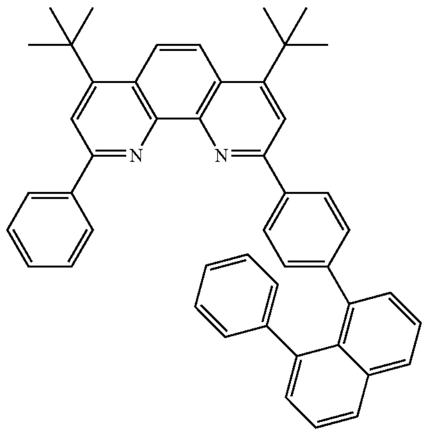
N-58
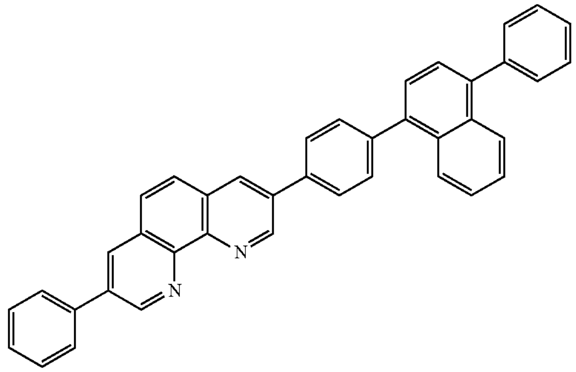
N-59
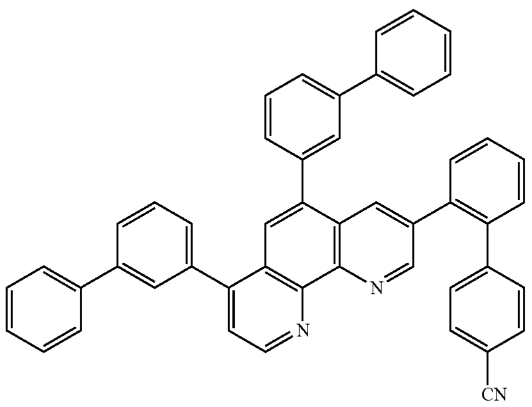
-continued
N-60
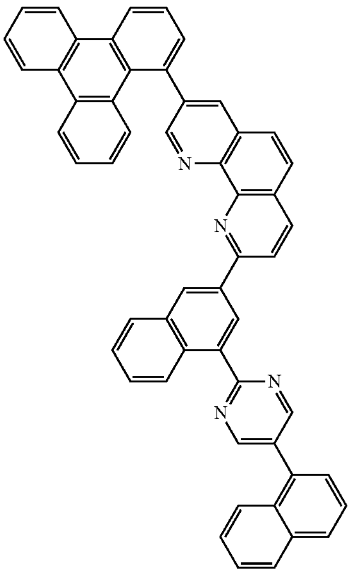
N-61
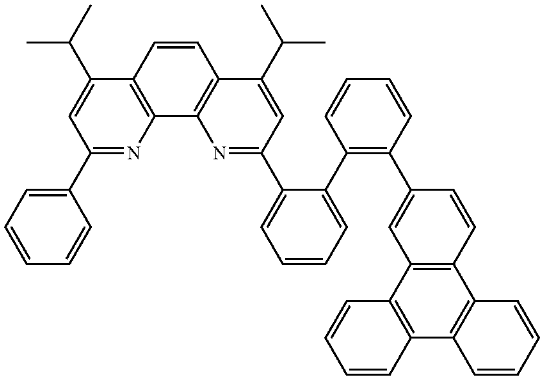
N-62
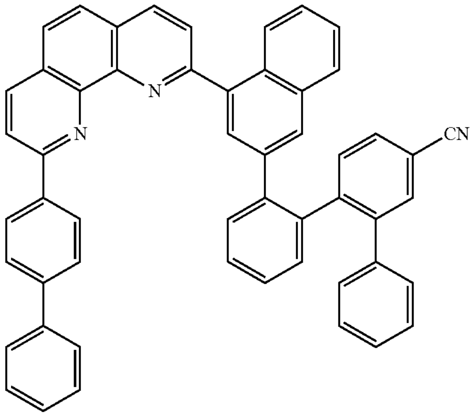

-continued
N-63
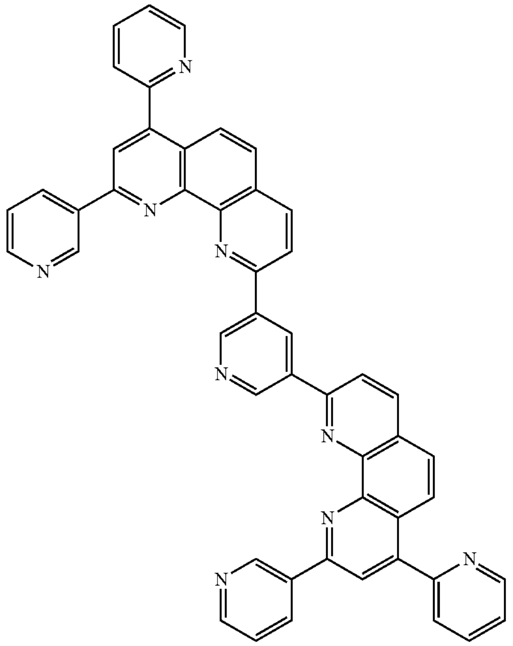
N-64
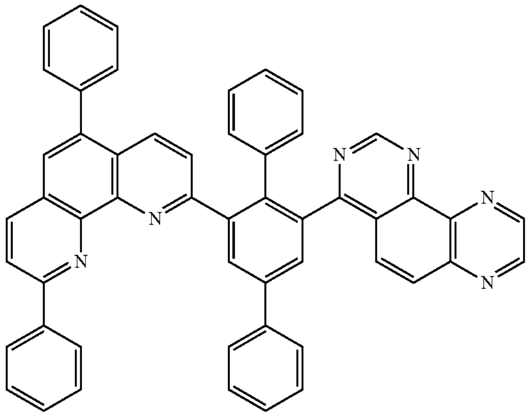
-continued
N-65
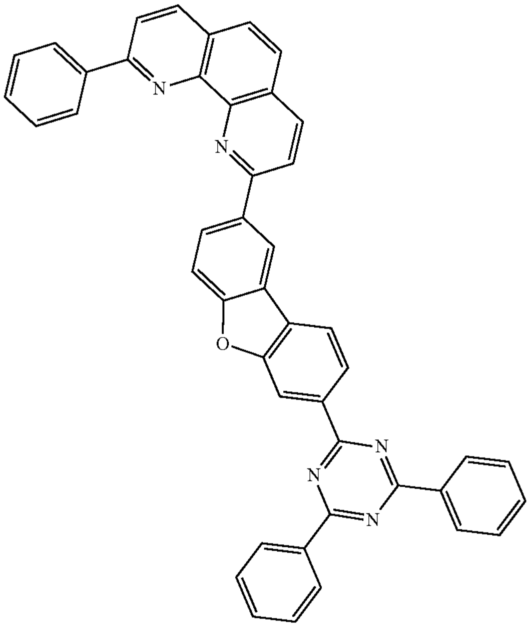
N-66
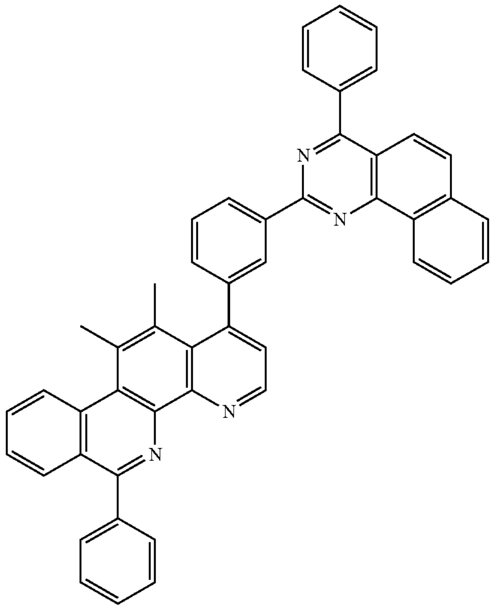

-continued
N-67
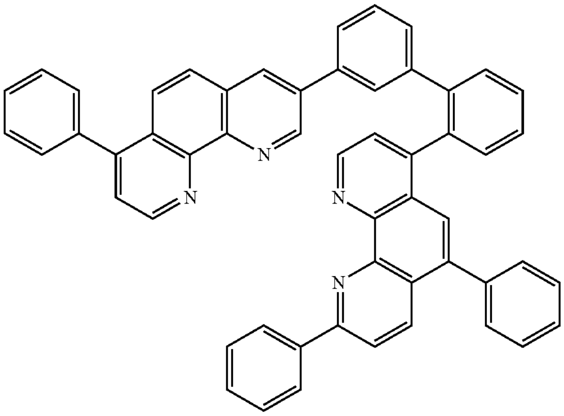
N-68
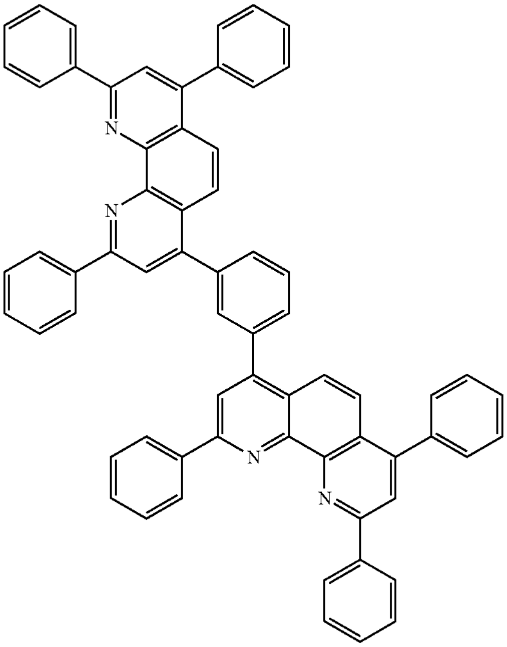
N-69
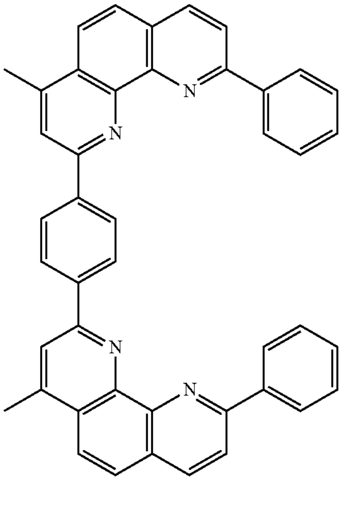
-continued
N-70
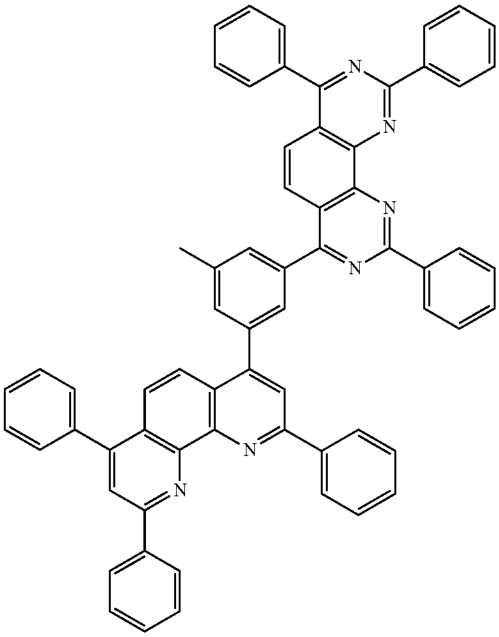
N-71
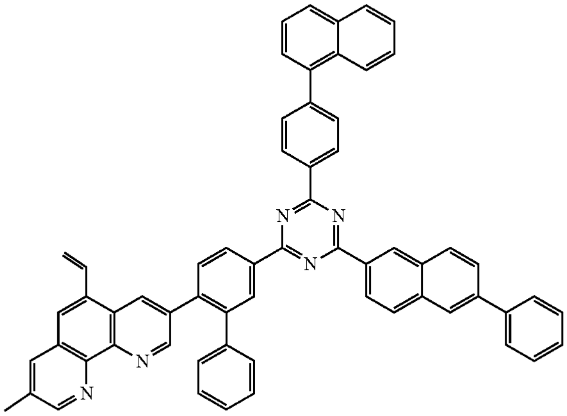
N-72
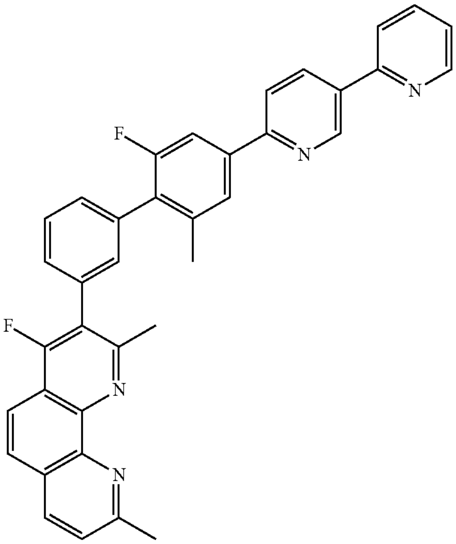

N-73
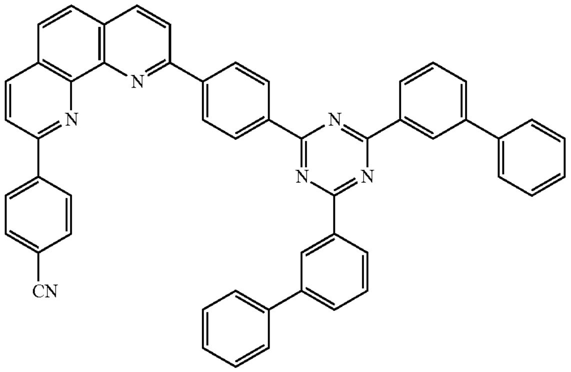
N-74
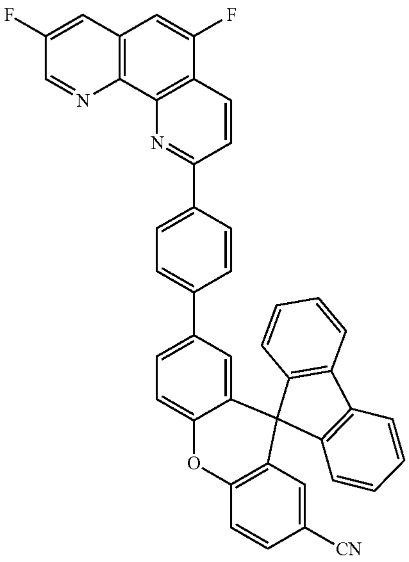
N-75
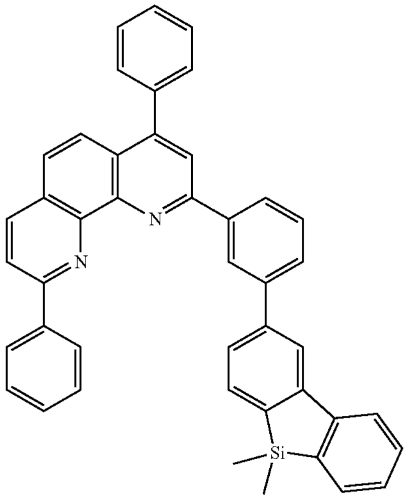
N-76
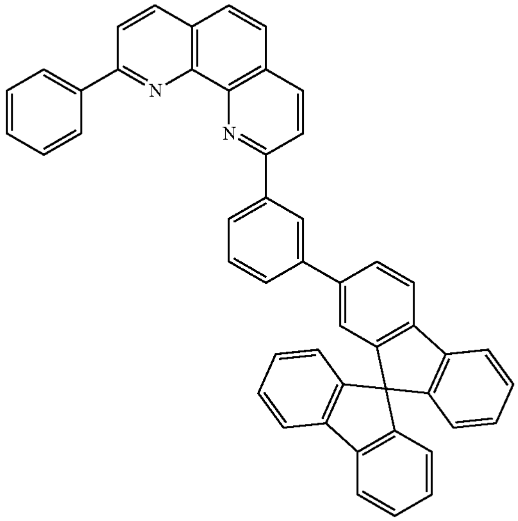
N-77
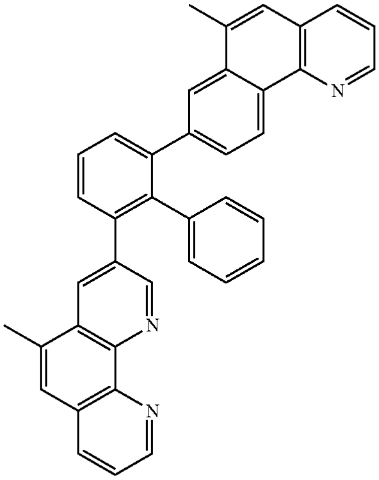

-continued
N-78
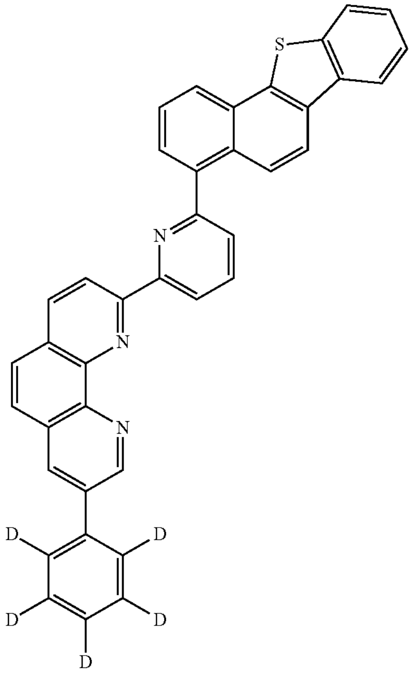
N-79
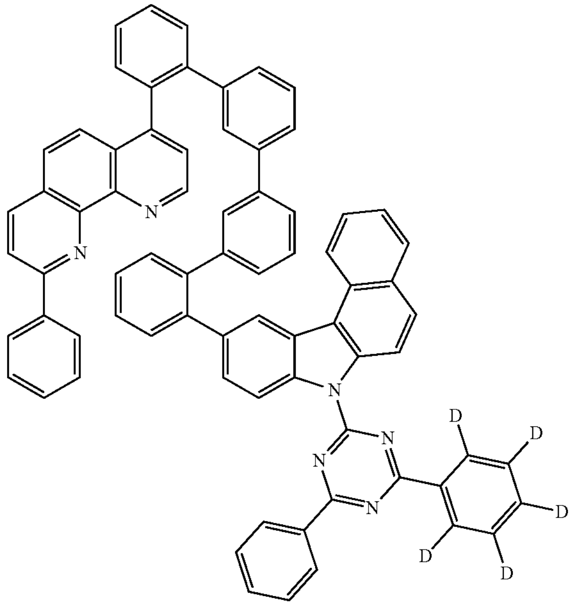
-continued
N-80
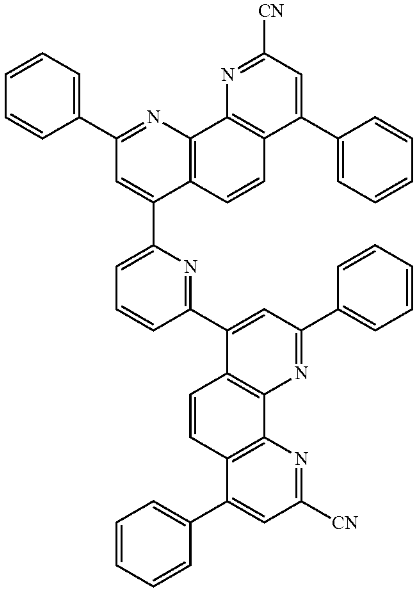
N-81
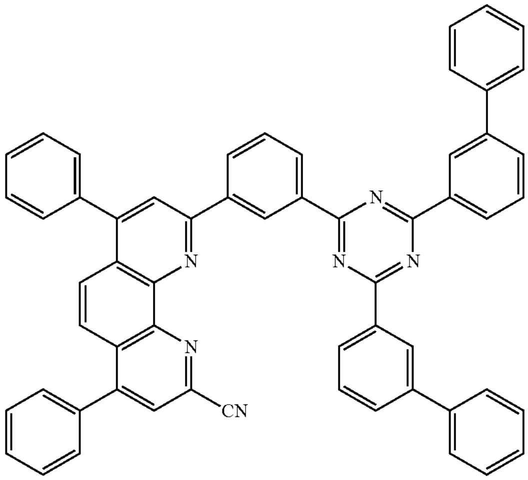
N-82
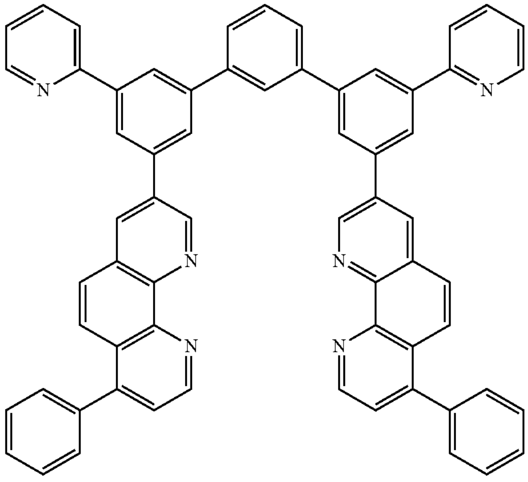

N-83
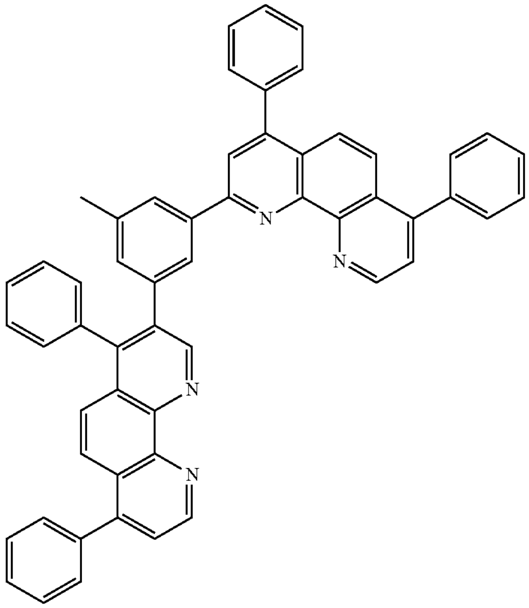
N-84
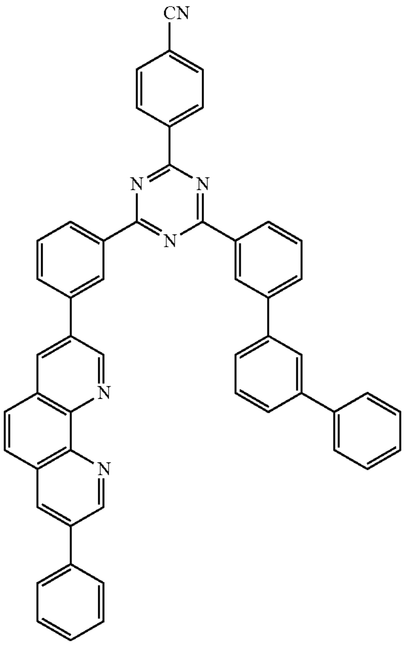
N-85
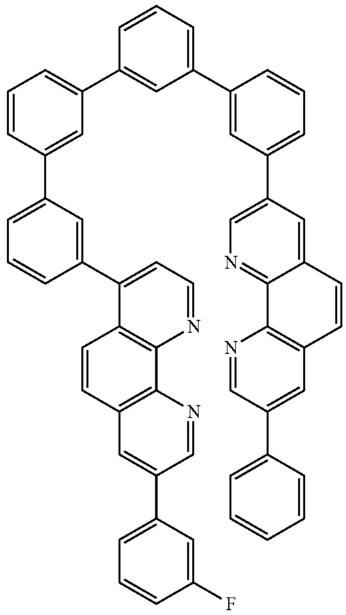
N-86
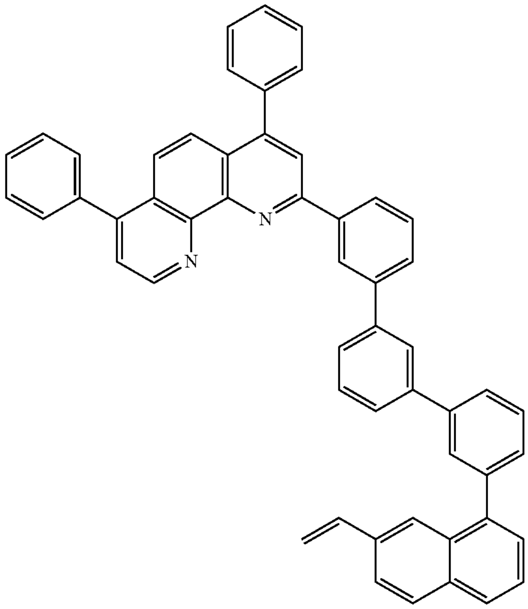

-continued
N-87
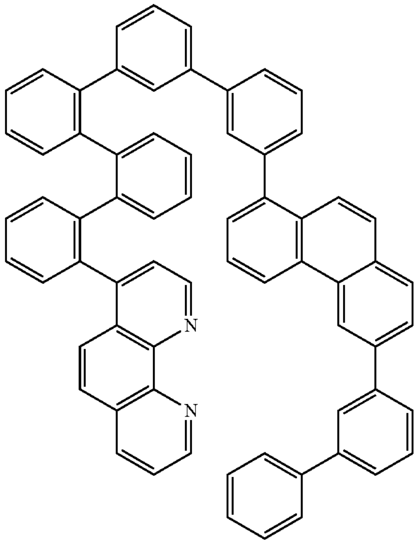
N-88
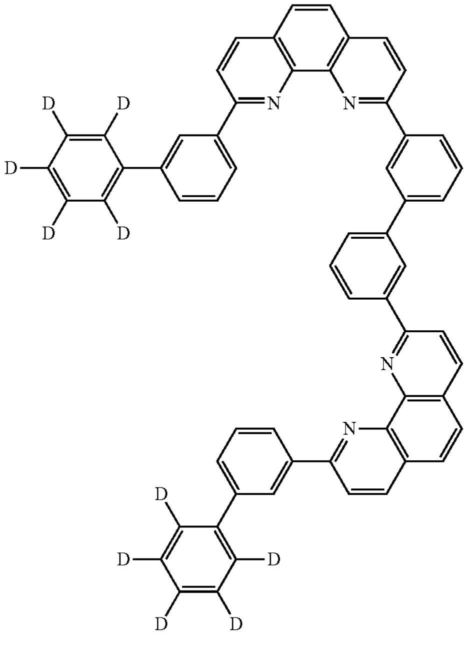
-continued
N-89
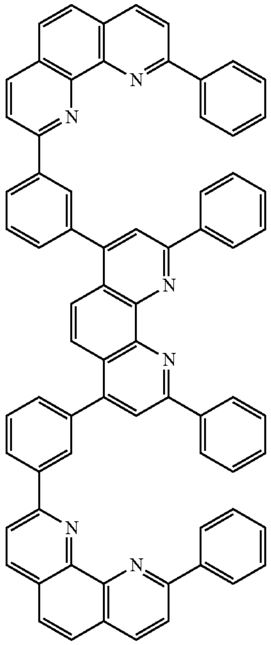
N-90
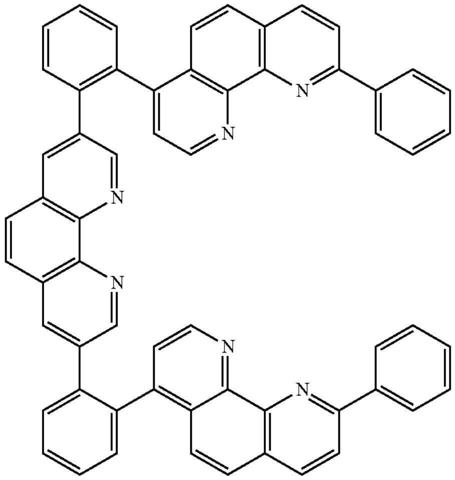

-continued
N-91
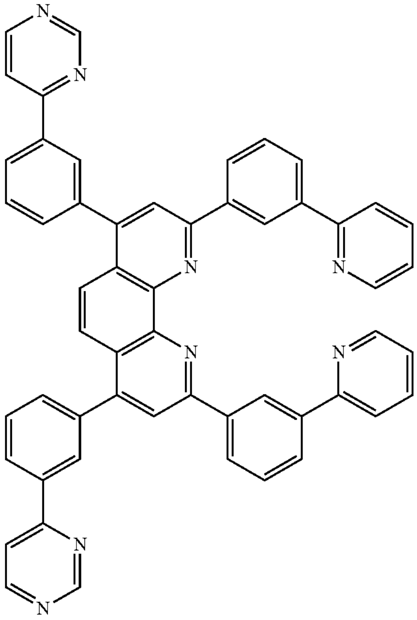
N-92
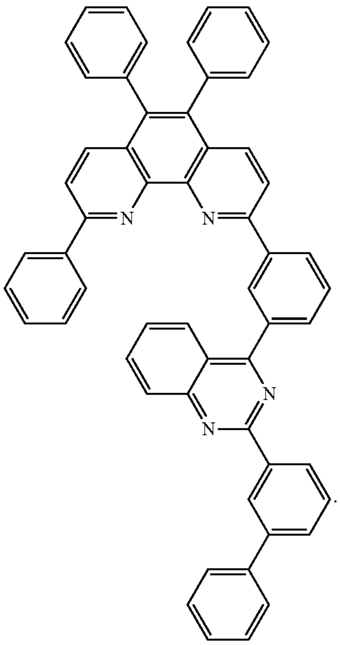
8. A compound selected from the group consisting of the following Compounds P-1 to P-16:
P-1
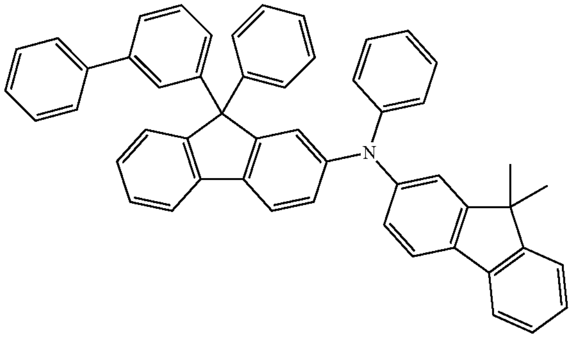
P-2
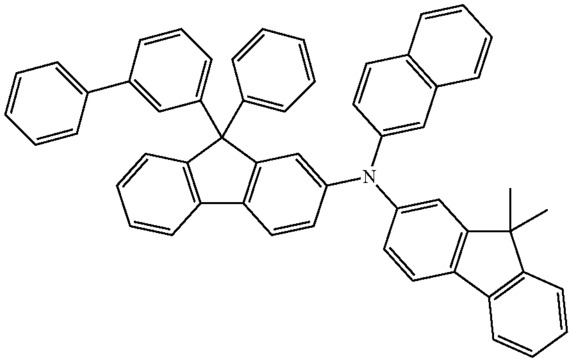
P-3
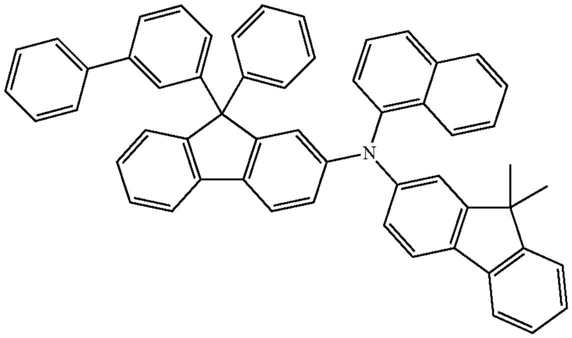
P-4
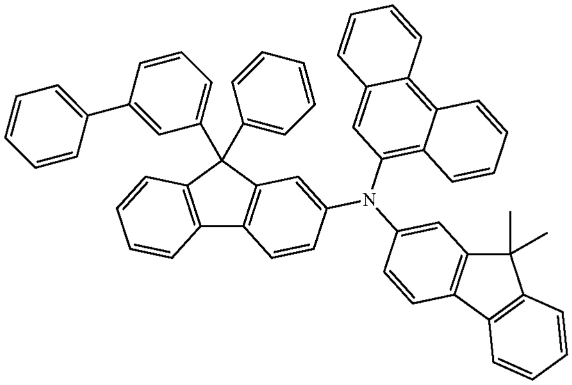

-continued
P-5
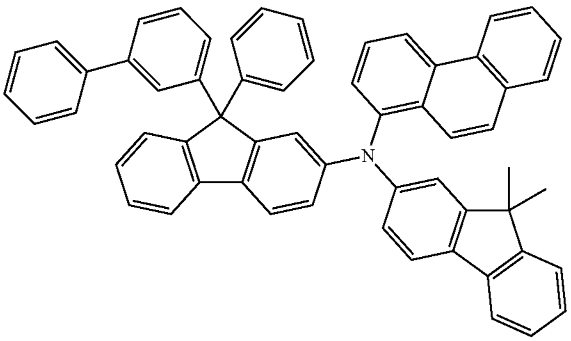
P-6
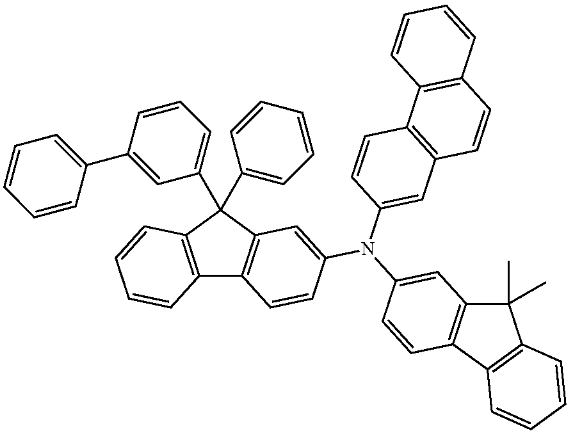
P-7
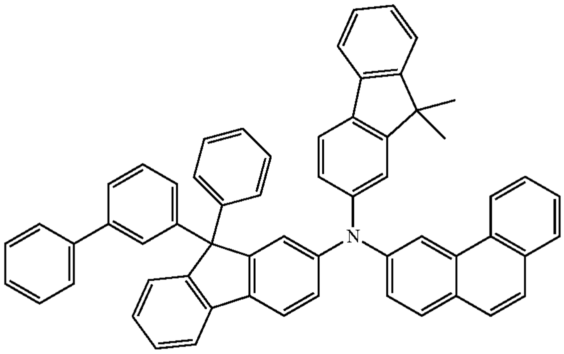
P-8
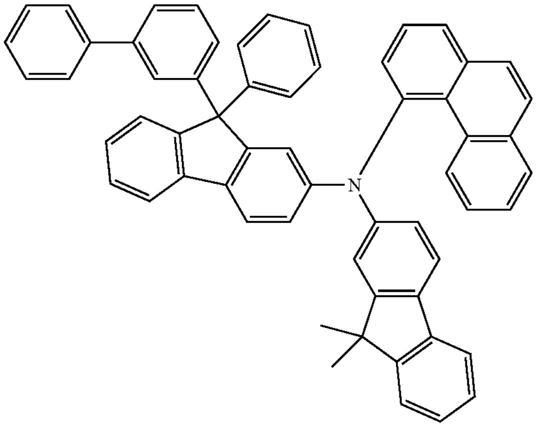
-continued
P-9
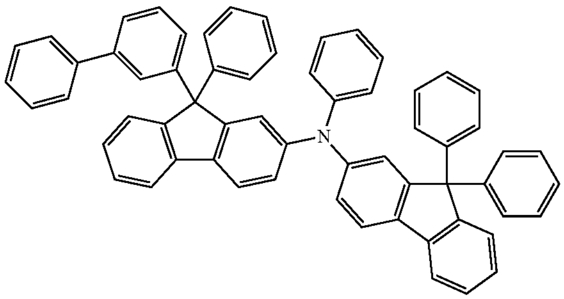
P-10
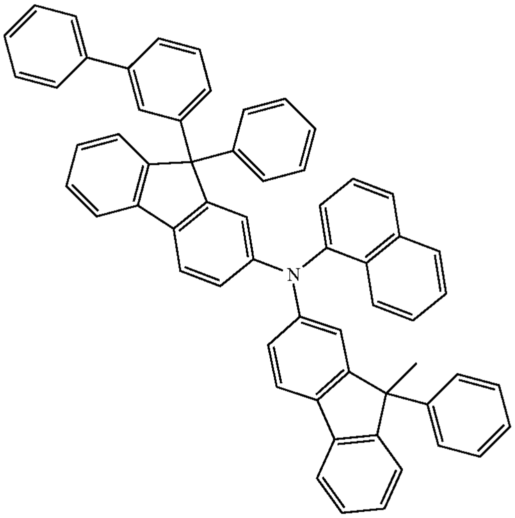
P-11
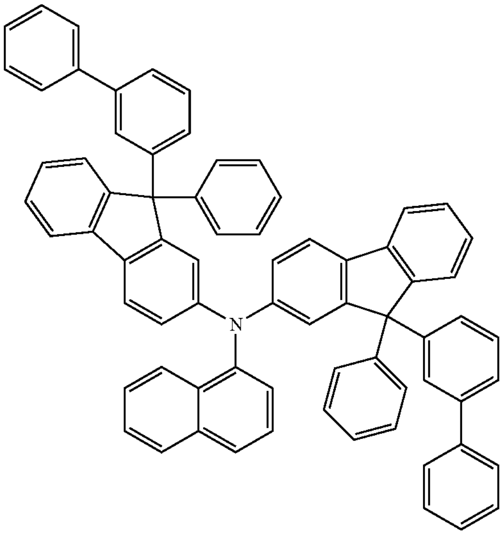

-continued

P-12

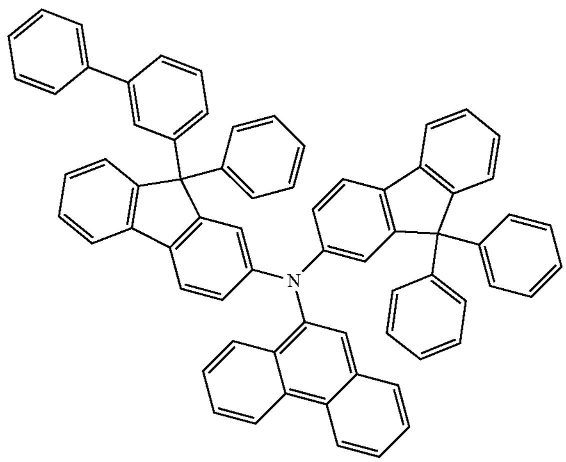

P-13

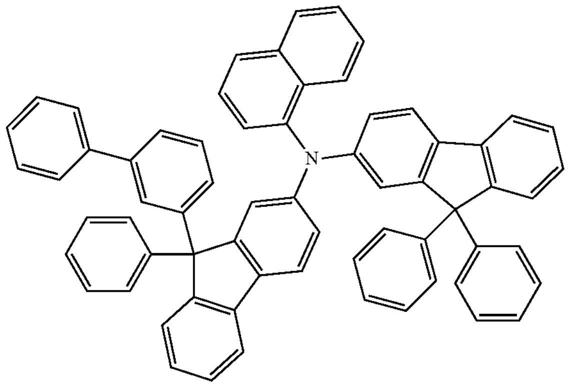

P-14

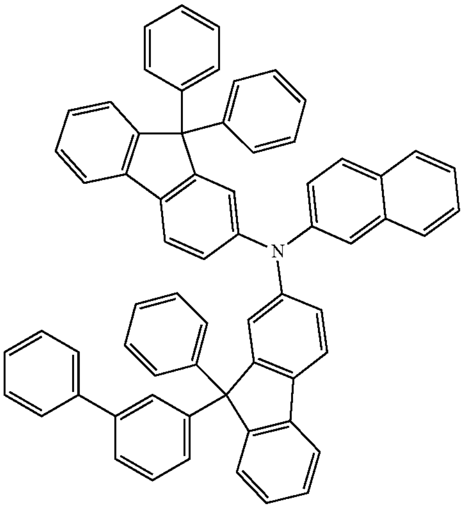

-continued

P-15

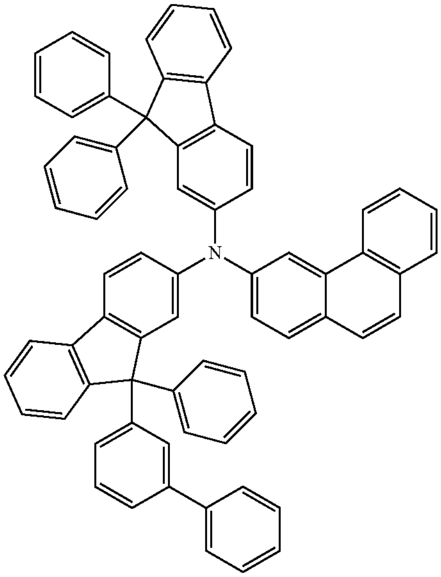

P-16

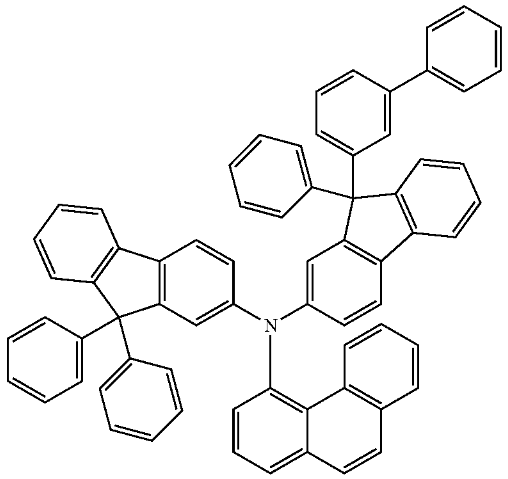

.

9. The organic electronic element of claim 1, further comprising a light efficiency enhancing layer formed on at least one surface of the first electrode and the second electrode, the surface being opposite to the organic material layer.

10. An electronic device comprising a display device comprising the organic electronic element of claim 1; and a control unit for driving the display device.

11. An electronic device according to claim 10, wherein the organic electronic element is at least one of an OLED, an organic solar cell, an organic photo conductor(OPC), organic transistor (organic TFT) and an element for mono-chromic or white illumination.

12. An organic electronic element comprising the compound according to claim 8.

13. An electronic device comprising a display device comprising the organic electronic element of claim 12; and a control unit for driving the display device.

14. A method for reusing a compound comprising:

depositing an organic light emitting material comprising a compound represented by any one of Compounds P-1 to P-16 of claim 8 in a manufacturing process of an organic light emitting device;

removing impurities from the crude organic light emitting material recovered from the deposition device;

recovering the removed impurities; and purifying the recovered impurities to a purity of 99.9% or higher.

* * * * *